United States Patent
Mori et al.

(10) Patent No.: US 8,686,098 B2
(45) Date of Patent: Apr. 1, 2014

(54) FLUORINE-CONTAINING COMPOUND, FLUORINE-CONTAINING POLYMER COMPOUND, RESIST COMPOSITION, TOP COAT COMPOSITION AND PATTERN FORMATION METHOD

(75) Inventors: Kazunori Mori, Iruma-gun (JP); Yuji Hagiwara, Kawagoe (JP); Masashi Nagamori, Fujimino (JP); Yoshimi Isono, Kawagoe (JP); Satoru Narizuka, Saitama (JP); Kazuhiko Maeda, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 32 days.

(21) Appl. No.: 13/375,026

(22) PCT Filed: May 20, 2010

(86) PCT No.: PCT/JP2010/058540
§ 371 (c)(1),
(2), (4) Date: Nov. 29, 2011

(87) PCT Pub. No.: WO2010/140483
PCT Pub. Date: Sep. 12, 2010

(65) Prior Publication Data
US 2012/0077126 A1    Mar. 29, 2012

(30) Foreign Application Priority Data
Jun. 1, 2009  (JP) ................... 2009-131919

(51) Int. Cl.
C08F 12/20    (2006.01)
C08F 216/12   (2006.01)
C07C 69/34    (2006.01)
G03F 7/004    (2006.01)
G03F 7/40     (2006.01)

(52) U.S. Cl.
USPC ........... 526/242; 526/247; 526/243; 560/192; 560/223; 430/270.1; 430/311; 430/285.1; 430/331; 430/330

(58) Field of Classification Search
USPC ........... 430/270.1, 285.1; 526/242, 247, 243; 560/192, 223
See application file for complete search history.

(56) References Cited

U.S. PATENT DOCUMENTS

| | | | |
|---|---|---|---|
| 5,670,593 | A | 9/1997 | Araki et al. |
| 7,402,626 | B2 | 7/2008 | Maeda et al. |
| 7,887,990 | B2 | 2/2011 | Isono et al. |
| 2005/0084231 | A1* | 4/2005 | Araki et al. ............ 385/147 |
| 2005/0215836 | A1 | 9/2005 | Komata et al. |
| 2009/0011199 | A1 | 1/2009 | Isono et al. |

FOREIGN PATENT DOCUMENTS

| | | | |
|---|---|---|---|
| JP | 1-242551 A | | 9/1989 |
| JP | 07117188 A | * | 5/1995 |
| JP | 10-161313 A | | 6/1998 |
| JP | 2000-89463 A | | 3/2000 |
| JP | 2004-175740 A | | 6/2004 |
| JP | 2005-206587 A | | 8/2005 |
| JP | 2005-239710 A | | 9/2005 |
| JP | 2005-316352 A | | 11/2005 |
| JP | 2006-321956 A | | 11/2006 |
| JP | 2007-31478 A | | 2/2007 |
| JP | 2007-63255 A | | 3/2007 |
| JP | 2007-91634 A | | 4/2007 |
| JP | 2007-264459 A | | 10/2007 |
| JP | 2008-44896 A | | 2/2008 |
| JP | 2009-19199 A | | 1/2009 |
| JP | 2009-29802 A | | 2/2009 |
| JP | 2009-51805 A | | 3/2009 |
| JP | 2010-204187 A | | 9/2010 |
| WO | WO 95/33782 A1 | | 12/1995 |

OTHER PUBLICATIONS

Machine translation of JP 07-117188(no. date).*
M. Switkes et al., "Resolution Enhancement of 157 nm Lithography Liquid Immersion", Proceedings of SPIE, 2002, pp. 459-465, vol. 4691, U.S.
"Resist and Cover Material Investigation for Immersion Lithography", $2_{nd}$ Immersion Work Shop, Jul. 11, 2003.
E. Ann Hallinan et al., "2,2-DifluOro-3-Hydroxyesters by Reformatskii Reaction" Tetrahedron Letters, 1984, pp. 2301-2302, vol. 25, No. 22, Great Britain.
PCT/ISA/237 Form (Four (4) pages).
International Search Report including English language translation dated Jun. 15, 2010 (Five (5) pages).
Japanese Office Action dated Oct. 8, 2013 (two (2) pages).

* cited by examiner

Primary Examiner — Amanda C. Walke
(74) Attorney, Agent, or Firm — Crowell & Moring LLP

(57) ABSTRACT

A fluorine-containing polymer of the present invention contains a repeating unit (a) of the general formula (2) and has a mass-average molecular weight of 1,000 to 1,000,000. This polymer is suitably used in a resist composition for pattern formation by high energy ray radiation of 300 nm or less wavelength or electron beam radiation or a top coat composition for liquid immersion lithography and is characterized as having high water repellency, notably high receding contact angle.

[Chem. 72]

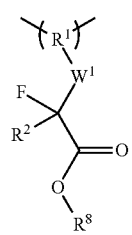

(2)

In the formula, $R^1$ represents a polymerizable double bond-containing group; $R^2$ represents a fluorine atom or a fluorine-containing alkyl group; $R^8$ represents a substituted or unsubstituted alkyl group or the like; and $W^1$ represents a single bond, a substituted or unsubstituted methylene group or the like.

19 Claims, No Drawings

FLUORINE-CONTAINING COMPOUND, FLUORINE-CONTAINING POLYMER COMPOUND, RESIST COMPOSITION, TOP COAT COMPOSITION AND PATTERN FORMATION METHOD

TECHNICAL FIELD

The present invention relates to a novel fluorine-containing compound, a fluorine-containing polymer derived from the fluorine-containing compound, a resist composition and a top coat composition, each of which using the fluorine-containing polymer, and a pattern formation method using the resist composition or the top coat composition.

BACKGROUND ART

With the recent development of digital devices such as computers, it has become common to process an enormous amount of operational data or two- or three-dimensional image data. There is a need to provide large-capacity high-speed memories and high-performance microprocessors for quick processing of such enormous information. Further, the processing power required of the digital devices is estimated to increase more and more as the broadband spreads with the development of network systems such as the Internet.

In order to meet this need, various devices such as semiconductor devices are required to achieve higher density and higher integration. The requirements for photolithography processes, which enable fine patterning, are particularly becoming more stringent year by year. For example, photolithography process using ArF excimer laser radiation (wavelength: 193 nm) has been put into use in response to the requirement for patterning techniques with a minimum line width of 0.13 µm or less for production of 1-Gbit or higher-capacity DRAMs. The development of photolithography process using extreme ultraviolet (EUV) radiation has also been pursued for finer patterning.

Although novolac resins and polyvinylphenol resins are conventionally used in resist compositions, these resins show too high light absorption to be used in the above wavelength ranges. The use of acrylic resins (see e.g. Patent Document 1) and cycloolefin resins (see e.g. Patent Document 2) as alternative resist resins is thus being examined.

The change of light sources and the improvement of exposure apparatuses are also being examined in order to achieve the finer device structures. For example, steppers (reduced projection type exposure apparatuses) have been improved significantly by performance improvements to reduced projection lenses and design modifications to optical systems. The performance of the projection lens used in the stepper is generally expressed as NA (numerical aperture). As the physical limitation of the NA of the projection lens is of the order of 0.9 and has already been accomplished, it has been attempted to increase the NA of the projection lens to be 1.0 or higher by filling any medium of higher refractive index than the air into the space between the lens and wafer. Among others, attentions are being given to liquid immersion exposure processing using pure water (hereinafter sometimes just called water) as the medium (see Non-Patent Document 1).

There are pointed out various problems in liquid immersion lithography as the liquid immersion lithography involves contact of the resist film with the medium (such as water). In particular, the occurrence of changes in pattern shape due to the dissolution of an acid generated in the film by exposure or an amine compound added as a quencher into water and the occurrence of pattern collapse due to the film swelling become issues. It has been reported that it is effective against these problems to improve the water repellency of the resist film for separation of the resist film and water. It has also been reported that it is effective to form a water-repellent top coat film on the resist film (see Non-Patent Document 2).

Various fluorine-containing polymers for fluorine-containing resist materials have been developed as the use of fluorine-containing resist compositions is effective for improvements in resist water repellency. The present applicant has disclosed a difluoroacetic acid having a polymerizable double bond-containing group (see Patent Document 3) and a difluoroacetic acid ester having in its ester moiety an acid-labile protecting group such as t-butyl or methoxymethyl group and an ester group (see Patent Document 4). However, each of these patent documents is intended for use of the difluoroacetic acid or difluoroacetic acid ester as a negative or positive resist and does not disclose an ester polymer having no acid-labile protecting group. As non-polymerizable compounds similar to the above polymerizable compounds, carboxylic acid compounds having a fluorine atom in $\alpha$-position, such as 2-fluoro-phenylacetic acid and esters thereof (see Patent Document 5) and ethyl-2,2-difluoro-3-hydroxy-3-phenyl-propionic acid (see Non-Patent Document 3), are known.

On the other hand, the top coat film for separation of the resist film and water is required to have good solubility in developer, resistance to pure water and capabilities of separating the resist film and water and not damaging the resist film. As a top coat composition satisfying these requirements, there has been developed a composition of a fluorine-containing polymer having a repeating unit formed with two or more hexafluoroisopropylhydroxyl groups. This fluorine-containing polymer composition is reported to have particularly good solubility in developer (see Patent Document 6).

In general, it is required that the top coat composition applied to the resist film for protection of the resist film has good solubility in developer, resistance to pure water and capabilities of separating the resist film and water and not damaging the resist film as mentioned above. If the developer solubility of the top coat composition is low, it is unfavorably impossible to obtain a rectangular cross-section resist pattern due to deterioration in photoresist performance by insufficient removal of the top coat film. If the developer solubility of the resist composition is too high, the resist film may be reduced in thickness. It is thus desirable that the top coat composition shows adequate developer solubility.

PRIOR ART DOCUMENTS

Patent Documents

Patent Document 1: Japanese Laid-Open Patent Publication No. H10-161313

Patent Document 2: Japanese Laid-Open Patent Publication No. 2000-89463

Patent Document 3: Japanese Laid-Open Patent Publication No. 2009-29802

Patent Document 4: Japanese Laid-Open Patent Publication No. 2009-19199

Patent Document 5: Japanese Laid-Open Patent Publication No. H01-242551

Patent Document 6: Japanese Laid-Open Patent Publication No. 2005-316352

Non-Patent Documents

Non-Patent Document 1: Proceedings of SPIE (U.S.), 2002, Vol. 4691, pp. 459-465
Non-Patent Document 2: 2nd Immersion Work Shop, Jul. 11, 2003, Resist and Cover Material Investigation for Immersion Lithography
Non-Patent Document 3: Tetrahedron Letters, Vol. 25, No. 22, pp. 2301-2302, 1984

SUMMARY OF THE INVENTION

Problems to be Solved by the Invention

Under the above circumstances, it is an object of the present invention to provide a pattern formation method capable of forming a rectangular cross-section resist pattern by the use of a chemically amplified resist material having high transparency to Kr excimer laser radiation, ArF excimer laser radiation or higher energy ray radiation or electron beam radiation and high resolution. It is also an object of the present invention to provide a resist composition for forming a resist film with sufficient water repellency to withstand use in so-called liquid immersion lithography process, which utilizes a medium during exposure, a top coat composition for coating an insufficiently water-repellent resist film and thereby forming a multilayer film structure suitable for use in liquid immersion lithography process, and a fluorine-containing polymer for preparation of the resist composition or the top coat composition.

Means for Solving the Problems

The present inventors have made researches on the introduction of a fluorine atom into a base resin (i.e. a resin with a resist function) for improvement of the water repellency of a resist film and have found that, even though the resist film does not always exhibit sufficient water repellency and notably does not allow increase in receding contact angle by the introduction of a fluorine atom to a repeating unit of the base resin, it is possible to significantly improve the water repellency of the resist film so that the resist film can be formed with a desired pattern by liquid immersion lithography process by the introduction of a fluorine atom to the α-position relative to an ester group of the repeating unit of the base resin. Further, the present inventors have found that a top coat film, when formed from a fluorine-containing polymer having such a repeating unit but not having a resist function, exhibits high water repellency for use as a coating on a conventional resist film so that the resist film can be formed with a desired pattern by liquid immersion lithography process. The present inventors have also found a fluorine-containing unsaturated carboxylic acid ester as a fluorine-containing compound suitable for the introduction of the above repeating unit into the fluorine-containing polymer. The present invention is based on these findings.

In the present specification, the term "alkyl group" refers to a straight, branched or cyclic alkyl group. Herein, the cyclic alkyl group can also be classified as an "alicyclic group" or "alicyclic hydrocarbon group". The term "lower" of the lower alkyl group etc. means that the group to which the term is attached has 1 to 4 carbon atoms. However, the lower cyclic alkyl group refers to an alkyl that has a ring structure of 3 to 10 carbon atoms and may have a lower alkyl group as a substituent. Examples of such an alkyl group are methyl, ethyl, propyl, butyl, cyclopentyl, cyclohexyl, norbornyl, adamantyl, trifluoromethyl, 2,2,2-trifluoroethyl, 1-(trifluoromethyl)ethyl and 3,3,3-trifluoropropyl. The typical name or structural formula of a compound, when there can exist isomers of the compound, indicate all possible isomers unless otherwise specified. Further, the term "halogen" refers to fluorine, chlorine, bromine or iodine. In the present specification, the "resist composition" refers to that having a resist function and containing no solvent; whereas the term "resist composition solution" or "resist solution" refers to that having a resist function and containing a solvent. Similarly, the term "top coat composition" refers to that containing no solvent; whereas the term "top coat composition solution" or "top coat solution" refers to that containing a solvent.

The present invention includes the following aspects.

[Inventive Aspect 1]

A fluorine-containing polymer comprising a repeating unit (a) of the following general formula (2) and having a mass-average molecular weight of 1,000 to 1,000,000,

[Chem. 1]

(2)

where $R^1$ represents one of the following formulas:

[Chem. 2]

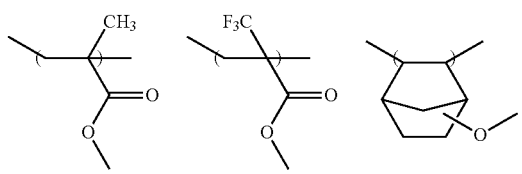

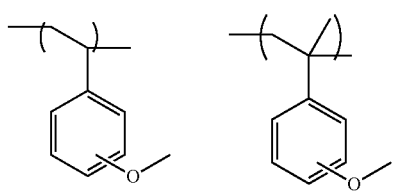

$R^2$ represents a fluorine atom or a fluorine-containing alkyl group;

$R^8$ represents a substituted or unsubstituted alkyl group of the general formula (4) or an aryl group:

[Chem. 3]

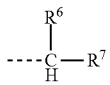
(4)

(where $R^5$ and $R^6$ each independently represent a hydrogen atom, a substituted or unsubstituted alkyl or aryl group; and $R^5$, $R^6$ and a carbon atom in the general formula (4) may be bonded together to form an alicyclic hydrocarbon group);

any number of hydrogen atoms in $R^8$ may be substituted with a halogen atom, a hydroxyl group, an alkyl group, a fluorine-containing alkyl group or an aryl group;

any methylene group ($CH_2$) in $R^8$ (except for that containing the carbon atom represented by C in the general formula (4)) may be replaced by a carbonyl group (C=O), an ether group (O), an imide group (NH), a thioether group (S), a sulfinyl group (SO) or a sulfonyl group ($SO_2$);

$W^1$ represents a divalent linking group having a main skeleton formed by one atomic group, or two or more atomic groups in combination, selected from the group consisting of a single bond, substituted or unsubstituted methylene groups, divalent cyclic alkyl groups (alicyclic hydrocarbon groups), divalent aryl groups (aromatic hydrocarbon groups), substituted or unsubstituted condensed polycyclic aromatic groups, divalent heterocyclic groups, a carbonyl group, an ether group, an ester bond, an oxycarbonyl bond, a thioether group, an amide bond, a sulfonamide bond, an urethane bond and an urea bond;

the linking group may have a plurality of atomic groups of the same kind;

any number of hydrogen atoms bonded to any carbon atom in the linking group may be substituted with a fluorine atom; and any atoms in the linking group may be bonded together to form a ring structure.

[Inventive Aspect 2]

The fluorine-containing polymer according to Inventive Aspect 1, wherein $R^2$ is a fluorine atom.

[Inventive Aspect 3]

The fluorine-containing polymer according to Inventive Aspect 1 or 2, further comprising a repeating unit (c) formed by cleavage of a polymerizable double bond of a copolymerizable monomer selected from the group consisting of maleic anhydride, acrylic acid esters, fluorine-containing acrylic acid esters, methacrylic acid esters, fluorine-containing methacrylic acid esters, styrenic compounds, fluorine-containing styrenic compounds, vinyl ethers, fluorine-containing vinyl ethers, allyl ethers, fluorine-containing allyl ethers, olefins, fluorine-containing olefins, norbornene compounds, fluorine-containing norbornene compounds, sulfur dioxide, vinyl silanes, vinyl sulfonic acids and vinyl sulfonic acid esters and each having none of an acid-labile group and an alcoholic hydroxyl group.

[Inventive Aspect 4]

The fluorine-containing polymer according to any one of Inventive Aspects 1 to 3, further comprising a repeating unit of the general formula (5):

[Chem. 4]

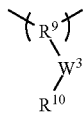
(5)

where $R^9$ represents one of the following formulas:

[Chem. 5]

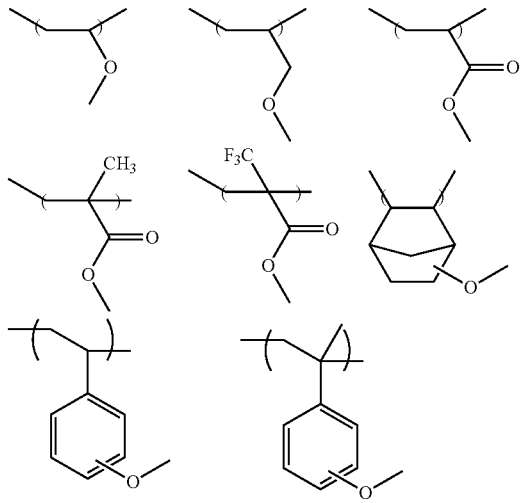

$R^{10}$ represents an acid-labile protecting group; and $W^3$ represents a divalent linking group having a main skeleton formed by one atomic group, or two or more atomic groups in combination, selected from the group consisting of a single bond, substituted or unsubstituted methylene groups, divalent cyclic alkyl groups (alicyclic hydrocarbon groups), divalent aryl group (aromatic hydrocarbon groups), substituted or unsubstituted condensed polycyclic aromatic groups, divalent heterocyclic groups, a carbonyl group, an ether group, a ester bond, an oxycarbonyl bond, a thioether group, an amide bond, a sulfonamide bond, an urethane bond and an urea bond;

the linking group may have a plurality of atomic groups of the same kind;

any number of hydrogen atoms bonded to any carbon atom in the linking group may be substituted with a fluorine atom; and any atoms in the linking group may be bonded together to form a ring structure.

[Inventive Aspect 5]

A positive resist composition solution comprising at least the fluorine-containing polymer according to Inventive Aspect 4, a photoacid generator and a solvent.

[Inventive Aspect 6]

A pattern formation method, comprising at least: applying the resist composition solution according to Inventive Aspect 5 to a substrate; heat treating the substrate, thereby forming a resist film from the resist composition solution; exposing the resist film to high energy ray radiation of 300 nm or less wavelength or electron beam radiation through a photomask; heat treating the exposed resist film; and developing the exposed and heat treated resist film.

[Inventive Aspect 7]

A top coat composition comprising at least the fluorine-containing polymer according to Inventive Aspect 1 or 2.

[Inventive Aspect 8]

A top coat composition solution comprising at least the fluorine-containing polymer according to Inventive Aspect 1 or 2 and a solvent.

[Inventive Aspect 9]

The top coat composition solution according to Inventive Aspect 8, wherein the solvent is one kind of solvent, or a mixed solvent of two or more kinds of solvents, selected from the group consisting of $C_5$-$C_{20}$ cyclic or chain hydrocarbons, $C_1$-$C_{20}$ hydrocarbon alcohols, partially fluorinated $C_5$-$C_{20}$ cyclic or chain hydrocarbons, and partially fluorinated $C_1$-$C_{20}$ hydrocarbon alcohols.

[Inventive Aspect 10]

The top coat composition solution according to Inventive Aspect 8 or 9, wherein the solvent is a mixed solvent of 50 to 99.9 mass % of a $C_5$-$C_{20}$ hydrocarbon and 0.1 to 50 mass % of a $C_1$-$C_{20}$ hydrocarbon alcohol.

[Inventive Aspect 11]

The top coat composition solution according to any one of Inventive Aspects 8 to 10, wherein the solvent or the mixed solvent has a boiling point of 70 to 170° C.

[Inventive Aspect 12]

The top coat composition solution according to any one of Inventive Aspects 8 to 11, wherein the top coat composition solution is used for liquid immersion lithography.

[Inventive Aspect 13]

A pattern formation method, comprising at least: applying a positive resist composition solution to a substrate; heat treating the substrate, thereby forming a resist film; forming a top coat film on a surface of the resist film to provide a multilayer film in which the resist film and the top coat film are laminated on the substrate; exposing the multilayer film to high energy ray radiation of 300 nm or less wavelength or electron beam radiation; heat treating the exposed multilayer film; and developing the exposed and heat treated multilayer film. The top coat film is preferably a film of a top coat composition comprising a fluorine-containing polymer according to inventive aspect 1 or 2.

[Inventive Aspect 14]

The pattern formation method according to Inventive Aspect 13, wherein the developing includes removing the top coat film substantially simultaneously with developing the resist film with an alkali developer.

[Inventive Aspect 15]

A fluorine-containing unsaturated carboxylic acid ester of the following general formula (1):

[Chem. 6]

$$R^0\text{-}W^1\text{-}\underset{\underset{R^2}{|}}{\overset{\overset{F}{|}}{C}}\text{-}\underset{\underset{O}{\parallel}}{C}\text{-}O\text{-}R^3 \quad (1)$$

where $R^0$ represents one of the following formulas:

[Chem. 7]

$R^2$ represents a fluorine atom or a fluorine-containing alkyl group;

$R^3$ represents a substituted or unsubstituted alkyl group of the general formula (4) or an aryl group:

[Chem. 8]

$$\text{----}\underset{\underset{H}{|}}{\overset{\overset{R^6}{|}}{C}}\text{---}R^7 \qquad (4)$$

(where $R^5$ and $R^6$ each independently represent a hydrogen atom, a substituted or unsubstituted alkyl or aryl group; and $R^5$, $R^6$ and a carbon atom in the general formula (4) may be bonded together to form an alicyclic hydrocarbon group);

any number of hydrogen atoms in $R^8$ may be substituted with a halogen atom, a hydroxyl group, an alkyl group, a fluorine-containing alkyl group or an aryl group;

any methylene group ($CH_2$) in $R^8$ (except for that containing the carbon atom represented by C in the general formula (4)) may be replaced by a carbonyl group (C=O), an ether group (O), an imide group (NH), a thioether group (S), a sulfinyl group (SO) or a sulfonyl group ($SO_2$);

$W^1$ represents a divalent linking group having a main skeleton formed by one atomic group, or two or more atomic groups in combination, selected from the group consisting of a single bond, substituted or unsubstituted methylene groups, divalent cyclic alkyl groups (alicyclic hydrocarbon groups), divalent aryl groups (aromatic hydrocarbon groups), substituted or unsubstituted condensed polycyclic aromatic groups, divalent heterocyclic groups, a carbonyl group, an ether group, an ester bond, an oxycarbonyl bond, a thioether group, an amide bond, a sulfonamide bond, an urethane bond and an urea bond;

the linking group may have a plurality of atomic groups of the same kind;

any number of hydrogen atoms bonded to any carbon atom in the linking group may be substituted with a fluorine atom; and any atoms in the linking group may be bonded together to form a ring structure.

[Inventive Aspect 16]

The fluorine-containing unsaturated carboxylic acid ester according to Inventive Aspect 15, wherein $R^2$ is a fluorine atom.

[Inventive Aspect 17]

The pattern formation method according to Inventive Aspect 13, wherein the positive resist composition solution contains propylene propylene glycol monomethyl ether acetate as a solvent.

It is possible that, in liquid immersion lithography using high energy ray radiation of 300 nm or less wavelength, the resist film formed from the resist composition solution of the present invention can attain improved surface water repellency, notably receding contact angle, for improvement of stepper throughput and obtain a clear rectangular cross-section resist pattern. Further, the top coat composition solution of the present invention does not dissolve the resist film so that the top coat film can be formed uniformly from the top coat composition on the surface of the resist film. It is possible that, in liquid immersion lithography using high energy ray radiation of 300 nm or less wavelength, the resist film with such a top coat film can attain improved surface water repellency, notably receding contact angle, for improvement of stepper throughput, secure adequate developer solubility without causing elution of resist film components into a liquid immersion medium, and obtain a clear rectangular cross-section resist pattern. Furthermore, the fluorine-containing unsaturated carboxylic acid ester of the present invention is useful for preparation of the fluorine-containing polymer of the resist composition or top coat composition of the present invention.

BEST MODES FOR CARRYING OUT THE INVENTION

Hereinafter, the respective components of the present invention will be described in detail below. It is noted that: the present invention is not limited to the following embodiments. Various changes and modifications can be made to the following embodiments based on the ordinary knowledge of one skilled in the art without departing from the scope of the present invention. All such embodiments are intended to fall within the scope of the present invention.

A fluorine-containing polymer of the present invention has a repeating unit (a) of the general formula (2) obtained by cleavage of a polymerizable double bond of a fluorine-containing compound of the general formula (1) either solely or in combination with a repeating unit(s) obtained by cleavage of a polymerizable double bond(s) of any other monomer(s).

[Fluorine-Containing Unsaturated Carboxylic Acid Ester]

[Chem. 9]

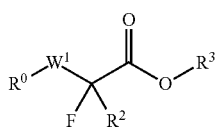

(1)

In the fluorine-containing unsaturated carboxylic acid ester of the general formula (1), $R^2$ is a fluorine atom or a fluorine-containing alkyl group. There is no particular limitation on the fluorine-containing alkyl group. Examples of the fluorine-containing alkyl groups are those having 1 to 12 carbon atoms, preferably 1 to 3 carbon atoms, such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl. A fluorine atom and a trifluoromethyl group are more preferred as $R^2$.

As $R^0$, there can be used any polymerizable double bond-containing group. Preferably, $R^0$ is either one of polymerizable double bond-containing groups of the following formulas.

[Chem. 10]

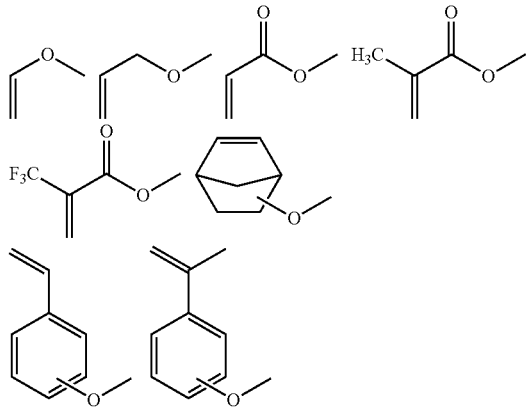

Among others, an acryloyloxy group, a methacryloyloxy group, a trifluoromethacryloyloxy group and an allyloxy group are more preferred.

The linking group $W^1$ is a divalent linking group having a main skeleton formed by one atomic group, or two or more kinds of atomic groups in combination, selected from the group consisting of a single bond, substituted or unsubstituted methylene groups, divalent cyclic alkyl groups (alicyclic hydrocarbon groups), divalent aryl groups (aromatic hydrocarbon groups), substituted or unsubstituted condensed polycyclic aromatic groups, divalent heterocyclic groups, a carbonyl group, an ether group, an ester bond, an oxycarbonyl bond, a thioether group, an amide bond, a sulfonamide bond, an urethane bond and an urea bond. The linking group may have a plurality of atomic groups of the same kind. Any number of hydrogen atoms bonded to any carbon atom in the linking group may be substituted with a fluorine atom. Any atoms in the linking group may be bonded together to form a ring structure.

The substituted methylene group constituting the main skeleton of the linking group $W^1$ is represented by the following general formula (3).

[Chem. 11]

$$—CR^4R^5— \quad (3)$$

There is no particular limitation on the monovalent substituent $R^4$, $R^5$ of the substituted methylene group. As the monovalent substituent group $R^4$, $R^5$, there can be used a hydrogen atom, a halogen atom, a hydroxyl group or a $C_1$-$C_{30}$ monovalent group selected from a substituted or unsubstituted alkyl group, a substituted or unsubstituted alicyclic hydrocarbon group, an alkoxyl group, a substituted or unsubstituted aryl group and a substituted and unsubstituted condensed polycyclic aromatic group. The monovalent substituent group $R^4$, $R^5$ may contain a fluorine atom, an oxygen atom, a sulfur atom or a carbon-carbon double bond. These monovalent substituent groups $R^4$ and $R^5$ may be the same or different and may form a ring structure with the atom in the molecule. The ring structure is preferably an alicyclic hydrocarbon structure. The monovalent organic groups $R^4$ and $R^5$ are exemplified as follows.

Examples of the acyclic alkyl group as $R^4$, $R^5$ are those having 1 to 30 carbon atoms, preferably 1 to 12 carbon atoms, such as methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl and i-propyl.

The substituted acyclic alkyl group as $R^4$, $R^5$ can be any of those obtained by substitution of one or two or more hydrogen atoms of the alkyl group with a $C_3$-$C_{20}$ alicyclic hydrocarbon group, a $C_1$-$C_4$ alkoxyl group, a halogen atom, an acyl group, an acyloxy group, a cyano group, a hydroxyl group, a carboxy group, an alkoxycarbonyl group or a nitro group. Examples of the alicyclic hydrocarbon-substituted alkyl group are cyclobutylmethyl, cyclopentylmethyl, cyclohexylmethyl, cycloheptylmethyl, cyclooctylmethyl, norbornylmethyl, adamantylmethyl and those obtained by substitution of hydrogen atoms on ring carbons of these substituted alkyl groups with either a methyl group, an ethyl group or a hydroxyl group. Examples of the fluorine-substituted alkyl group i.e. fluoroalkyl group are lower fluoroalkyl groups such as trifluoromethyl, pentafluoroethyl, 2,2,2-trifluoroethyl, n-heptafluoroethyl, 2,2,3,3,3-pentafluoropropyl, 3,3,3-trifluoropropyl and hexafluoroisopropyl.

When $R^4$, $R^5$ is an alicyclic hydrocarbon group or when $R^4$ and $R^5$ form an alicyclic hydrocarbon group with the carbon atom to which $R^4$ and $R^5$ are bonded, the alicyclic hydrocarbon group can be either monocyclic or polycyclic. More specifically, the alicyclic hydrocarbon group can be any of those having a monocyclo, bicycle, tricycle or tetracyclo structure of 3 or more carbon atoms, preferably 3 to 30 carbon atoms, more preferably 3 to 25 carbon atoms. Further, the alicyclic hydrocarbon group may have a substituent.

Examples of the monovalent monocyclic alicyclic hydrocarbon group are those preferably having 3 to 12 ring carbons, more preferably 3 to 7 ring carbons, such as cyclopropyl, cyclobutyl, cyclopentyl, cyclohexyl, cycloheptyl, cyclooctyl, cyclodecanyl, cyclododecanyl and 4-tert-butylcyclohexyl. Examples of the monovalent polycyclic alicyclic hydrocarbon group are those having 7 to 15 ring carbons, such as adamantyl, noradamantyl, decalin residue, tricyclodecanyl, tetracyclododecanyl, norbornyl and cedrol. The alicyclic hydrocarbon group may be a spiro ring. Examples of the spiro ring are those preferably having 3 to 6 carbon atoms, such as adamantyl, decalin residue, norbornyl, cedrol, cyclohexyl, cycloheptyl, cyclooctyl, cyclodecanyl, cyclododecanyl and tricyclodecanyl. One or two or more hydrogen atoms on the linking group or the ring carbon(s) of the above organic group may be each independently substituted with a substituent such as a $C_1$-$C_{30}$ alkyl group or substituted alkyl group, a hydroxyl group, an alkoxyl group, a carboxyl group or alkoxycarbonyl group. Further, one or two or more hydrogen atoms in this substituent group may be substituted with a fluorine atom or a trifluoromethyl group.

The $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxyl group, a halogen atom and an alkoxyl group. The alkoxyl group is exemplified by those of 1 to 4 carbon atoms, such as methoxy, ethoxy, propoxy and butoxy. The alkoxycarbonyl group exemplified by methoxycarbonyl, ethoxycarbonyl and isopropoxycarbony.

Examples of the alkoxyl group as $R^4$, $R^5$ are those having 1 to 4 carbon atoms, such as methoxy, ethoxy, propoxy and butoxy.

As the substituted or unsubstituted aryl group as $R^4$, $R^5$, there can be used those having 1 to 30 carbon atoms. The aryl group, when it is monocyclic, preferably has 3 to 12 ring carbons, more preferably 3 to 6 ring carbons. Examples of the substituted or unsubstituted aryl group are phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of the substituted or unsubstituted $C_1$-$C_{30}$ condensed polycyclic aromatic group are monovalent organic groups obtained by elimination of one hydrogen atom from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene etc. Preferably, one or two or more hydrogen atoms of each of these monovalent organic groups are each independently substituted with a fluorine atom, a $C_1$-$C_4$ alkyl group or fluorine-containing alkyl group.

Examples of the monocyclic or polycyclic heterocyclic group are those having 3 to 25 ring carbons, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One or two or more hydrogen atoms on the ring structure of each of these heterocyclic groups may be each independently substituted with an alkyl group, an alicyclic hydrocarbon group, an aryl group or a heterocyclic group. Among others, preferred are those having a monocyclic or polycyclic ether ring or lactone ring as exemplified as follows.

[Chem. 12]

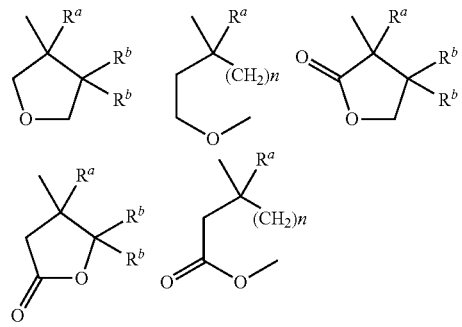

In the above formulas, $R^a$ and $R^b$ each independently represent a hydrogen atom or a $C_1$-$C_4$ alkyl group; and n represents an integer of 2 to 4.

The divalent alicyclic hydrocarbon group constituting the main skeleton of the linking group $W^1$ can be either monocyclic or polycyclic. More specifically, the divalent alicyclic hydrocarbon group can be any of those having a monocyclo, bicycle, tricycle or tetracyclo structure of 3 or more carbon atoms, preferably 3 to 30 carbon atoms, more preferably 3 to 25 carbon atoms. The divalent alicyclic hydrocarbon group may have a substituent.

Examples of the divalent monocyclic alicyclic hydrocarbon group are those preferably having 3 to 12 ring carbons, more preferably 3 to 7 ring carbons, such as cyclopropylene, cyclobutylene, cyclopentylene, cyclohexylene, cycloheptylene, cyclooctylene, cyclodecanylene, cyclododecanylene and 4-tert-butylcyclohexylene. Examples of the divalent polycyclic alicyclic hydrocarbon group are those having 7 to 15 ring carbons, such as adamantylene, noradamantylene, divalent decalin residue, tricyclodecanylene, tetracyclododecanylene, norbornylene and divalent cedrol residue. The alicyclic hydrocarbon group may be a spiro ring preferably having 3 to 6 carbon atoms. As in the case of the above-explained $R^4$, $R^5$, one or two or more hydrogen atoms on the linking group or the ring carbon(s) of the above organic group may be each independently substituted with a substituent such as a $C_1$-$C_{30}$ alkyl group or substituted alkyl group, a hydroxyl group, an alkoxyl group, a carboxyl group or an alkoxycarbonyl group; and one or two or more hydrogen atoms in this substituent group may further be substituted with a fluorine atom or a trifluoromethyl group.

The $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxyl group, a halogen atom and an alkoxyl group. The alkoxyl group is exemplified by those of 1 to 4 carbon atoms, such as methoxy, ethoxy, propoxy and butoxy. The alkoxycarbonyl group exemplified by methoxycarbonyl, ethoxycarbonyl and isopropoxycarbony.

The divalent aromatic hydrocarbon group constituting the main skeleton of the linking group $W^1$ is of 1 to 30 carbon atoms. The divalent aromatic hydrocarbon group, when it is monocyclic, preferably has 3 to 12 ring carbons, more preferably 3 to 6 ring carbons. Examples of the divalent aromatic hydrocarbon group are divalent groups obtained by elimination of two hydrogen atoms from benzene, biphenyl, terphenyl, toluene, phenol, anisole, mesitylene, cumene, 2,3-xylylene, 2,4-xylene, 2,5-xylene, 2,6-xylene, 3,4-xylene, 3,5-xylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene etc.

The substituted or unsubstituted condensed polycyclic aromatic group constituting the main skeleton of the linking group $W^1$ is preferably of 1 to 30 carbon atoms. Examples of the substituted or unsubstituted condensed polycyclic aromatic group are divalent organic groups obtained by elimination of two hydrogen atoms from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene etc. One or two or more hydrogen atoms of each of these divalent organic groups may be each independently substituted with a fluorine atom, a $C_1$-$C_4$ alkyl group or fluorine-containing alkyl group.

The divalent heterocyclic group constituting the main skeleton of the linking group $W^1$ is a monocyclic or polycyclic heterocyclic group of 3 to 25 ring carbons. Examples of the divalent heterocyclic group are divalent organic groups obtained by elimination of two hydrogen atoms from pyridine, furan, thienine, pyranine, pyrroline, thianthrene, pyrazon, isothiazone, isooxazone, pyrazine, pyrimidine, pyridazine, tetrahydropyranine, tetrahydrofuranine, tetrahydrothiopyranine, tetrahydrothiofuranine etc. One or two or more hydrogen atoms on the ring atom each of these divalent organic groups may be each independently substituted with an alkyl group (preferably, a lower alkyl group), an alicyclic hydrocarbon group, an aryl group or a heterocyclic group. Among others, monocyclic or polycyclic ether ring groups are preferred. The following are examples of the monocyclic or polycyclic ether ring groups.

[Chem. 13]

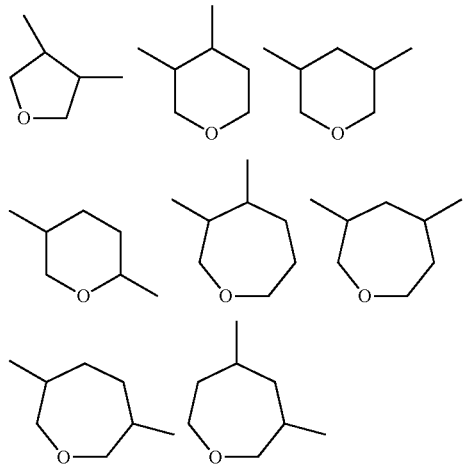

As mentioned above, the divalent linking group $W^1$ may formed by combinations of any of the divalent groups explained above by the general formula or specifically exemplified above.

As the linking group $W^1$, the substituted methylene group of the general formula (3) is most preferred. Preferable specific examples of the substituted methylene group of the general formula (3) are listed as follows. In the following formulas, O and C indicate an oxygen atom and a carbon atom located adjacent to the substituted methylene group.

[Chem. 14]

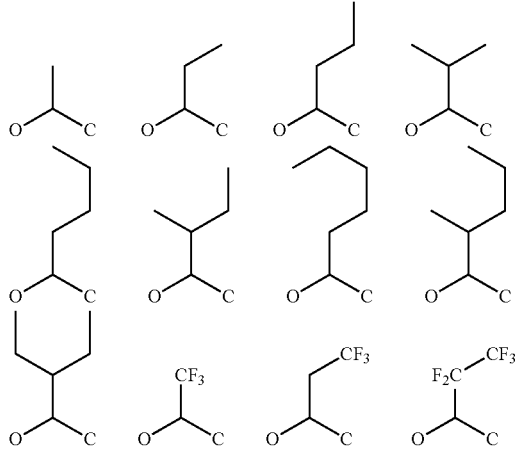

-continued

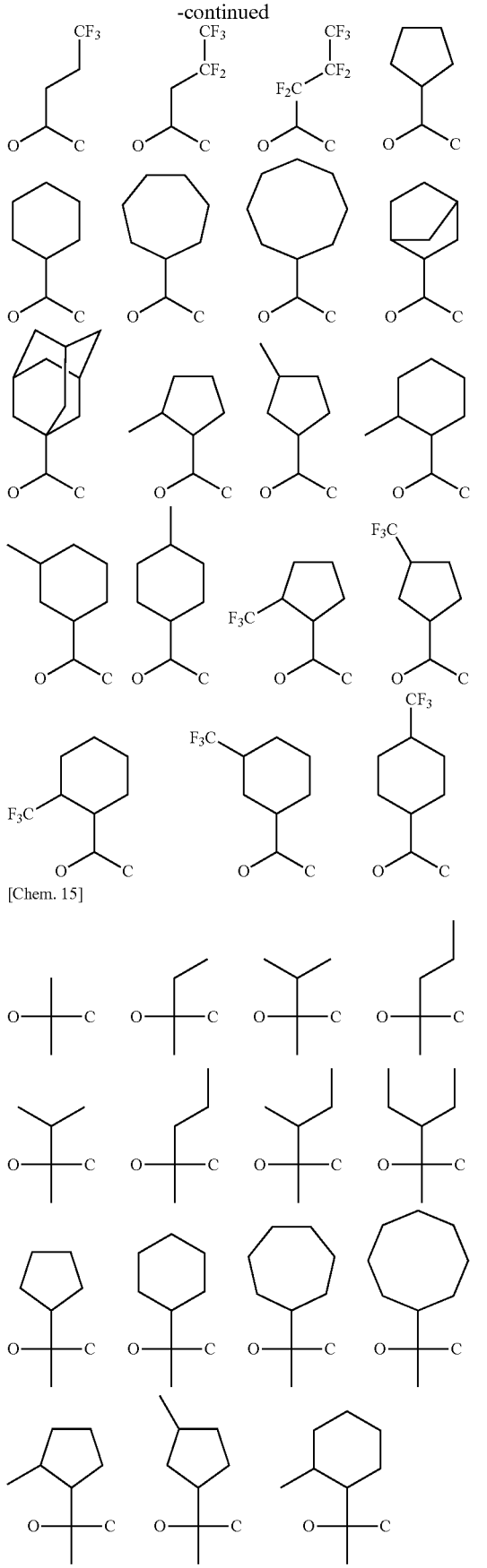
[Chem. 15]

-continued

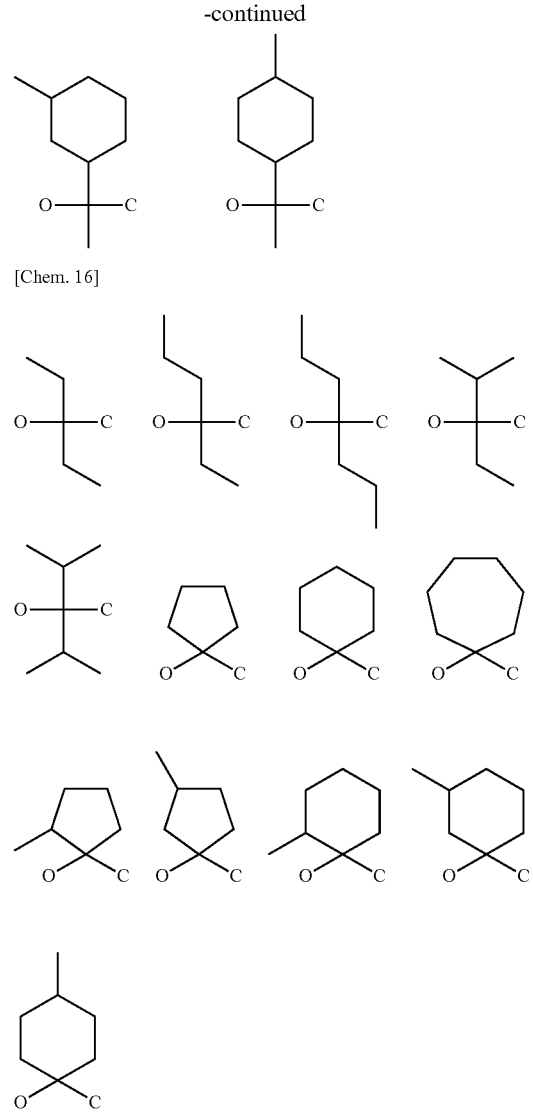
[Chem. 16]

In the general formula (1), the monovalent organic group $R^3$ is selected depending on the purposes of use of the fluorine-containing unsaturated carboxylic acid ester and polymer thereof. In the present invention, the water repellency of a resist composition or a top coat composition prepared from the polymer of the fluorine-containing unsaturated carboxylic acid ester of the general formula (1) is very important. A fluorine-containing organic group, with which water repellency can be improved, is thus favorable to $R^3$. On the other hand, it is unfavorably difficult to design the photosensitivity of the resist composition if a difluorocarboxylic acid having water solubility is formed by cleavage of an ester bond under the direct action of high energy ray etc. or the light amplification action of a photoacid generator. Further, it is unfavorable that the ester for use in the top coat composition has photosensitivity as the top coat composition becomes unstable. Thus, the ester bond relating to $R^3$ is preferably stable to an acid generated from the photoacid generator. Namely, an acid-labile protecting group for an acid-labile tertiary ester is not herein preferred as the organic group of the ester. The organic group of the ester is preferably a primary or secondary organic group.

More specifically, $R^3$ is an alkyl group of the general formula (4) or an aryl group (aromatic hydrocarbon group).

[Chem. 17]

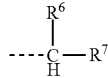

(4)

In the general formula (4), $R^6$ and $R^7$ are each independently a hydrogen atom, a substituted or unsubstituted alkyl or aryl group. $R^6$, $R^7$ and carbon in the formula may be bonded together to form an alicyclic hydrocarbon group. Any number of hydrogen atoms in $R^3$ i.e. in the alkyl group of the general formula (4) or the aryl group (aromatic hydrocarbon group) may be substituted with a halogen atom, a hydroxyl group, an alkyl group, a fluorine-containing alkyl group or an aryl group. Any methylene group ($CH_2$) in $R^3$ (except for that containing the carbon atom represented by C in the general formula (4)) may be replaced by a carbonyl group (C=O), an ether group (O), an imide group (NH), a thioether group (S), a sulfinyl group (SO) or a sulfonyl group ($SO_2$). Herein, $R^3$ is not an ethyl group.

The alkyl group as $R^6$, $R^7$ is a straight, branched or cyclic alkyl group of 1 to 20 carbon atoms, preferably 4 to 20 carbon atoms.

Examples of the straight or branched alkyl group as $R^6$, $R^7$ are methyl, ethyl, n-propyl, i-propyl, n-butyl, n-pentyl, i-pentyl, n-hexyl, i-hexyl, n-heptyl, n-octyl, i-octyl, n-nonyl, n-decyl and n-dodecyl. A hydrogen atom or atoms in the alkyl group $R^6$, $R^7$ may be substituted with a halogen atom, a hydroxyl group, an alkyl group, a fluorine-containing alkyl group or an aryl group, preferably a fluorine atom, an alkyl group or a fluoroalkyl group. Examples of the fluorine-substituted alkyl group as $R^6$, $R^7$ are trifluoromethyl, perfluoroethyl, perfluoropropyl, perfluoroisopropyl, perfluorobutyl, perfluoropentyl, perfluorohexyl, perfluoroheptyl, perfluorooctyl, 2,2-difluoroethyl, 3,3,3-trifluoroethyl, 1,1,1,3,3,3-hexafluoroisopropyl, 1H,1H-hentafluoro-1-propyl, 1H,1H-heptafluoro-1-butyl, 2,2,3,4,4,4-hexafluoro-1-butyl, 1H,1H,5H-octafluoro-1-pentyl, 1H,1H-nonafluoro-1-pentyl, 1H,1H-perfluoro-1-hexyl and 1H,1H-perfluoro-1-heptyl. Examples of the alkyl-substituted alkyl group i.e. branched alkyl group as $R^6$, $R^7$ are 1-methylpropyl, 2-methylpropyl, 1-methylbutyl, 2-methylbutyl, 3-methylbutyl, 1-ethylbutyl, 2-ethylbutyl, 1-methylpentyl, 2-methylpentyl, 3-methylpentyl, 4-methylpentyl, 1-ethylpentyl, 2-ethylpentyl, 3-ethylpentyl, 1-propylpentyl, 1-methylhexyl, 2-methylhexyl, 3-methylhexyl, 4-methylhexyl, 5-methylhexyl, 1-ethylhexyl, 2-ethylhexyl, 3-ethylhexyl, 1-propylhexyl, 2-propylhexyl, 3-propylhexyl, 1-methylheptyl, 2-methylheptyl, 3-methylheptyl, 4-methylheptyl, 5-methylheptyl, 6-methylheptyl, 1-ethylheptyl, 2-ethylheptyl, 3-ethylheptyl, 4-ethylheptyl, 5-ethylheptyl, 1-propylheptyl, 2-propylheptyl, 3-propylheptyl, 4-propylheptyl, 1-methyloctyl, 2-methyloctyl, 3-methyloctyl, 4-methyloctyl, 5-methyloctyl, 6-methyloctyl, 7-methyloctyl, 1-ethyloctyl, 2-ethyloctyl, 3-ethyloctyl, 4-ethyloctyl, 5-ethyloctyl, 6-ethyloctyl, 1-propyloctyl, 2-propyloctyl, 3-propyloctyl, 4-propyloctyl and 1-butyloctyl. Examples of the cycloalkyl-substituted alkyl group as $R^6$, $R^7$ are cyclopropylmethyl, cyclobutylmethyl, cyclopentylmethyl, cyclohexylmethyl, cycloheptylmethyl, cyclooctylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl, 2-cyclohexylethyl, 1-cycloheptylethyl, 2-cycloheptylethyl, 1-cyclooctylethyl, 2-cyclooctylethyl, bornylmethyl, norbornylmethyl, 2-adamantylmethyl and octahydro-4,7-methano-1H-5-indenemethyl. Examples of the aryl-substituted alkyl group as $R^6$, $R^7$ are benzyl, 2-methylphenylmethyl, 3-methylphenylmethyl, 4-methylphenylmethyl, 2,4-dimethylphenylmethyl, 3,5-dimethylphenylmethyl, 2-fluoromethylphenylmethyl, 3-fluoromethylphenylmethyl, 4-fluoromethylphenylmethyl, 2,4-bisfluorophenylmethyl, 3,5-bisfluorophenylmethyl, 2-trifluoromethylphenylmethyl, 3-trifluoromethylphenylmethyl, 4-trifluoromethylphenylmethyl, 2,4-bisfluoromethylphenylmethyl, 3,5-bisfluoromethylphenylmethyl, 1-naphthylmethyl, 2-naphthylmethyl, perfluoro-1-naphthylmethyl and perfluoro-2-naphthylmethyl.

Examples of the cyclic alkyl group as $R^6$, $R^7$ are those preferably having 3 to 20 carbon atoms, such as cyclopropyl, cyclobutyl, cyclopentyl, cyclohexyl, cycloheptyl, cyclooctyl, bornyl, norbornyl, 2-adamantyl and indene. These cyclic alkyl groups may each have a substituent as mentioned above. Examples of the substituted cyclic alkyl group are 2-methylcyclopentyl, 3-methylcyclopentyl, 2-fluorocyclopentyl, 3-fluorocyclopentyl, 2-trifluoromethylcyclopentyl, 3-trifluoromethylcyclopentyl, 2-methylcyclohexyl, 3-methylcyclohexyl, 4-methylcyclohexyl, 2,4-dimethylcyclohexyl, 3,5-dimethylcyclohexyl, 2-fluorocyclohexyl, 3-fluorocyclohexyl, 4-fluorocyclohexyl, 2,4-difluorocyclohexyl, 3,5-difluorocyclohexyl, 2-trifluoromethylcyclohexyl, 3-trifluoromethylcyclohexyl, 4-trifluoromethylcyclohexyl, 2,4-bistrifluoromethylcyclohexyl, 3,5-bistrifluoromethylcyclohexyl, 2-methylcycloheptyl, 3-methylcycloheptyl, 4-methylcycloheptyl, 2-fluorocycloheptyl, 3-fluorocycloheptyl, 4-fluorocycloheptyl, 2-trifluoromethylcycloheptyl, 3-trifluoromethylcycloheptyl, 4-trifluoromethylcycloheptyl, bornyl, norbornyl, 1-adamantyl, 2-adamantyl, octahydro-4,7-methano-1H-5-indene, 2,4-bis(1,1,1,3,3,3-hexafluoro-2-hydroxypropyl)cyclohexyl, 3,5-bis(1,1,1,3,3,3-hexafluoro-2-hydroxypropyl)cyclohexyl and 1,1,2,2,3,3,3a,7a-octafluorooctahydro-4,7-methano-1H-5-indene.

Examples of the aryl group as $R^6$, $R^7$ are those preferably having 3 to 20 carbon atoms, such as phenyl, 1-naphthyl, 2-naphthyl, 1-anthryl, 1-phenanthryl, o-tosyl, m-tosyl, p-tosyl, 3,5-xylyl, 2,4-xylyl and mesityl. Examples of the fluorine-containing aryl group are those obtained by substitution of a hydrogen atom or atoms of the aryl group with a fluorine atom, such as 4-fluorophenyl, 3-fluorophenyl, 2-fluorophenyl, 2,4-difluorophenyl, 3,5-difluorophenyl, 2,3,4,5,6-pentafluorophenyl, perfluoro-1-naphthyl, perfluoro-2-naphthyl, 2-(trifluoromethyl)phenyl, 3-(trifluoromethyl)phenyl, 4-(trifluoromethyl)phenyl, 3,5-bis(trifluoromethyl)phenyl and 2,4-bis(trifluoromethyl)phenyl.

As mentioned above, $R^6$, $R^7$ and the carbon atom in the general formula (4) may be bonded into a ring to thereby form an alicyclic hydrocarbon group. This alicyclic hydrocarbon group may have a substituent. Examples of such an alicyclic hydrocarbon group are cyclopropyl, cyclobutyl, cyclopentyl, cyclohexyl, cycloheptyl, cyclooctyl, 2-methylcyclopentyl, 3-methylcyclopentyl, 2-fluorocyclopentyl, 3-fluorocyclopentyl, 2-trifluoromethylcyclopentyl, 3-trifluoromethylcyclopentyl, 2-methylcyclohexyl, 3-methylcyclohexyl, 4-methylcyclohexyl, 2,4-dimethylcyclohexyl, 3,5-dimethylcyclohexyl, 2-fluorocyclohexyl, 3-fluorocyclohexyl, 4-fluorocyclohexyl, 2,4-difluorocyclohexyl, 3,5-difluorocyclohexyl, 2-trifluoromethylcyclohexyl, 3-trifluoromethylcyclohexyl, 4-trifluoromethylcyclohexyl, 2,4-bistrifluoromethylcyclohexyl, 3,5-bistrifluoromethylcyclohexyl, 2-methylcycloheptyl, 3-methylcycloheptyl, 4-methylcycloheptyl, 2-fluorocycloheptyl, 3-fluorocycloheptyl, 4-fluorocycloheptyl, 2-trifluoromethylcycloheptyl, 3-trifluoromethylcycloheptyl, 4-trifluoromethylcycloheptyl, bornyl, norbornyl, 1-adamantyl, methyl-1-adamantyl, hydroxyl-1-adamantyl, 2-adamantyl, methyl-2-adamantyl, hydroxyl-2-adamantyl, octahydro-4,7-methano-1H-5-indene, 2,4-bis(1,1,1,3,3,3-hexafluoro-2-hydroxypropyecyclohexyl, 3,5-bis(1,1,1,3,3,3-hexafluoro-2-hydroxypropyl)cyclohexyl and 1,1,2,2,3,3,3a,7a-octafluorooctahydro-4,7-methano-1H-5-indene.

The aromatic hydrocarbon group as $R^3$ is an aryl group of 3 to 20 carbon atoms. Examples of the $C_3$-$C_{20}$ aryl group are phenyl, 1-naphthyl, 2-naphthyl, 1-anthryl, 1-phenanthryl, o-tosyl, m-tosyl, p-tosyl, 3,5-xylyl, 2,4-xylyl and mesityl.

Examples of the fluorine-substituted $C_3$-$C_{20}$ aryl group i.e. fluorine-containing $C_3$-$C_{20}$ aryl group are 4-fluorophenyl, 3-fluorophenyl, 2-fluorophenyl, 3,5-difluorophenyl, 2,3,4,5,6-pentafluorophenyl, perfluoro-1-naphthyl, perfluoro-2-naphthyl, 2-(trifluoromethyl)phenyl, 3-(trifluoromethyl)phenyl, 4-(trifluoromethyl)phenyl, 3,5-bis(trifluoromethyl)phenyl and 2,4-bis(trifluoromethyl)phenyl.

Any hydrogen atom or atoms on $R^3$ (except for that on the carbon atom bonded to (C=O)O group) may be substituted with a halogen atom other than fluorine, a hydroxyl group, a $C_1$-$C_{20}$ straight, branched or cyclic alkyl or fluorine-containing alkyl group or a $C_3$-$C_{20}$ aryl or fluorine-containing aryl group. Further, any methylene group (CH$_2$) in $R^3$ (except for that containing the carbon atom represented by C in the general formula (4)) may be replaced by C=O, O, NH, S, SO or SO$_2$. These substituent groups can exist in any number within a structurally possible range.

The following are preferred examples of the structure in which any number of hydrogen atoms in $R^3$ is substituted with fluorine, hydroxyl, alkyl, fluorine-containing alkyl or aryl or the structure in which methylene group (CH$_2$) in $R^3$ is replaced by C=O, O, NH, S, SO or SO$_2$ in addition to the above-mentioned group $R^3$. In the formulas, the dotted line indicates a bonding position.

[Chem. 18]

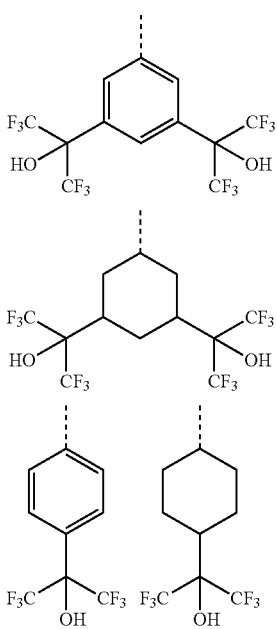

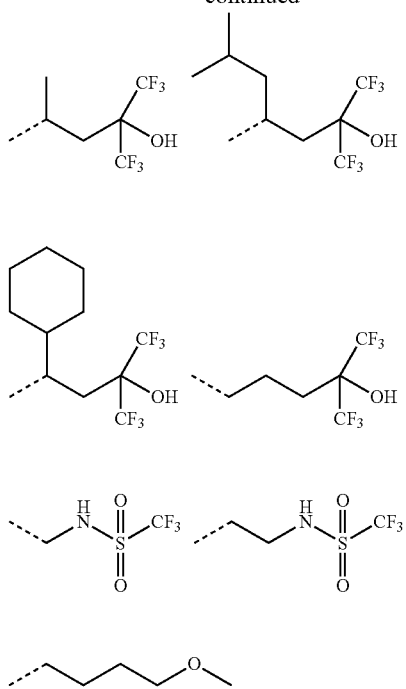

There can also be used as $R^3$ a monocyclic or polycyclic lactone group obtained by replacement of a methylene group (—CH$_2$—) of the above-mentioned cyclic structure by an oxygen atom (ether group) and a carbonyl group. Examples of the monocyclic or polycyclic lactone group are γ-butyrolactone, γ-valerolactone, angelicalactone, γ-hexalactone, γ-heptalactone, γ-octalactone, γ-nonalactone, 3-methyl-4-octanolide (whisky lactone), γ-decalactone, γ-undecalactone, γ-dodecalactone, γ-jasmolactone (7-decenolactone), δ-hexalactone, 4,6,6(4,4,6)-trimethyltetrahydropyrane-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasmine lactone, cis-jasmone lactone, methyl-γ-decalactone and those indicated below. In the formulas, the dotted line indicates a bonding position.

[Chem. 19]

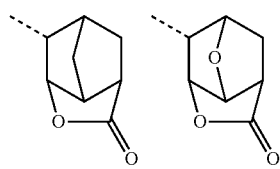

[Production Process of Fluorine-Containing Unsaturated Carboxylic Acid Ester]

There is no particular limitation on the production process of the fluorine-containing unsaturated carboxylic acid ester of the general formula (1) in the present invention. For example, the target fluorine-containing unsaturated carboxylic acid ester can be produced through the following reaction formulas [1] to [5].

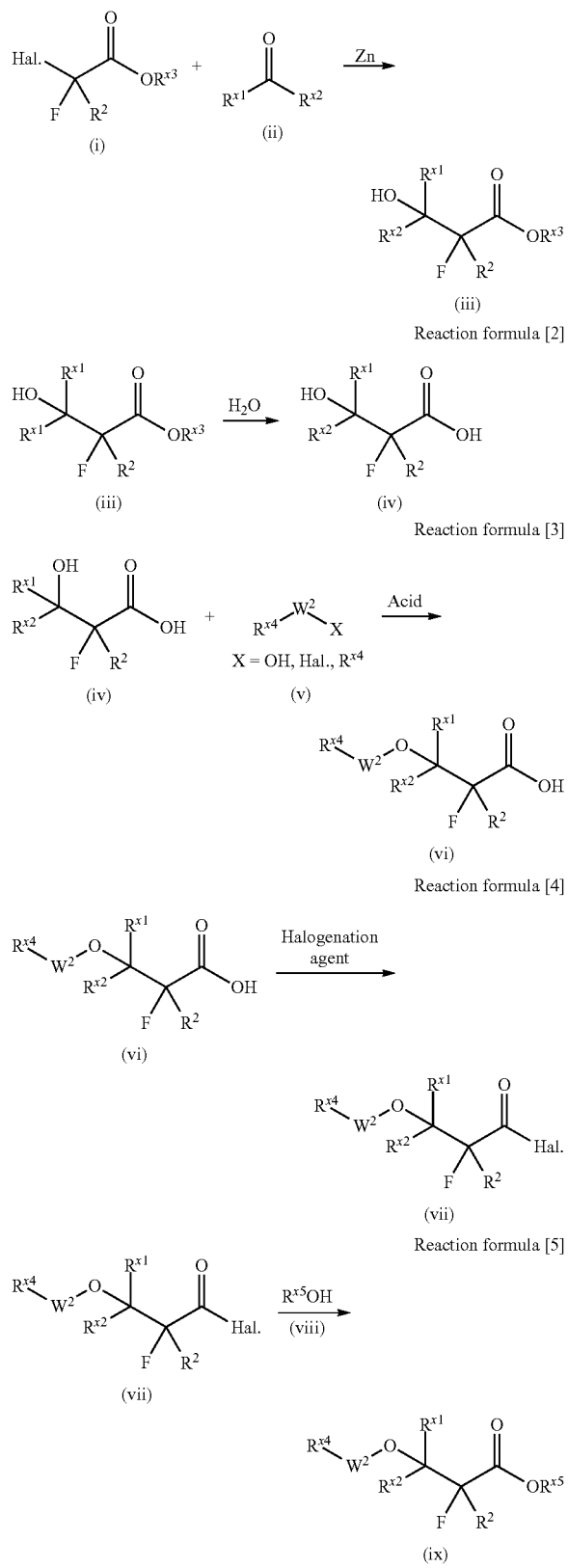

In the reaction formulas [1] to [5], $R^{X4}$—$W^2$—O— and $R^2$ have the same definitions as $R^0$ and $R^2$ in the general formula (1), respectively; and $R^{X1}$, $R^{X2}$ and $R^{X3}$ each independently represent a monovalent organic group, where $R^{X1}$ may be a hydrogen atom. $R^{X1}$ and $R^{X2}$ correspond to $R^4$ and $R^5$ with the proviso that, in the general formula (1), $W^1$ is the substituted methylene group of the general formula (3). The specific definitions of $R^4$ and $R^5$ can be thus also applied to $R^{X1}$ and $R^{X2}$. Preferably, $R^{X1}$ and $R^{X2}$ are lower alkyl groups. Examples of the lower alkyl groups as $R^{X1}$, $R^{X2}$ are methyl, ethyl, propyl, butyl, cyclopentyl, norbornyl, adamantyl and those obtained by hydrogen atoms of these alkyl groups with a fluorine atom, such as trifluoromethyl, 2,2,2-trifluoroethyl, 1-(trifluoromethyl)ethyl and 3,3,3-trifluoropropyl. $R^{X1}$ and $R^{X2}$ may be bonded together to form a cyclic group such as cyclopentyl, cyclohexyl or cycloheptyl. $R^{X3}$ serves as an ester protecting group. Further, $R^{X5}$ corresponds to a specific example of $R^3$ in the general formula (1). $W^2$ represents a divalent linking group. $W^2$—O—$CR^{X1}R^{X2}$ corresponds to one example of $W^1$ in the general formula (1).

The respective reaction steps will be explained below.

In the reaction formula [1], a halogen-containing carboxylic acid ester (i) having at least one fluorine atom and at least one halogen atom (other than fluorine atom) in α-position is reacted with a carbonyl compound (ii) in the presence of zinc in an anhydrous state, thereby forming a hydroxycarboxylic acid ester (iii). (This reaction is called Reformatsky reaction.)

In the reaction formula [2], the hydroxycarboxylic acid ester (iii) obtained in the reaction formula [1] is hydrolyzed to a hydroxycarboxylic acid (iv).

In the reaction formula [3], the hydroxycarboxylic acid (iv) obtained in the reaction formula [2] is reacted with a polymerizable double bond-containing carboxylic acid, carboxylic acid anhydride or carboxylic acid halide (v), thereby forming an unsaturated carboxylic acid (vi).

In the reaction formula [4], the unsaturated carboxylic acid (vi) obtained in the reaction formula [3] is halogenated to an unsaturated carboxylic acid halide (vii) with the use of a halogenating agent such as thionyl chloride.

In the reaction formula [5], the fluorine-containing unsaturated carboxylic acid ester is formed by reaction of the unsaturated carboxylic acid halide (vii) obtained in the reaction formula [4] with an alcohol (viii).

In each of the reaction formulas [1] and [3], there can be used any organic solvent as long as the organic solvent is not involved in the reaction under the respective reaction conditions. Examples of the organic solvent are: aliphatic hydrocarbons such as pentane, hexane and heptanes; aromatic hydrocarbons such as benzene, toluene and xylene; nitriles such as acetonitrile, propionitrile, phenylacetonitrile, isobutyronitrile and benzonitrile; acid amides such as dimethylformamide, dimethylacetoamide, methylformamide, formamide and hexamethylphosphoric triamide; and lower ethers such as tetrahydrofuran, 1,2-dimethoxyethane, 1,4-dioxane, diethyl ether, 1,2-epoxyethane, dibutyl ether, tert-butyl methyl ether and substituted tetrahydrofuran. Among others, tetrahydrofuran and dimethylformamide are preferred. These solvents can be used solely or in combination of two or more thereof. The organic solve used is not however limited to these solvents. The amount of the organic solvent used is of the order of 1 to 100 parts by mass, preferably 1 to 10 parts by mass, per 1 part by mass of the starting material. In the reaction formula [1], it is desirable to remove as much water as possible from the organic solvent. The water content of the organic solvent is preferably 50 ppm or lower.

In the reaction formula [3], the water is not necessarily completely removed from the organic solvent although it is desirable to remove as much water as possible from the organic solvent. There would be no problem when the water content of the organic solvent is equivalent to that of industrially variable organic solvents. The organic solvent can be used as it is without being dehydrated.

The zinc is preferably activated by any known process and then used in the reaction formula [1]. As the zinc activation process, it is feasible to obtain zinc metal by reduction of a zinc salt such as zinc chloride with a potassium, magnesium, lithium etc., to activate zinc metal by treatment with hydrochloric acid, to treat zinc metal with a copper salt or silver salt in acetic acid and thereby alloy zinc with copper or silver, to activate zinc by ultrasonic treatment, to stir zinc together with chlorotrimethylsilane in an ether, or to bring zinc into contact with a copper compound and chlorotrimethylsilane in an aprotic organic solvent.

The zinc can be in any form such as powder form, particle form, massive form, porous form, abatement form or linear form. The reaction temperature is of the order of −78 to 120° C. Although the reaction time varies depending on the kind of the reaction agent used, it is generally convenient to conduct the reaction for about 10 minutes to 20 hours. The reaction pressure can be set to or around an atmospheric pressure level. The other reaction conditions can be set with reference to those of known similar reaction using zinc metal by a person skilled in the art.

In the reaction formula [2], the hydrolysis is performed by water in the presence of a base. As the base, there can be used organic bases: such as trimethylamine, triethylamine, diisopropylethylamine, tri-n-propylamine, tri-n-butylamine, dimethyllaurylamine, dimethylaminopyridine, N,N-dimethylaniline, dimethylbenzylamine, 1,8-diazabicyclo[5.4.0]undec-7-ene, 1,4-diazabicyclo[2.2.2]octane, pyridine, 3,5-lutidine, 2,6-lutidine, 2,4-lutidine, 2,5-lutidine and 3,4-lutidine; and inorganic bases such as sodium hydroxide, potassium hydroxide, sodium carbonate and calcium hydroxide.

It suffices to use the base in an amount of 1 mol or more per 1 mol of the reaction substrate in the reaction formula [2]. The amount of the base used is generally preferably 1 to 10 mol, more preferably 1 to 5 mol, per 1 mol of the reaction substrate.

In each of the reaction formulas [2] to [5], it is also generally convenient to conduct the reaction for about 10 minutes to 20 hours although the reaction time varies depending on the kind of the reaction agent used. The reaction pressure can be set to or around an atmospheric pressure level. The other reaction conditions can be set with reference to those of known similar reaction by a person skilled in the art.

In the reaction formula [3], the amount of the polymerizable double bond-containing carboxylic acid, carboxylic acid anhydride or carboxylic acid halide (v) used is generally 0.8 to 5 mol, preferably 1 to 3 mol, more preferably 1 to 2 mol, per 1 mol of the reaction substrate.

Further, an acid may be used as a catalyst in the reaction formula [3]. As the acid, there can be used hydrochloric acid, methanesulfonic acid, trifluoromethanesulfonic acid and trifluoroacetic acid. Among others, methanesulfonic acid and trifluoromethanesulfonic acid are preferred.

It suffices to use the acid in an amount of 1 mol or less per 1 mol of the reaction substrate in the reaction formula [3]. The amount of the acid used is generally preferably 0.1 to 1 mol, more preferably 0.1 to 0.5 mol, per 1 mol of the reaction substrate.

In the reaction formula [4], the halogenating agent used is one kind or a mixture of two or more kinds selected from halogenating agents such as thionyl halide, oxalyl halogenide, phosphorus trihalide, phosphorus pentahalide, phosphorous oxyhalide, carbonyl halide and trihalomethyl haloformate. When the halogen is chlorine, there can be used chlorinating agents such as thionyl chloride, sulfuryl chloride, phosphorous trichloride, phosphorous pentachloride, oxalyl chloride. Among others, thionyl chloride and phosphorous trichloride are preferred.

It suffices to use the halogenating agent in an amount of 1 mol or more per 1 mol of the reaction substrate in the reaction formula [4]. The amount of the halogenating agent used is generally preferably 1 to 10 mol, more preferably 1 to 5 mol, per 1 mol of the reaction substrate.

In the reaction formula [5], it suffices to use the alcohol in an amount of 1 mol or more per 1 mol of the reaction substrate. The amount of the alcohol used is generally preferably 1 to 10 mol, more preferably 1 to 5 mol, per 1 mol of the reaction substrate.

In the reaction formula [5], the alcohol (viii) has $R^{X5}$ corresponding to $R^3$ of the general formula [1] and thus has such a structure that a hydroxyl group is bonded to any of the substituent groups exemplified above as $R^3$. Specific examples of the alcohol are n-butyl alcohol, n-pentyl alcohol, i-pentyl alcohol, n-hexyl alcohol, i-hexyl alcohol, n-heptyl alcohol, n-octyl alcohol, i-octyl alcohol, n-nonyl alcohol, n-decyl alcohol, 2-ethylhexyl alcohol, n-dodecyl alcohol, cyclobutyl alcohol, cyclopentyl alcohol, cyclohexyl alcohol, borneol, norborneol, 2-adamantanol, bornylmethanol, norbornylmethanol, adamantanemethanol, octahydro-4,7-methano-1H-indene-5-ol, 2,2-difluoroethyl alcohol, trifluoroethyl alcohol, hexafluoroisopropyl alcohol, 1H,1H-pentafluoro-1-propyl alcohol, 1H,1H-heptafluoro-1-butyl alcohol, 2,2,3,4,4,4-hexafluoro-1-butyl alcohol, 1H,1H,5H-octafluoro-1-pentyl alcohol, 1H,1H-nonafluoro-1-pentyl alcohol, 1H,1H-perfluoro-1-hexyl alcohol, 1H,1H-perfluoro-1-heptyl alcohol, (perfluorocyclohexyl)methanol, (perfluoroadamantane)methanol, 1,3-bis(1,1,1,3,3,3-hexafluoro-2-hydroxypropyl)cyclohexyl alcohol, 1,1,2,2,3,3,3a,7a-octafluorooctahydro-4,7-methano-1H-indene-5-ol, phenol, 1-naphthyl alcohol, 2-naphthyl alcohol, 1-anthryl alcohol, 1-phenanthryl alcohol, o-tosyl alcohol, m-tosyl alcohol, p-tosyl alcohol, 3,5-xylyl alcohol, 2,4-xylyl alcohol, mesityl alcohol, benzyl alcohol, 4-fluorophenol, 3-fluorophenol, 2-fluorophenol, 3,5-difluorophenol, 2,3,4,5,6-pentafluorophenol, perfluoro-1-naphthyl alcohol, perfluoro-2-naphthyl alcohol, 2-(trifluoromethyl)phenol, 3-(trifluoromethyl)phenol, 4-(trifluoromethyl)phenol, 3,5-bis(trifluoromethyl)phenol, 2,4-bis(trifluoromethyl)phenol, 2,3,4,5,6-pentafluorobenzyl alcohol, hydroxy-γ-butyrolactone, hydroxy-γ-valerolactone, hydroxy-angelicalactone, hydroxy-γ-hexalactone, hydroxy-γ-heptalactone, hydroxy-γ-octalactone, hydroxy-γ-nonalactone, hydroxy-3-methyl-4-octanolide (hydroxy whisky lactone), hydroxy-γ-decalactone, hydroxy-γ-undecalactone, hydroxy-γ-dodecalactone, hydroxy-γ-jasmolactone (hydroxy-7-decenolactone), hydroxy-δ-hexalactone, hydroxy-4,6,6(4,4,6)-trimethyltetrahydropyrane-2-one, hydroxy-δ-octalactone, hydroxy-δ-nonalactone, hydroxy-δ-decalactone, hydroxy-δ-2-decenolactone, hydroxy-δ-undecalactone, hydroxy-δ-dodecalactone, hydroxy-δ-tridecalactone, hydroxy-δ-tetradecalactone, hydroxy-lactoscatone, hydroxy-ε-decalactone, hydroxy-ε-dodecalactone, hydroxycyclohexyllactone, hydroxy jasmine lactone, hydroxy cis-jasmone lactone, hydroxy-methyl-γ-decalactone and those indicated below.

[Chem. 21]

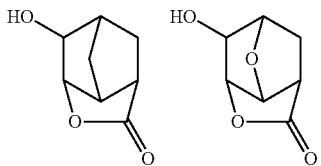

There can also be used the following compounds.

[Chem. 22]

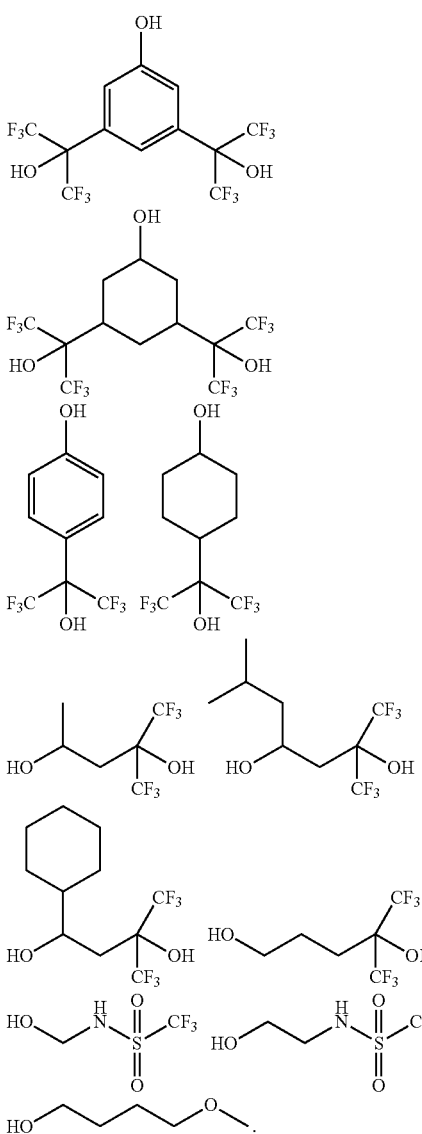

Purification operations such as washing, solvent separation and drying can be performed between the respective reaction steps of the reaction formulas [1] to [5].

[Fluorine-Containing Polymer]

The fluorine-containing polymer of the present invention has at least the repeating unit (a) of the general formula (2) as mentioned above.

[Chem. 23]

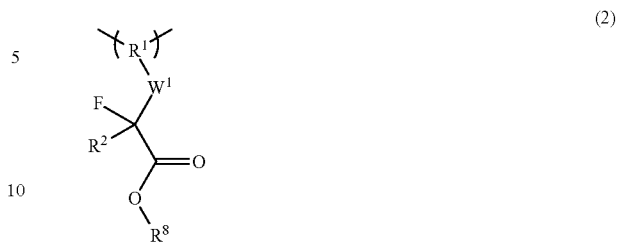

(2)

In the general formula (2), $R^1$ is either one of polymerizable double bond-containing groups of the following formulas.

[Chem. 24]

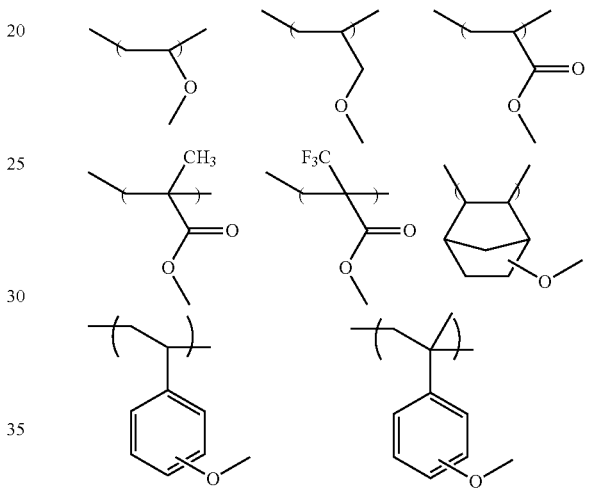

Further, $R^2$ is a fluorine atom or a fluorine-containing alkyl group; and $R^8$ is an alkyl group of the general formula (4) or an aryl group (aromatic hydrocarbon group).

[Chem. 25]

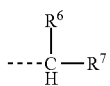

(4)

In the general formula (4), $R^6$ and $R^7$ are each independently a hydrogen atom, a substituted or unsubstituted alkyl or aryl group. $R^6$, $R^7$ and carbon in the formula may be bonded together to form an alicyclic hydrocarbon group. Any number of hydrogen atoms in $R^3$ i.e. the alkyl group of the general formula (4) or the aryl group (aromatic hydrocarbon group) may be substituted with a halogen atom, a hydroxyl group, an alkyl group, a fluorine-containing alkyl group or an aryl group. Any methylene group ($CH_2$) in $R^3$ (except for that containing the carbon atom represented by C in the general formula (4)) may be replaced by C=O, O, NH, S, SO or $SO_2$.

$W^1$ is a divalent linking group having a main skeleton formed by one atomic group, or two or more atomic groups in combination, selected from the group consisting of a single bond, substituted or unsubstituted methylene groups, divalent cyclic alkyl groups (alicyclic hydrocarbon groups), divalent aryl groups (aromatic hydrocarbon groups), substituted or unsubstituted condensed polycyclic aromatic groups, divalent heterocyclic groups, a carbonyl group, an ether group, an ester bond, an oxycarbonyl bond, a thioether group, an amide bond, a sulfonamide bond, an urethane bond and an urea bond. The linking group may have a plurality of atomic groups of the same kind. Any number of hydrogen atoms bonded to any carbon atom in the linking group may be substituted with a fluorine atom. Any atoms in the linking group may be bonded together to form a ring structure.

The repeating unit (a) is formed by cleavage of the double bond of the unsaturated double bond-containing group) ($R^0$) of the fluorine-containing unsaturated carboxylic acid ester of the general formula (1). In this polymerization reaction, there occurs no change in the bond, other than the polymerizable double bond, and structure of the fluorine-containing unsaturated carboxylic acid ester. Namely, the fluorine-containing polymer having the repeating unit (a) of the general formula (2) is obtained by polymerization of the fluorine-containing monomer of the general formula (1). The definitions of $R^6$, $R^7$ and $W^1$ are the same as those in the general formula (1). The preferable structures of $R^6$, $R^7$ and $W^1$ in the fluorine-containing unsaturated carboxylic acid ester of the general formula (1) can be thus also applied to those in the general formula (2). Further, the preferable structures of $R^3$, other than ethyl, in the general formula (1) can be also applied to that in the general formula (2) as $R^8$ represents the same as $R^3$ in the general formula (1) except for ethyl.

The fluorine-containing polymer can be in the form of either a homopolymer of the repeating unit (a) or a copolymer of the repeating unit (a) and any other repeating unit(s). In the copolymer, the other repeating unit(s) can be selected as appropriate in order to adjust the positive resist function, resist dry etching resistance, resist compatibility with alkali developer (standard developer), adhesion to substrate, resist profile and the other generally required resist performance such as resolution, heat resistance, water repellency, sensitivity etc. As will be explained later, there can be used a repeating unit (b) as a repeating unit having a positive resist function in the fluorine-containing polymer of the present invention. In the case of using the fluorine-containing polymer in the resist film, formed from the resist composition containing a base resin with a resist function, for control of the water repellency and water affinity of the resist film or in the case of using the fluorine-containing polymer in the top coat film on the resist film for pattern formation in semiconductors, the other repeating unit(s) can be selected as appropriate in order to adjust the resist performance such as dry etching resistance, compatibility with alkali developer (standard developer), adhesion to substrate, resist profile, water repellency, advancing or receding contact angle, the water dissolution resistance and selective solvent solubility of the resist composition etc.

The fluorine-containing polymer of the present invention has a molecular weight of generally 1,000 to 1,000,000, preferably 2,000 to 500,000, in terms of mass-average molecular weight as measured by gel permeation chromatography (GPC). If the mass-average molecular weight of the fluorine-containing polymer is less than 1,000, the resulting film may not have sufficient strength. If the mass-average molecular weight of the fluorine-containing polymer exceeds 1,000,000, the solvent solubility of the fluorine-containing polymer decreases so that it is unfavorably difficult to form the smooth film. Preferably, the fluorine-containing polymer has a molecular weight distribution (Mw/Mn) of 1.01 to 5.00, more preferably 1.01 to 4.00, still more preferably 1.01 to 3.00, most preferably 1.10 to 2.50.

The polymer of the present invention can be formed from the repeating units of different properties. There is no particular limitation on the content ratio of the repeating units in the polymer. For example, the content ratio of the repeating units can be suitably set to the following range. Further, each of the repeating unit (a), the repeating unit (b) and the after-mentioned repeating unit (c) may be of a plurality of different kinds of repeating units.

In the polymer of the present invention, the repeating unit (a) derived from the fluorine-containing monomer of the general formula (2) is contained in an amount of 1 to 100 mol %, preferably 5 to 90 mol %. In the case of using the polymer in the positive resist composition, the acid-labile protecting group-containing repeating unit (b) is contained in an amount of 1 to 99 mol %, preferably 5 to 80 mol %, more preferably 10 to 60 mol %, in the polymer. If the content of the repeating unit (a) derived from the fluorine-containing monomer of the general formula (2) is less than 1 mol %, it cannot be expected to obtain the clear effects of improvements in water repellency and advancing/receding contact angle by the use of the monomer of the present invention. If the content of the acid-labile protecting group-containing repeating unit (b) is less than 1 mol %, the change in alkali developer solubility by exposure is unfavorably too small. The repeating unit (c), different from the repeating units (a) and (b), may be contained in an amount of 5 to 90 mol %, preferably 10 to 80 mol %, more preferably 15 to 70 mol %, in the polymer. If the content of the repeating unit (c) is less than 5 mol %, it cannot be expected to improve notably the substrate adhesion by the use of the repeating unit (c). If the content of the repeating unit (c) exceed 90 mol %, the content of the repeating unit (a) that allows improvement in water repellency and the content of the repeating unit (b) that has the resist function become unfavorably too small to obtain sufficient improvement in advancing/receding contact angle and to secure sufficient selectivity and solubility change.

In the case of using the polymer in the resist film, formed from the resist composition containing a base resin with a resist function, for control of the water repellency and water affinity of the resist film or in the case of using the polymer in the top coat film on a resist film, it is unfavorable that the polymer has a positive resist function. In this case, the repeating unit (c), which is different from the repeating units (a) and (b) and does not have an acid-labile protecting group, is contained in and amount of 5 to 90 mol %, preferably 10 to 80 mol %, more preferably 15 to 70 mol %, in the polymer in addition to the repeating unit (a) as mentioned above. If the content of the repeating unit (c) is less than 5 mol %, it cannot be expected to improve notably the substrate adhesion by the use of the repeating unit (c). If the content of the repeating unit (c) exceeds 90 mol %, the content of the water-repellency improving repeating unit (a) becomes unfavorably too small to obtain improvement in advancing/receding contact angle.

[Repeating Unit (b)]

The fluorine-containing polymer of the present invention can be used as a positive resist material by the introduction of an acid-labile protecting group thereto. The acid-labile protecting group can be introduced by the use of an acid-labile group-containing polymerizable monomer. In general, there can suitably be used a polymerizable monomer in which an acid-labile group is ester-bonded to a carboxyl group although a polymerizable monomer in which a hydroxyl group of a hexafluoroisopropyl hydroxyl moiety or a hydroxyl group bonded to an aromatic ring is protected with an acid-labile protecting group is usable as the acid-labile group-containing polymerizable monomer. The acid-labile protecting group-containing repeating unit (b) can be introduced by the use of such an acid-labile protecting group-containing polymerizable compound.

In the present invention, the repeating unit (b) is represented by the general formula (5).

[Chem. 26]

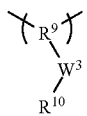
(5)

In the above formula, $R^9$ is either one of the following groups.

[Chem. 27]

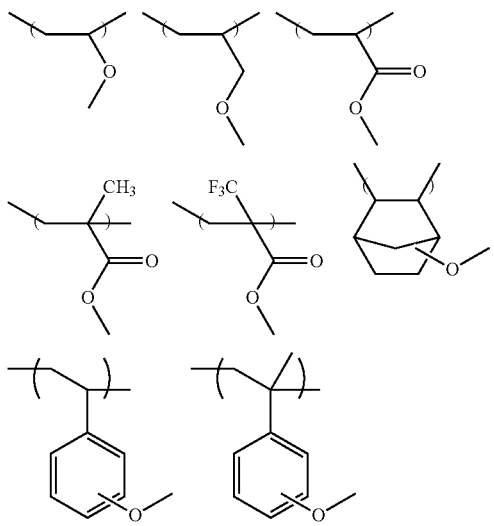

More specifically, $R^9$ is formed by cleavage of a double bond of either one of the following polymerizable double bond-containing groups.

[Chem. 28]

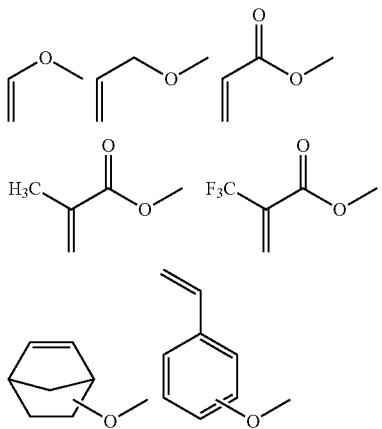

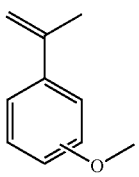

Further, $W^3$ is a divalent linking group having a main skeleton formed by one atomic group, or two or more atomic groups in combination, selected from the group consisting of a single bond, substituted or unsubstituted methylene groups, divalent cyclic alkyl groups (alicyclic hydrocarbon groups), divalent aryl groups (aromatic hydrocarbon groups), substituted or unsubstituted condensed polycyclic aromatic groups, divalent heterocyclic groups, a carbonyl group, an ether group, a ester bond, an oxycarbonyl bond, a thioether group, an amide bond, a sulfonamide bond, an urethane bond and an urea bond. The linking group may have a plurality of atomic groups of the same kind. Any number of hydrogen atoms bonded to any carbon atom in the linking group may be substituted with a fluorine atom. Any atoms in the linking group may be bonded together to form a ring structure.

$R^{10}$ is an acid-labile protecting group.

As the linking group $W^3$, there can be used those obtained by the following combinations of the two or more atomic groups:

$-(CR^4R^5)_m-C(=O)-O-(CR^4R^5)_n-$;

$-(CR^4R^5)_m-C(=O)-O-(CR^4R^5)_n-B-(CR^4R^5)_l$;

$-(CR^4R^5)_m-O-(CR^4R^5)_n-$;

$-(CR^4R^5)_m-O-(CR^4R^5)_n-B-(CR^4R^5)_l-$;

$-(CR^4R^5)_n-B-(CR^4R^5)_l-C(=O)-O-(CR^4R^5)_m-$; and $-(CR^4R^5)_n-B-(CR^4R^5)_l-O-(CR^4R^5)_m-$.

Herein, $-(CR^4R^5)-$ represents the same as represented by the above general formula (3); l, m and n each independently represent an integer of 0 to 10. Preferably, m is 0; and l and n are 0 or 1. Further, B represents a cyclic group such as a divalent alicyclic hydrocarbon group or a divalent aromatic hydrocarbon group. The same explanations of the divalent alicyclic and aromatic hydrocarbon groups in the linking group $W^1$ of the general formula (1) or (2) can be applied to the cyclic group B.

Specific examples of the linking group $W^3$ are — (single bond); $-O-$; $-C(=O)-O-$; $-CH_2-O-$; $-C_6H_4-O-$; $-O-CH_2-$; $-CH_2-C(=O)-O-$; $-C(=O)-O-CH_2-$; $-CH_2-O-CH_2-$; $-CH_2C(=O)-O-CH_2-$; $-C(=O)-O-B-$ (where B is the cyclic group as explained above); $-C(=O)-O-CR^4R^5-$; or $-C_6H_4-O-CR^4R^5-$. Herein, the symbols $R^4$ and $R^5$ have the same definitions as those in the general formula (3) and each preferably independently represent a hydrogen atom, a fluorine atom, an alkyl group, a substituted alkyl group or an alicyclic hydrocarbon group. One or more hydrogen atom of the above group may be substituted with a fluorine atom. Among others, $-C(=O)-O-CR^4R^5-$ where $R^4$ and $R^5$ are each independently a hydrogen atom or a lower alkyl group is preferred. Particularly preferred are $-C(=O)-O-$ and $-C_6H_4-O-$.

As the acid-labile protecting group $R^{10}$, there can be used the following groups:

$$R^{11}-O-C(=O)- \quad (L-1);$$

$$R^{11}-O-CHR^{12}- \quad (L-2);$$

$$CR^{13}{}_R{}^{14}R^{15}- \quad (L-3);$$

$$SiR^{13}R^{14}R^{15}- \quad (L-4); \text{ and}$$

$$R^{11}-C(=O)- \quad (L-5).$$

Herein, $R^{11}$, $R^{12}$, $R^{13}$, $R^{14}$ and $R^{15}$ each independently represent monovalent organic groups as explained below. Among others, the acid-labile protecting groups of the formulas (L-1), (L-2) and (L-3) have a chemical amplification resist function and thus can be particularly suitably used in resist compositions for pattern formation by exposure to high energy radiation or electron beam radiation.

$R^{11}$ is an alkyl group, an alicyclic hydrocarbon group or an aryl group. $R^{12}$ is a hydrogen atom, an alkyl group, an alicyclic hydrocarbon group, an alkenyl group, an aralkyl group, an alkoxy group or an aryl group. $R^{13}$, $R^{14}$ and $R^{15}$ may be the same or different and each are an alkyl group, an alicyclic hydrocarbon group, an alkenyl group, an aralkyl group or an aryl group. Two or more of $R^{13}$, $R^{14}$ and $R^{15}$ may be bonded together to form a ring.

Examples of the alkyl group are those preferably having 1 to 4 carbon atoms, such as methyl, ethyl, propyl, isopropyl, n-butyl, sec-butyl and tert-butyl. Examples of the alicyclic hydrocarbon group are those preferably having 3 to 30 carbon atoms, such as cyclopropyl, cyclopentyl, cyclohexyl, adamantyl, norbornyl, bornyl, tricyclodecanyl, dicyclopentenyl, norbonanepoxy, menthyl, isomenthyl, neomenthyl, tetracyclododecanyl and steroid residue. Examples of the alkenyl group are those preferably having 2 to 4 carbon atoms, such as vinyl, propenyl, allyl and butenyl. Examples of the aryl group are those preferably having 6 to 14 carbon atoms, such as phenyl, xylyl, toluic, cumenyl, naphthyl and anthracenyl. The aryl group may have a substituent. Examples of the aralkyl group are those having 7 to 20 carbon atoms with or without a substituent, such as benzyl, phenethyl and cumyl.

As the substituent of the above organic group, there can be used: a hydroxyl group; a halogen atom (fluorine, chlorine, bromine, iodine); a nitro group; a cyano group;

any alkyl group or alicyclic hydrocarbon group exemplified above; an alkoxy group such as methoxy, ethoxy, hydroxyethoxy, propoxy, hydroxypropoxy, n-butoxy, isobutoxy, sec-butoxy or tert-butoxy; an aralkyl group such as benzyl, phenethyl or cumyl; an aralkyloxy group; an acyl group such as acetyl, butyryl, benzoyl, cyanamyl or valeryl; an acyloxy group such as butyryloxy; any alkenyl group exemplified above; an alkenyloxy group such as vinyloxy, propenyloxy, allyloxy or butenyloxy; any aryl group exemplified above; an aryloxy group such as phenoxy; and an aryloxycarbonyl group such as benzoyloxy.

There can also be used lactone groups of the following formulas (7-1) and (7-2).

[Chem. 29]

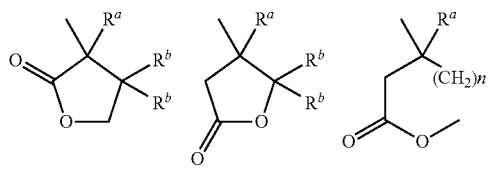

(7-1)

[Chem. 30]

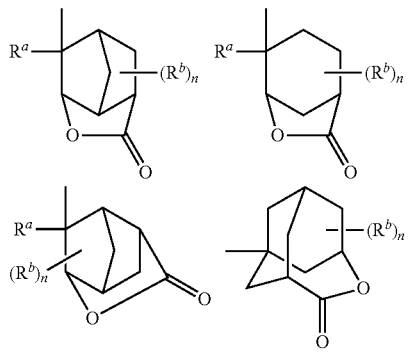

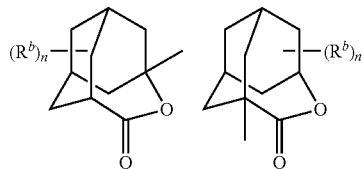

(7-2)

In the above formulas, $R^a$ represents a $C_1$-$C_4$ alkyl or perfluoroalkyl group; $R^b$ each independently represents a hydrogen atom, a $C_1$-$C_4$ alkyl or perfluoroalkyl group, a hydroxyl group, a carboxylic acid group, an alkyloxycarbonyl or an alkoxy group; and n represents an integer of 1 to 4.

The following are specific examples of the acid-labile protecting group.

Examples of the alkoxycarbonyl group represented by $R^{11}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantaneoxycarbonyl.

Examples of the acetal group represented by $R^{11}$—O—$CHR^{12}$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyloxyethyl, 1-ethoxyisobutyl, 1-methoxyethoxymethyl, tetrahydropyranyl and tetrahydrofuranyl. There can also be used acetal groups obtained by addition of vinyl ethers to hydroxyl groups.

Examples of the tertiary hydrocarbon group represented by $CR^{13}R^{14}R^{15}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

The alicyclic hydrocarbon group or the alicyclic hydrocarbon-containing acid-labile protecting group can be exemplified as follows.

[Chem. 31]

(8-1)

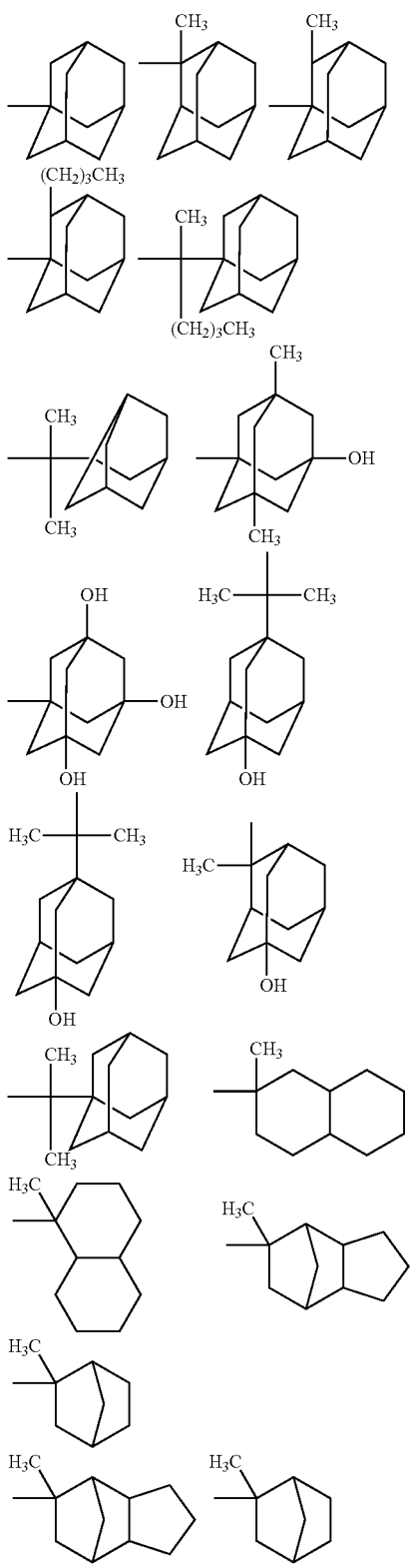

[Chem. 32]

-continued (8-2)

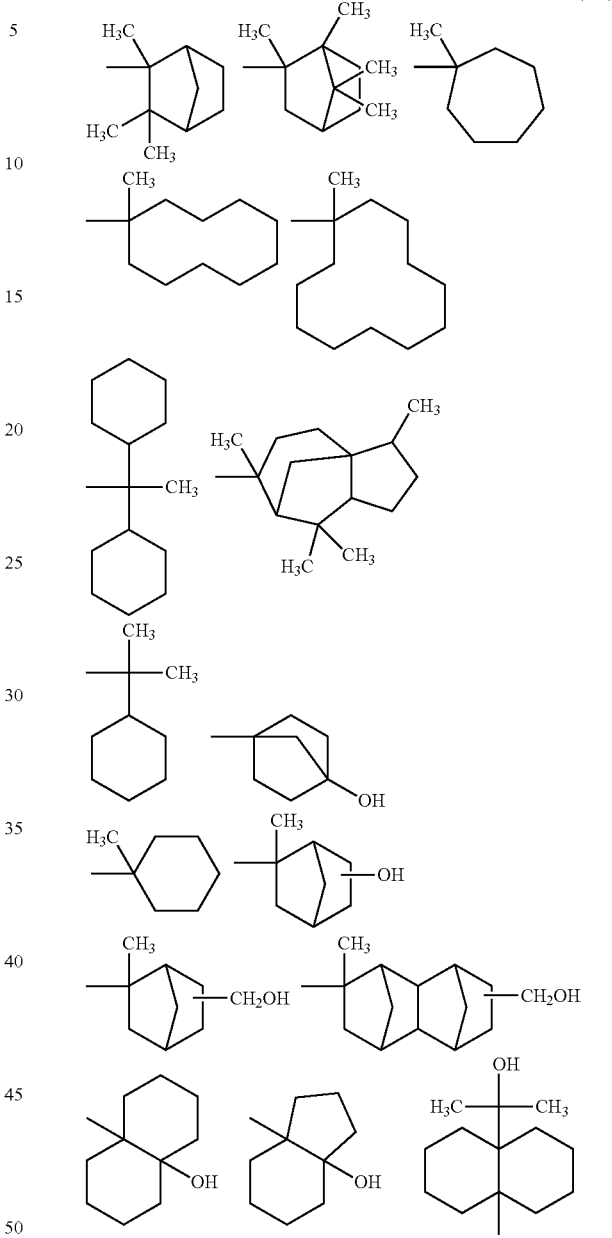

In the formulas (8-1) and (8-2), methyl ($CH_3$) groups may independently be replaced by ethyl groups; and one or two or more of the ring carbons may have a substituent group as mentioned above.

Examples of the silyl group represented by $SiR^{13}R^{14}R^{15}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Examples of the acyl group represented by $R^{11}$—C (=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. There can also be used those obtained by substitution of a part or all of hydrogen atoms of the above acid labile groups with a fluorine atom.

The lactone-containing acid-labile protecting group can be exemplified by the following formulas (9), (10) and (11).

[Chem. 33]

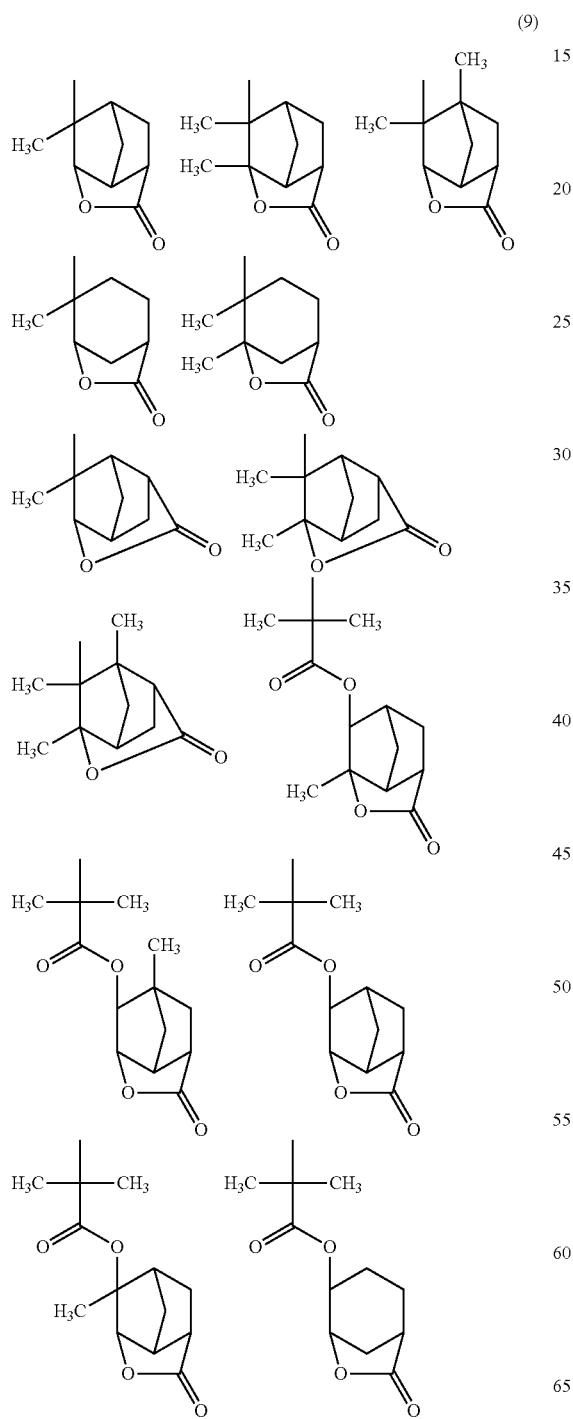

(9)

-continued

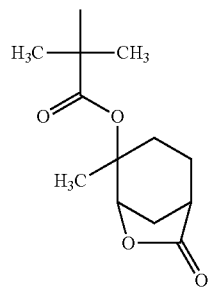

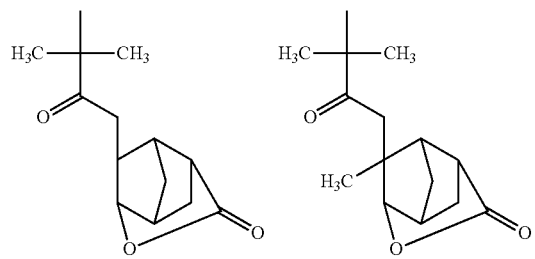

[Chem. 34]

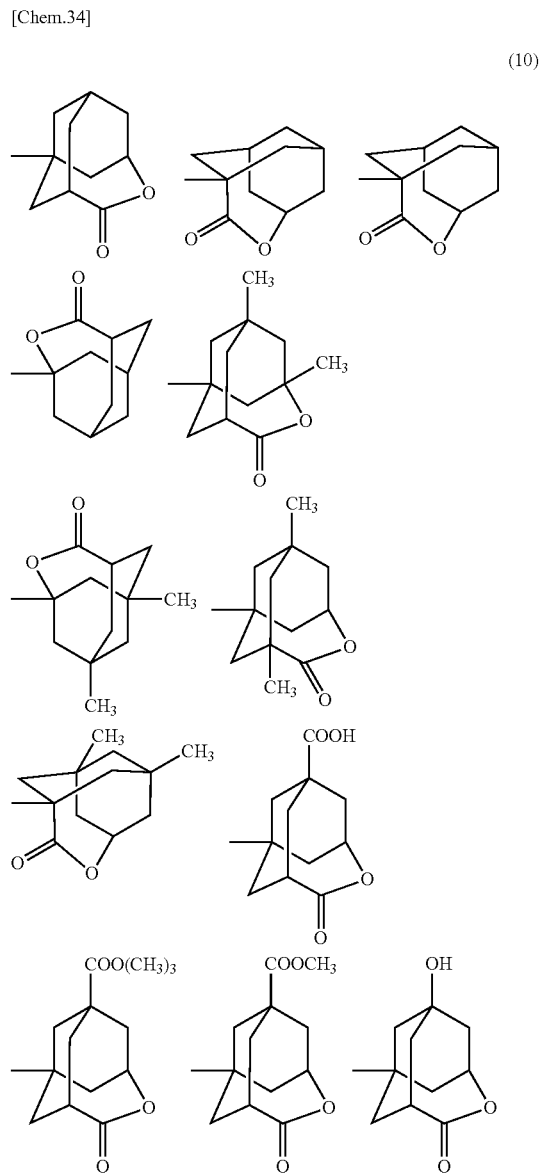

(10)

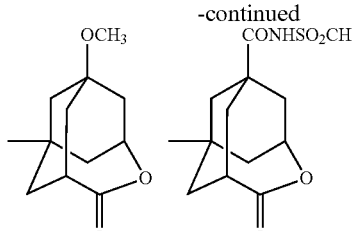

[Chem. 35]

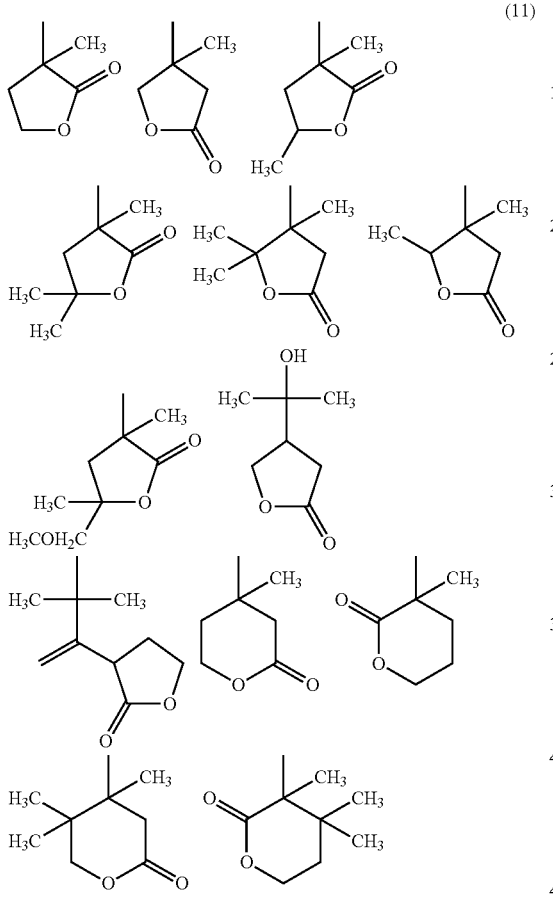

In the formulas (9), (10) and (11), methyl (CH$_3$) groups may independently be replaced by ethyl groups.

In the case of using a ArF excimer laser as an exposure light source, the acid-labile protecting group is preferably a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an alicyclic hydrocarbon group such as adamantyl or isobornyl, an alicyclic hydrocarbon-containing acid labile protecting group or a lactone-containing acid labile protecting group.

Two or more kinds of the repeating unit (b) may be used in combination.

As another technique to produce the acid-labile polymer or resist material, it is feasible to prepare the polymer and then introduce an acid-labile group into the polymer by polymer reaction or to an acid-labile compound in monomer or polymer form.

The purpose of utilizing the acid-labile group is to develop, under the acid labile properties of the acid-labile group, positive photosensitivity and solubility to alkali developer after exposure to high energy ray radiation of 300 nm or less wavelength, such as ultraviolet radiation, excimer laser radiation or X-ray radiation or electron beam radiation.

Specific examples of the acid labile protecting groups of the general formulas (L-1) to (L-3) include, but are not limited to, the following ones.

[Chem. 36]

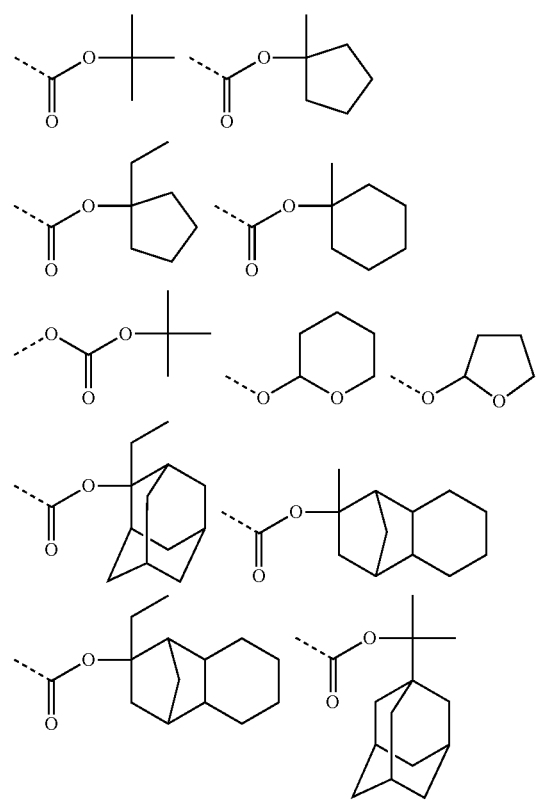

[Chem. 37]

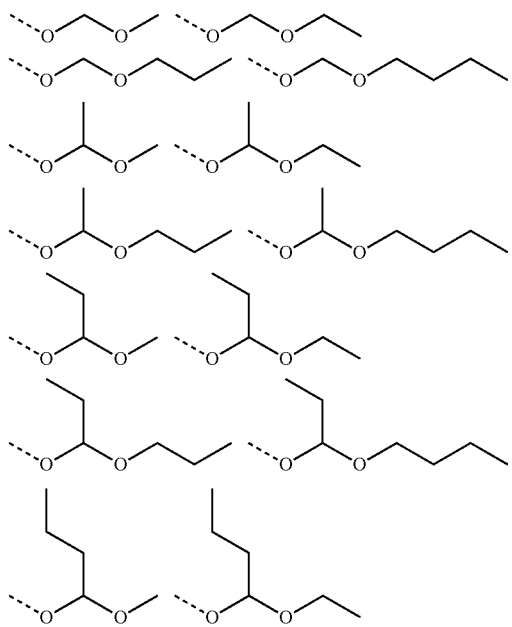

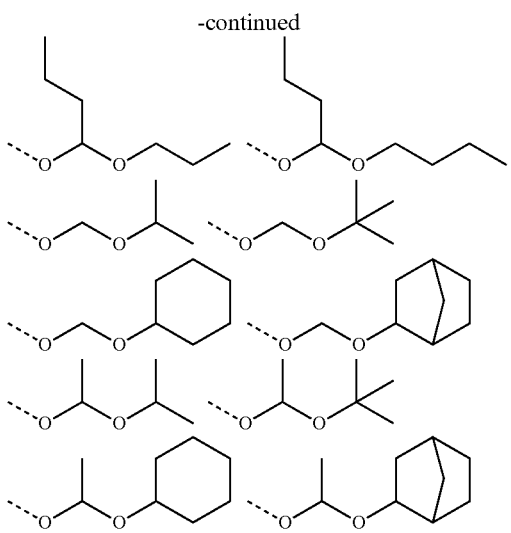

[Repeating Unit (c)]

The repeating unit (c) is a repeating unit having no acid labile protecting group and no positive resist function and used in combination to control various properties of the base resin.

The repeating unit (c) can be introduced by the use of any monomer having no acid labile group and capable of copolymerizing with the fluorine-containing unsaturated carboxylic acid of the present invention. As such a monomer, there can be used polymerizable compounds, such as maleic anhydride, acrylic acid esters, fluorine-containing acrylic acid esters, methacrylic acid esters, fluorine-containing methacrylic acid esters, styrenic compounds, fluorine-containing styrenic compounds, vinyl ethers, fluorine-containing vinyl ethers, allyl ethers, fluorine-containing allyl ethers, olefins, fluorine-containing olefins, norbornene compounds, fluorine-containing norbornene compounds, sulfur dioxide, vinyl silanes, vinyl sulfonic acids and vinyl sulfonic acid esters, each having no acid labile group in the molecule. In the present invention, the fluorine-containing polymer is preferably produced by copolymerization of the fluorine-containing unsaturated carboxylic acid with one or more kinds of monomers selected from the above polymerizable compounds.

There is no particular limitation on the ester side chain of the copolymerizable acrylic or methacrylic acid ester monomer. Examples of the acrylic or methacrylic acid ester are: acrylic esters of acrylic or methacrylic acid, such as methyl acrylate, methyl methacrylate, ethyl acrylate, ethyl methacrylate, n-propyl acrylate, n-propyl methacrylate, isopropyl acrylate, isopropyl methacrylate, n-butyl acrylate, n-butyl methacrylate, isobutyl acrylate, isobutyl methacrylate, n-hexyl acrylate, n-hexyl methacrylate, n-octyl acrylate, n-octyl methacrylate, 2-ethylhexyl acrylate, 2-ethylhexyl methacrylate, lauryl acrylate, lauryl methacrylate, 2-hydroxyethyl acrylate, 2-hydroxyethyl methacrylate, 2-hydroxypropyl acrylate and 2-hydroxypropyl methacrylate; acrylates or methacrylates containing an ethylene glycol group, a propylene glycol group, a tetramethylene glycol group etc.; unsaturated amides such as acrylamide, metacrylamide, N-methylol acrylamide, N-methylol methacrylamide and diacetone acrylamide; acrylonitrile; methacrylonitrile; alkoxysilane-containing vinylsilanes and acrylic or methacrylic acid esters; tert-butyl acrylate; tert-butyl methacrylate; 3-oxocyclohexyl acrylate; 3-oxocyclohexyl methacrylate; adamantyl acrylate; adamantyl methacrylate; methyladamantyl acrylate; methyladamantyl methacrylate; ethyladamantyl acrylate; ethyladamantyl methacrylate; hydroxyadamantyl acrylate; hydroxyadamantyl methacrylate; cyclohexyl acrylate; cyclohexyl methacrylate; tricyclodecanyl acrylate; tricyclodecanyl methacrylate; acrylates or methacrylates containing a ring structure such as a lactone ring or a norbornene ring; acrylic acid; and methacrylic acid. There can also be used acrylate compounds in each of which a cyano group is introduced to α-position of the above acrylate, and analogous thereof, such as maleic acid, fumaric acid and maleic anhydride as the copolymerizable monomer.

Examples of the fluorine-containing acrylic or methacrylic acid ester are acrylic or methacrylic esters each having a fluorine atom or fluorine-containing group in its α-position or acrylic or methacrylic esters each having a fluorine atom in its ester moiety. There can also suitably be used fluorine-containing acrylic or methacrylic ester compounds containing fluorine atom in both of α-position and ester moiety. A cyano group may be introduced into the α-position of the fluorine-containing acrylic or methacrylic ester. For example, the acrylic or methacrylic ester monomer having a fluoroalkyl group in α-position can be exemplified by those in which a trifluoromethyl group, a trifluoroethyl group, a nonafluoro-n-butyl group etc. has been added to α-position of the above non-fluorinated acrylic ester or methacrylic ester.

On the other hand, the acrylic or methacrylic ester monomer having fluorine in its ester moiety can be exemplified by those in which the ester moiety has a fluorinated alkyl group such as perfluoroalkyl group or fluoroalkyl group or those in which a fluorine atom-, trifluoromethyl- or hexafluoroisopropyl hydroxyl-substituted cyclic structure such as a fluorine-containing benzene ring, a fluorine-containing cyclopentane ring, a fluorine-containing cyclohexane ring or a fluorine-containing cycloheptane ring coexists with a fluorine atom in the ester moiety. An acrylic ester or methacrylic ester with a fluorine-containing t-butyl ester moiety is also usable as a monomer. The fluorine-containing acrylic or methacrylic acid ester can have a fluorine-containing alkyl group in α-position in addition to the above fluorine-containing functional group. Typical examples of the fluorine-containing acrylic or methacrylic acid ester are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, 6-[3,3,3-trifluoro-2-hydroxy-2-(trifluoromethyl)propyl]bicyclo[2.2.1]hept-2-yl acrylate, 6-[3,3,3-trifluoro-2-hydroxy-2-(trifluoromethyl)propyl]bicycle[2.2.1]hept-2-yl 2-(trifluoromethyl)acrylate, 6-[3,3,3-trifluoro-2-hydroxy-2-(trifluoromethyl)propyl]bicycle[2.2.1]hept-2-yl methacrylate, 1,4-bis(1,1,1,3,3,3-hexafluoro-2-hydroxyisopropyl)cyclohexyl acrylate, 1,4-bis(1,1,1,3,3,3-hexafluoro-2-hydroxyisopropyl)cyclohexyl methacrylate and 1,4-bis(1,1,1,3,3,3-hexafluoro-2-hydroxyisopropyl)cyclohexyl 2-trifluoromethyl acrylate.

The polymerizable hydroxyhexafluoroisopropyl group-containing compound is preferably used in copolymerization for the introduction of the repeating unit (c) so as to increase the solvent solubility of the fluorine-containing polymer in the present invention. The following are specific examples of the polymerizable hydroxyhexafluoroisopropyl group-containing compound.

[Chem. 38]

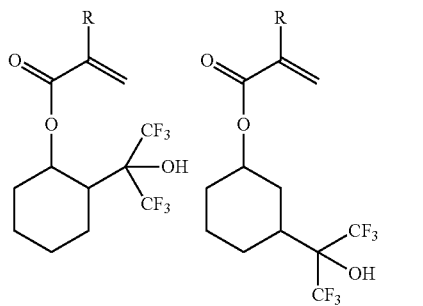

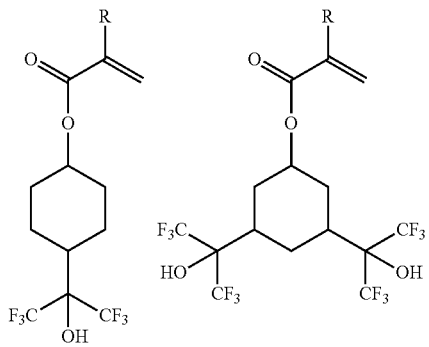

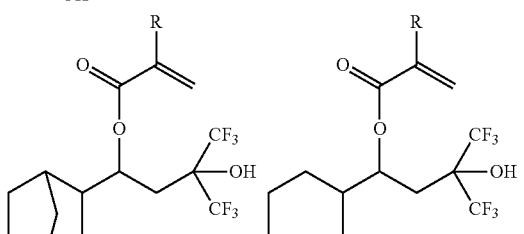

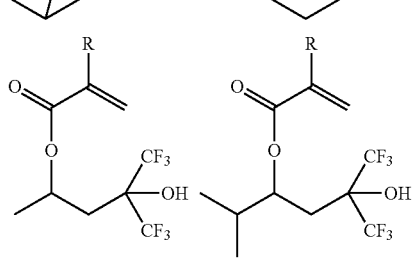

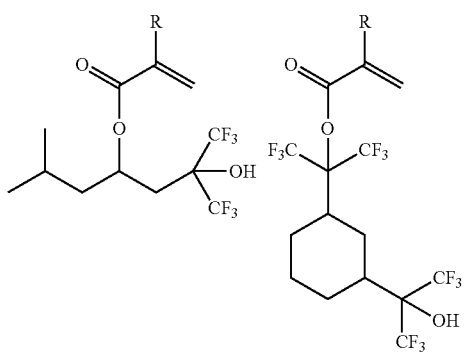

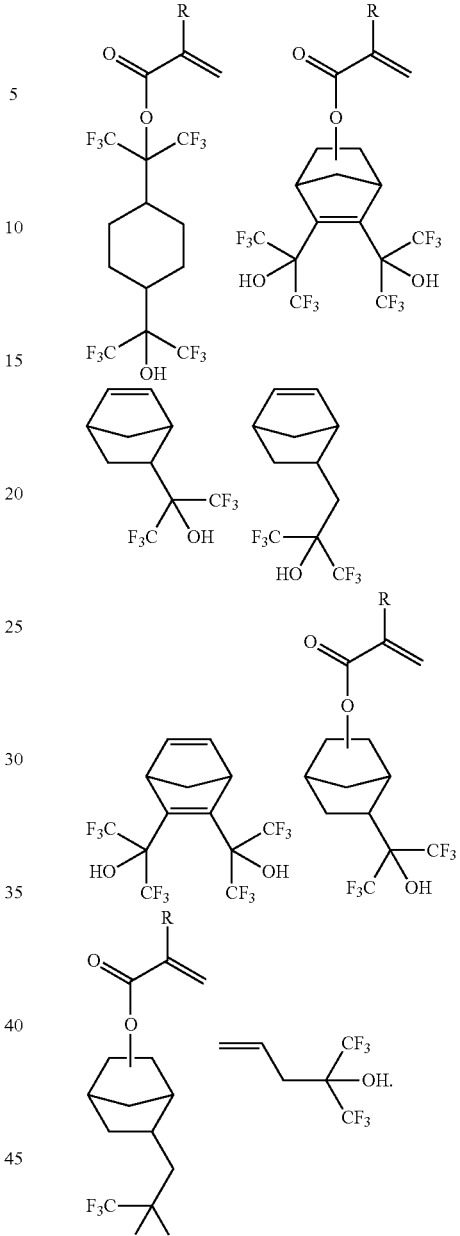

In the above formulas, R each independently represents a hydrogen atom, a methyl group, an ethyl group or a trifluoromethyl group. The hydroxyhexafluoroisopropyl group may be protected with a protecting group. This protecting group is a conventional protecting group used in the field of organic syntheses and is relatively stable and different from the acid-labile group (acid-labile protecting group), which is readily dissociated by the acid generated from the acid generator as exemplified by the general formulas (L-1) to (L-5).

Examples of the copolymerizable styrenic compound or fluorine-containing styrenic compound are styrene, fluorine-containing styrene and hydroxystyrene. More specifically, the fluorine-containing styrene can be exemplified by those in which hydrogen(s) on the aromatic ring has been substituted with a fluorine atom or trifluoromethyl group, such as pentafluorostyrene, trifluoromethylstyrene and bistrifluoromethylstyrene. The hydroxystyrene can be exemplified by those in which hydrogen(s) on the aromatic ring has been substituted with a hexafluoroisopropyl hydroxyl group or protected hexafluoroisopropyl hydroxyl group. A halogen, an alkyl group or a fluoroalkyl group may be bonded to α-position of the above styrene compound. There can also be used a perfluorovinyl-containing styrene.

Examples of the copolymerizable vinyl ether, fluorine-containing vinyl ether, allyl ether or fluorine-containing allyl ether are alkyl vinyl ethers or alkyl allyl ethers, each of which may contain a methyl group, an ethyl group or a hydroxy group such as hydroxyethyl or hydroxybutyl. There can also be used a cyclic vinyl or allyl ether having a ring structure such as a cyclohexyl group, a norbornyl group or an aromatic ring that may contain a hydrogen or carbonyl bond as well as any fluorine-containing vinyl or allyl ether obtained by substitution of all or part of hydrogen atoms of the above functional group with fluorine.

In the present invention, there can be used vinyl ester, vinyl silane, olefin, fluorine-containing olefin, norbornene compound, fluorine-containing norbornene compound and other polymerizable unsaturated bond-containing compound without particular limitation.

Examples of the copolymerizable olefin are ethylene, propylene, isobutene, cyclopentene and cyclohexene. Examples of the copolymerizable fluorine-containing olefin are vinyl fluoride, vinylidene fluoride, trifluoroethylene, chlorotrifluoroethylene, tetrafluoroethylene, hexafluoropropylene and hexafluroisobutene.

Examples of the copolymerizable norbornene compound or fluorine-containing norbornene compound are norbornene monomers each having a mononuclear or multinuclear structure and, more specifically, norbornene compounds, such as 3-(5-bicyclo[2.2.1]hepten-2-yl)-1,1,1-trifluoro-2-(trifluoromethyl)-2-propanol, formed by Diels-Alder addition reaction of an unsaturated compound such as a fluorine-containing olefin, an allyl alcohol, a fluorine-containing allyl alcohol, a homoallyl alcohol, a fluorine-containing homoallyl alcohol, acrylic acid, α-fluoroacrylic acid, α-trifluoromethylacrylic acid, methacrylic acid, any acrylic ester, methacrylic ester, fluorine-containing acrylic ester or fluorine-containing methacrylic ester described above in the present specification, 2-(benzoyloxy)pentafluoropropane, 2-(methoxyethoxyethyloxy)pentafluoropropene, 2-tetrahydroxypyranyloxy)pentafluoropropane, 2-(benzoyloxy)trifluoroethylene or 2-(methoxymethyloxy)trifluoroethylene with cyclopentadiene or cyclohexadiene.

[Polymerization Process]

In the present invention, there is no particular limitation on the polymerization process for production of the fluorine-containing polymer. The polymerization reaction can be done by any common polymerization process. It is preferable to adopt radical polymerization process or ionic polymerization process. In some cases, it is feasible to adopt coordination anionic polymerization process, living anionic polymerization process, cationic polymerization process, ring-opening metathesis polymerization process, vinylene polymerization process or vinyl addition process.

The radical polymerization process can be conducted by a known polymerization technique such as bulk polymerization, solution polymerization, suspension polymerization or emulsion polymerization technique in a batch, semi-continuous or continuous operation system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction.

Further, the polymerization reaction can be done by the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents are also usable. These solvents can be used solely or in combination of two or more thereof. A molecular weight adjusting agent such as mercaptan may be used in combination.

The reaction temperature of the copolymerization reaction is set as appropriate depending on the kind of the radical polymerization initiator or radical initiating source and is generally preferably in the range of 20 to 200° C., more preferably 30 to 140° C.

The organic solvent or water can be removed from the resulting fluorine-containing polymer solution or dispersion by reprecipitation, filtration, distillation with heating under a reduced pressure or the like.

[Resist Composition]

One use of the fluorine-containing polymer of the present invention is a resist composition. When the fluorine-containing polymer has a positive resist function, the resist composition contains, in addition the fluorine-containing polymer, at least an acid generator and a solvent and optionally any additive(s) such as a basic compound, a dissolution inhibitor and/or a surfactant. The resist composition may be prepared by the addition of a positive resist or base resin of different structure to the positive resist base resin of the present invention. There may be used a base resin having a different kind of acid labile protecting group.

In the present invention, the positive resist composition has water repellency (contact angle) at a surface thereof in contact with water in liquid immersion lithography. More specifically, the positive resist composition has an advancing contact angle of 85 to 105 degrees and a receding contact angle of 70 to 90 degrees. If the water repellency is lower than 85 degrees in terms of the advancing contact angle or lower than 70 degrees in terms of the receding contact angle, the interaction of the resist and water becomes unfavorably so large that there occurs optical system contamination or nonuniform exposure due to transfer of the additive such as photoacid generator from the resist composition to immersion water. Further, it is unfavorable in view of cost that there occurs throughput deterioration as the stepper scan speed cannot be increased if the receding contact angle is lower than 70 degrees. If the water repellency is higher than 105 degrees in terms of the advancing contact angle or higher than 90 degrees in terms of the receding contact angle, the contact of the resist with the alkali developer may be interfered so that the resist composition becomes difficult to dissolve. It is also unfavorable in view of cost that there occurs throughput deterioration as the water layer cannot be formed stably and as the stepper scan speed cannot be increased.

When the fluorine-containing polymer has no resist function, by contrast, the resist composition contains, in addition the fluorine-containing polymer, at least a base resin having a positive resist function, an acid generator and a solvent. Even in this case, any additive(s) such as a basic compound, a dissolution inhibitor and/or a surfactant can be used.

Various additives miscible with the resist composition, such as an additional resin, a plasticizer, a stabilizer, a coloring agent, a surfactant, a viscosity improver, a leveling agent, an antifoaming agent, a compatibilizer, a primer and an antioxidant, may be added as desired.

[Additive Resin]

There is no particular limitation on the additive resin as long as the additive resin is soluble in the solvent used and is compatible with the other components of the resist composition. The additive resin performs the function as a plasticizer, a stabilizer, a viscosity improver, a leveling agent, an antifoaming agent, a compatibilizer, a primer etc.

[Basic Compound]

In the resist composition of the present invention, the basic compound is preferably contained as an optional component so as to serve as a quencher or to obtain improvements in resist pattern shape and post exposure stability.

There can be used any known basic compounds such as primary, secondary and tertiary aliphatic amines, aromatic amines, heterocyclic amines, nitrogen-containing compounds with hydroxyphenyl groups, alcoholic nitrogen-containing compounds and amide derivatives. Among others, secondary and tertiary apliphatic amines, aromatic amines and heterocyclic amines are preferred.

The aliphatic amines include alkylamines or alkylalcoholamines each formed by replacing at least one hydrogen of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

The other basic compounds are listed as follows. Examples of the aromatic or heterocyclic amines are aniline and aniline derivatives such as N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine. Examples of the heterocyclic amines are 1,5-diazabicyclo[4.3.0]nona-5-ene, 1,8-diazabicyclo[5.4.0]undeca-7-ene, 1,4-diazabicyclo[2.2.2]octane, 4-dimethylaminopyridine, hexamethylenetetramine and 4,4-dimethylimidazoline. There can also be used hindered amines such as bis(1,2,2,6,6-pentamethyl-4-piperidyl)sebacate. Examples of the alcoholic nitrogen-containing compounds are 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine and 1-[2-(2-hydroxyethoxy)ethyl]piperazine.

These basic compounds can be used solely or in combination of two or more thereof.

The amount of the basic compound used is generally 0.01 to 5 parts by mass per 100 parts by mass of the base resin.

[Solvent]

As the technique to form the resist composition of the fluorine-containing polymer into a thin film in the present invention, it is feasible to dissolve the polymer and the like in an organic solvent and apply and dry a film of the polymer solution. There is no particular limitation on the organic solvent used as long as the fluorine-containing polymer can be dissolved in the organic solvent. Examples of the organic solvent are: ketones such as acetone, methyl ethyl ketone, cyclohexanone, methyl isoamyl ketone and 2-heptanone; polyhydric alcohols and derivatives thereof, such as ethylene glycol, ethylene glycol monoacetate, diethylene glycol, diethylene glycol monoacetate, propylene glycol, propylene glycol monoacetate, dipropylene glycol, dipropylene glycol monoacetate, and monomethyl ether, monoethyl ether, monopropyl ether, monobutyl ether or monophenyl ether thereof cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. Among others, particularly preferred is propylene glycol monomethyl ether acetate (PGMEA). These solvents can be used solely or in combination of two or more thereof.

[Surfactant]

The surfactant is preferably contained in the resist composition of the present invention. As the surfactant, either one or two or more kinds of fluorine- and/or silicon-based surfactants (fluorine-based surfactants, silicon-based surfactants and surfactant containing both of fluorine and silicon atoms) can suitably be used.

[Acid Generator]

Further, a known photoacid generator is usable in the resist composition of the present invention. As the photoacid generator, there can be used any one selected from photoacid generators for chemically amplified resist compositions. Examples of the photoacid generator are bissulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The amount of the photoacid generator used is generally 0.5 to 20 parts by mass per 100 parts by mass of the resist composition. If the amount of the photoacid generator is less than 0.5 parts by mass, the resin composition unfavorably results in poor pattern formation. If the amount of the photoacid generator exceeds 20 parts by mass, it is difficult to prepare the resin composition into a uniform solution. Further, the resin composition unfavorably tends to become low in storage stability.

[Pattern Formation Method]

The resist composition of the present invention can be applied to resist pattern formation by a conventional photoresist technique. More specifically, a solution of the resist composition is first applied to a substrate e.g. silicon wafer by a spinner etc. and dried (pre-baked), thereby forming a photosensitive film (resist film). The conditions of the drying process can be set as appropriate depending on the resist composition used. The drying process is preferably performed at 80 to 150° C., more preferably 90 to 120° C., for 30 to 120 seconds, preferably 60 to 90 seconds. The photosensitive film is exposed to high energy ray radiation or electron beam radiation by means of any exposure apparatus through a desired mask pattern, and then, heated (post-baked). The conditions of the post-baking process can also be set as appropriate depending on the resist composition used. Preferably, the post-baking process is performed at 80 to 150° C., more preferably 90 to 120° C., for 30 to 120 seconds, preferably 60 to 90 seconds. After that, the exposed photosensitive film is developed with an alkaline developer solution such as an aqueous solution of 0.1 to 10 mass % tetramethylammonium hydroxide. It is possible by such a pattern formation method to obtain a resist pattern according to the mask pattern.

There is no particular limitation on the high energy ray radiation used in the present invention. For fine patterning, it is effective to use high energy ray radiation of 300 nm or less wavelength, such as near-ultraviolet radiation (wavelength: 380 to 200 nm) or vacuum ultraviolet radiation (far-ultraviolet radiation, VUV, wavelength: 200 to 10 nm) e.g. $F_2$ excimer laser radiation, ArF excimer laser radiation or KrF excimer laser radiation, extreme ultraviolet radiation (EUV, wavelength: 10 nm or less) e.g. synchrotron radiation, soft X-ray radiation, X-ray radiation or γ-ray radiation, or electron beam radiation. It is thus effective that the exposure apparatus has an exposure light source for high energy ray radiation of 300 nm or less wavelength or electron beam radiation in the pattern formation method of the present invention. Further, the resist composition of the present invention can be also applied effectively to liquid immersion lithography using a liquid immersion exposure apparatus, which uses a less high-energy ray absorptive medium such as water or fluorinated solvent in a part of optical path and enables more efficient fine patterning in terms of numerical aperture and effective wavelength, and thus can be used in such a liquid immersion exposure apparatus.

[Top Coat Composition]

Another use of the fluorine-containing polymer of the present invention is a top coat composition for liquid immersion lithography. The top coat composition is particularly suitable for use in liquid immersion lithography using water as a medium. In the present invention, the top coat composition has water repellency (contact angle) at a surface thereof in contact with water. More specifically, the top coat composition has an advancing contact angle of 85 to 105 degrees and a receding contact angle of 70 to 90 degrees. If the water repellency is lower than 85 degrees in terms of the advancing contact angle or lower than 70 degrees in terms of the receding contact angle, the interaction of the resist and water becomes unfavorably so large that there occurs optical system contamination or nonuniform exposure due to transfer of the additive such as photoacid generator from the resist composition to immersion water. Further, it is unfavorable in view of cost that there occurs throughput deterioration as the stepper scan speed cannot be increased if the receding contact angle is lower than 70 degrees. If the water repellency is higher than 105 degrees in terms of the advancing contact angle or higher than 90 degrees in teems of the receding contact angle, the contact of the resist with the alkali developer may be interfered so that the resist becomes difficult to dissolve. It is also unfavorable in view of cost that there occurs throughput deterioration as the water layer cannot be formed stably and as the stepper scan speed cannot be increased.

The top coat composition of the present invention is used in the form of a top coat solution (top coat composition solution) in which the fluorine-containing polymer is dissolved in solvent such as an organic solvent or a mixed liquid of water and organic solvent. As the solvent, there can suitably be used any of those unlikely to cause erosion of the resist film and elution of the additive such as photoacid generation from the resist film.

The organic solvent is selected depending on the composition of the resist film. Various organic solvents such as hydrocarbon solvents, alcohol solvents, ether solvents, ester solvents and fluorinated solvents are usable.

Preferably, the solvent is one kind of solvent, or a mixed solvent of two or more kinds of solvents, selected from the group consisting of $C_5$-$C_{20}$ alkanes (saturated aliphatic hydrocarbons) or cycloalkanes (alicyclic hydrocarbons), $C_1$-$C_{20}$ hydrocarbon alcohols and those obtained by any number of hydrogen atoms of each of these alkanes, cycloalkanes and hydrocarbon alcohols with a fluorine atom. More preferably, the solvent is one kind of solvent, or a mixed solvent of two or more kinds of solvents, selected from the group consisting of $C_5$-$C_{10}$ alkanes (saturated aliphatic hydrocarbons) or cycloalkanes (alicyclic hydrocarbons), $C_1$-$C_{10}$ hydrocarbon alcohols and those obtained by any number of hydrogen atoms of each of these alkanes, cycloalkanes and hydrocarbon alcohols with a fluorine atom.

Further, it is preferable that the solvent or mixed solvent has a boiling point of 70 to 170° C. In the spin coating of the top coat composition onto the resist film, the top cat film cannot be formed uniformly due to too fast evaporation of the solvent if the boiling point is lower than 70° C. If the boiling point exceeds 170° C., there unfavorably occurs throughput deterioration as it takes time to dry the top coat film. There can preferably be used a mixed solvent of 50 to 99.9% of a $C_5$-$C_{20}$ hydrocarbon and 0.1 to 50% of a $C_1$-$C_{20}$ hydrocarbon alcohol, more preferably a mixed solvent of 50 to 99.9% of a $C_5$-$C_{10}$ hydrocarbon solvent and 0.1 to 50% of a $C_1$-$C_{10}$ hydrocarbon alcohol.

Specific examples of the organic solvent used solely or as the mixed solvent are: hydrocarbon solvents, i.e., alkanes and cycloalkanes such as pentane, hexane, heptane, octane, nonane, decane and isomers thereof (including cyclic compounds); hydrocarbon alcohols such as butanol (n-, iso- or tert-butanol), methyl ethyl carbinol, pentanol, amyl alcohol, hexyl alcohol, heptyl alcohol and 4-methyl-2-pentanol; and partially-fluorinated hydrocarbon solvents. The partially-fluorinated hydrocarbon alcohols can be exemplified by those in which a part of hydrogen atoms of each of the alkanes, cycloalkanes and hydrocarbon alcohols has been substituted with a fluorine atom. By the introduction of the fluorine atom into the solvent, the polymer of the present invention becomes dissolved effectively in the solvent so that the top coat solution can be applied without causing damage in the resist film.

There is no particular limitation on the amount of the solvent used. It is preferable to control the amount of the solvent in such a manner that the top coat solution has a solid content of 3 to 25%, more preferably 5 to 15%. The thickness of the resin film can be adjusted as appropriate by controlling the solid content of the top coat solution.

In the present invention, a hydrophobic additive for prevention of water swelling or impregnation, an acidic additive for improvement of developer solubility, an acid generator undecomposed at a pre-baking temperature or higher but decomposed at a post-baking temperature and the like may be used in the top coat composition.

The top coat solution of the present invention can be applied regardless of the kind of the resist film therebeneath, that is, can suitably be applied even when the resist film is any resist system.

There is no particular limitation on the exposure wavelength for exposure of the thus-coated resist film in the present invention. As mentioned above, it is effective to use high energy ray radiation of 300 nm or less wavelength, such as KrF excimer laser radiation (wavelength: 248 nm), ArF excimer laser radiation (wavelength: 193 nm), F$_2$ excimer laser radiation (wavelength: 157 nm), EUV, EB or X-ray. In particular, ArF excimer laser radiation is preferably used. Further, the top coat composition of the present invention is particularly suitably applied to liquid immersion lithography.

There is also no particular limitation on the thickness of the top coat film formed from the top coat solution in the present invention. The thickness of the top coat film is generally 10 to 1000 nm, preferably 20 to 200 nm.

It is feasible to remove the top coat film from the exposed resist film with the use of the same solvent as that used in the top coat solution, but is preferable to dissolve and remove (peel off) the top coat film together with the soluble portion of the resist film by the resist developer in substantially one operation. Namely, the top coat film formed from the top coat composition of the present invention can be peeled off by the alkali developer. The dissolution rate of the top coat film is generally 50 to 3000 nm/sec, preferably 100 to 1000 nm/sec. If the dissolution rate is less than 50 nm/sec, it takes long time to treat the top coat film. If the dissolution rate exceeds 3000 nm/sec, the dissolution of the top coat film becomes nonuniform so that the exposed portion of the resist film cannot be dissolved and removed uniformly.

The use of the top coat composition of the present invention for device production by liquid immersion lithography will be explained below.

First, a resist composition solution is applied to a substrate e.g. silicon wafer or semiconductor device substrate by a spinner etc. and pre-baked, thereby forming a photosensitive film (resist film). The conditions of the pre-baking process can be set as appropriate depending on the resist composition used. The pre-baking process is preferably performed at 80 to 150° C., more preferably 90 to 120° C., for 30 to 120 seconds, preferably 60 to 90 seconds.

Next, the top coat solution of the present invention is applied uniformly to a surface of the resist film by a spinner etc. and heat treated, thereby forming a top coat film on the resist film so that the resist film and the top coat film are combined into a two-layer resin film. The conditions of the heat treatment process can be set as appropriate depending on the resist composition and the top coat composition solution used. The heat treatment process is preferably performed at 50 to 100° C., more preferably 60 to 90° C., for 10 to 120 seconds, preferably 30 to 90 seconds. It is preferable to conduct the heat treatment process at a temperature lower than the drying temperature of the resist film.

The substrate on which the two- or multi-layer resin film has been formed is immersed in a medium such as water and exposed to high energy ray radiation through a desired mask pattern. At this time, the exposure radiation passes through the medium (e.g. water) and the top coat film and reaches the resist film. As the resist film is kept separated from the medium (e.g. water) by the top coat film, there does not occur swelling of the resist film due to permeation of the medium (e.g. water) into the resist film or dissolution of the resist film into the medium (e.g. water).

The exposed substrate is post-baked and developed with an alkali developer solution such as an aqueous solution of 0.1 to 10 mass % tetramethylammonium hydroxide. In the development process, the whole of the top coat film is dissolved, and then, the exposed portion of the resist film is dissolved. In other words, the top coat film and the exposed portion of the resist film can be dissolved and removed in one development process operation to obtain a resist pattern according to the desired mask pattern.

EXAMPLES

The present invention will be described in more detail below by way of the following examples. It should be noted that these examples are illustrative and are not intended to limit the present invention thereto.

[Synthesis of Monomers]

Synthesis Example 1

Synthesis of methacrylic acid 1-chlorocarbonyl-1,1-difluoro-2-butyl ester

[Chem. 39]

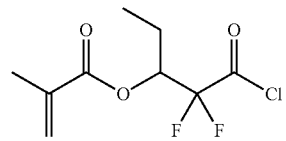

Into a 3 L vessel with a dropping funnel, 420 g (purity: 56%, 1.25 mol) of methacrylic acid 1-hydroxycarbonyl-1,1-difluoro-2-butyl ester obtained by a process disclosed in Japanese Laid-Open Patent Publication No. 2009-19199 and 7.50 g (0.11 mol, 0.01 eq) of dimethylformamide were dropped. Further, 452 g (3.79 mol, 3.0 eq) of thionyl chloride was added into the vessel at room temperature. The resulting solution was heated to 75° C. and stirred for 4 hours. The completion of the reaction was confirmed by $^{19}$F NMR. The reaction-completed solution was then subjected to distillation under a reduced pressure. With this, 255 g of methacrylic acid 1-chlorocarbonyl-1,1-difluoro-2-butyl ester was obtained (yield: 92%, purity: 98%).

Properties of methacrylic acid 1-chlorocarbonyl-1,1-difluoro-2-butyl ester $^1$H NMR (measurement solvent: deuterated chloroform, reference material: tetramethylsilane): δ=6.14 (s, 1H; =CH$_2$), 5.63 (s, 1H; =CH$_2$), 5.43 (m, 1H; CH—O), 19.2 (s, 3H; CH$_3$—C), 1.82 (m, 2H; CH$_2$ of CH—CH$_2$CH$_3$), 0.96 (t, J=7.6 Hz, 3H; CH$_3$ of CH—CH$_2$CH$_3$).

$^{19}$F NMR (measurement solvent: deuterated chloroform, reference material:
trichlorofluoromethane): δ=−108.10 (d, J=259Hz, 1F), −114.01 (d, J=259Hz, 1F).

Example 1

Production of 2,2-difluoro-3-methacryloyloxycarbonyl pentanoic acid 2-exo-norbornyl ester

[Chem. 40]

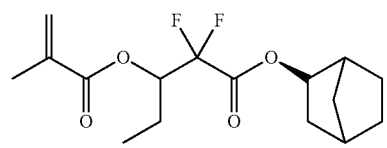

Into a 1 L glass flask with a dropping funnel, 95.0 g (0.847 mol, 1.2 eq) of exo-norboneol, 510 g of diisopropyl ether, 100 g (0.988 mol, 1.4 eq) of triethylamine and 1 g of antioxidant "Nonflex MBP" (manufactured by Seiko Chemical Co., Ltd.) were added. The resulting solution was cooled to 0° C. and stirred, followed by dropping thereto 170 g (purity: 99%, 0.706 mol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was dehydrated with magnesium sulfate, filtrated, and then, concentrated under a reduced pressure. The concentration residue was subjected to distillation under a reduced pressure. With this, 167 g of 2,2-difluoro-3-methacryloyloxycarbonyl pentanoic acid 2-exo-norbornyl ester was obtained as a colorless transparent liquid (yield: 75%, purity: 99%).

Properties of 2,2-difluoro-3-methacryloyloxycarbonyl pentanoic acid 2-exo-norbornyl ester $^1$H NMR (measurement solvent: deuterated chloroform, reference material: tetramethylsilane): δ=6.15 (m, 1H), 5.58 (m, 1H), 5.13 (m, 1H), 3.90 (m, 1H), 2.03 (m, 1H), 1.93 (m, 3H), 1.76-1.27 (m, 11H), 0.96 (m, 3H).
$^{19}$F NMR (measurement solvent: deuterated chloroform, reference material: trichlorofluoromethane): δ=−113.20 (d, 1F), −120.25 (d, 1F).

Example 2

Production of methacrylic acid 1-(n-butoxycarbonyl)-1,1-difluoro-2-butyl ester

[Chem. 41]

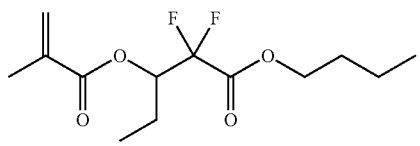

Into a 1 L glass flask with a dropping funnel, 62.8 g (0.847 mol, 1.2 eq) of n-butanol, 510 g of diisopropyl ether, 100 g (0.988 mol, 1.4 eq) of triethylamine and 1 g of antioxidant "Nonflex MBP" (manufactured by Seiko Chemical Co., Ltd.) were added. The resulting solution was cooled to 0° C. and stirred, followed by dropping thereto 170 g (purity: 99%, 0.706 mol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was dehydrated with magnesium sulfate, filtrated, and then, concentrated under a reduced pressure. The concentration residue was subjected to distillation under a reduced pressure. With this, 179 g of methacrylic acid 1-(n-butoxycarbonyl)-1,1-difluoro-2-butyl ester was obtained as a colorless transparent liquid (yield: 91%, purity: 99%).

Properties of methacrylic acid 1-(n-butoxycarbonyl)-1,1-difluoro-2-butyl ester $^1$H NMR (measurement solvent: deuterated chloroform, reference material: tetramethylsilane): δ=6.15 (m, 1H), 5.58 (m, 1H), 5.13 (m, 1H), 4.08 (m, 2H), 1.93 (m, 3H), 1.57 (m, 4H), 1.33 (m, 2H), 0.96 (m, 6H).
$^{19}$F NMR (measurement solvent: deuterated chloroform, reference material: trichlorofluoromethane): δ=−112.98 (d, 1F), −119.92 (d, 1F).

Example 3

Production of methacrylic acid 1-(4'-methoxy-1'-butoxycarbonyl)-1,1-difluoro-2-butyl ester

[Chem. 42]

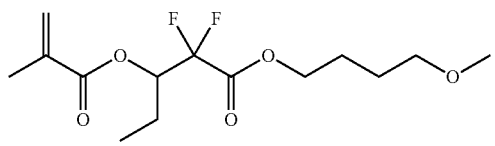

Into a 1 L glass flask with a dropping funnel, 6.3 g (0.847 mol, 1.2 eq) of 4-methoxy-1-butanol, 510 g of diisopropyl ether, 100 g (0.988 mol, 1.4 eq) of triethylamine and 1 g of antioxidant "Nonflex MBP" (manufactured by Seiko Chemical Co., Ltd.) were added. The resulting solution was cooled to 0° C. and stirred, followed by dropping thereto 170 g (purity: 99%, 0.706 mol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was dehydrated with magnesium sulfate, filtrated, and then, concentrated under a reduced pressure. The concentration residue was subjected to distillation under a reduced pressure. With this, 183 g of methacrylic acid 1-(4'-methoxy-1'-butoxycarbonyl)-1,1-difluoro-2-butyl ester was obtained as a colorless transparent liquid (yield: 88%, purity: 99%).

Properties of methacrylic acid 1-(4'-methoxy-1'-butoxycarbonyl)-1,1-difluoro-2-butyl ester $^1$H NMR (measurement solvent: deuterated chloroform, reference material: tetramethylsilane): δ=6.15 (m, 1H), 5.58 (m, 1H), 5.13 (m, 1H), 4.08 (m, 2H), 3.37 (m, 2H), 3.24 (m, 3H), 1.74 (m, 2H), 1.93 (m, 3H), 1.57 (m, 2H), 0.96 (m, 3H).
$^{19}$F NMR (measurement solvent: deuterated chloroform, reference material: trichlorofluoromethane): δ=−113.16 (d, 1F), −120.12 (d, 1F).

Example 4

Production of methacrylic acid 1-(1'H,1'H-heptafluoro-1-butoxycarbonyl)-1,1-difluoro-2-butyl ester

[Chem. 43]

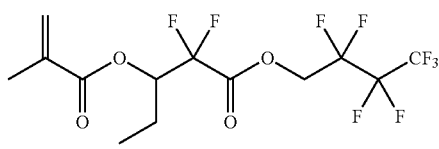

Into a 1 L glass flask with a dropping funnel, 13.0 g (65 mmol, 1.3 eq) of 1H,1H-heptafluoro-1-butyl alcohol, 51 g of diisopropyl ether, 6.56 g (65 mmol, 1.3 eq) of triethylamine and 0.1 g of antioxidant "Nonflex MBP" (manufactured by Seiko Chemical Co., Ltd.) were added. The resulting solution was cooled to 0° C. and stirred, followed by dropping thereto 12 g (purity: 99%, 50 mmol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was washed successively with 3 wt % aqueous sodium hydrogencarbonate solution and saturated sodium chloride solution, and then, concentrated under a reduced pressure. The concentration residue was subjected to distillation under a reduced pressure. With this, 16.6 g of methacrylic acid 1-(1'H,1'H-heptafluoro-1-butoxycarbonyl)-1,1-difluoro-2-butyl ester was obtained as a colorless transparent liquid (yield: 82%, purity: 99%).

Properties of methacrylic acid 1-(1'H,1'H-heptafluoro-1-butoxycarbonyl)-1,1-difluoro-2-butyl ester $^1$H NMR (measurement solvent: deuterated chloroform, reference material: tetramethylsilane): δ32 6.15 (m, 1H), 5.58 (m, 1H), 5.13 (m, 1H), 4.40 (m, 2H), 1.93 (m, 3H), 1.57 (m, 2H), 0.96 (m, 3H).
$^{19}$F NMR (measurement solvent: deuterated chloroform, reference material: trichlorofluoromethane): δ=−38.9 (s, 2F), −76.5 (t, 3F), −87.8 (q, 2F), −114.01 (d, 1F), −120.58 (d, 1F).

Example 5

Production of methacrylic acid 1-hexafluoroisopropoxycarbonyl-1,1-difluoro-2-butyl ester

[Chem. 44]

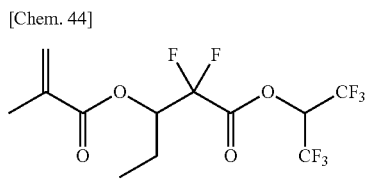 [SMILES: C=C(C)C(=O)OC(CC)C(F)(F)C(=O)OC(C(F)(F)F)C(F)(F)F]

Into a 1 L glass flask with a dropping funnel, 109.1 g (0.649 mol, 1.3 eq) of hexafluoroisopropanol, 510 g of diisopropyl ether, 65.6 g (0.649 mol, 1.3 eq) of triethylamine and 1 g of antioxidant "Nonflex MBP" (manufactured by Seiko Chemical Co., Ltd.) were added. The resulting solution was cooled to 0° C. and stirred, followed by dropping thereto 120 g (purity: 99%, 0.499 mol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was washed successively with 3 wt % aqueous sodium hydrogencarbonate solution and saturated sodium chloride solution, and then, concentrated under a reduced pressure. The concentration residue was subjected to distillation under a reduced pressure. With this, 158 g of methacrylic acid 1-hexafluoroisopropoxycarbonyl-1,1-difluoro-2-butyl ester was obtained as a colorless transparent liquid (yield: 85%, purity: 99%).

Properties of methacrylic acid 1-hexafluoroisopropoxycarbonyl-1,1-difluoro-2-butyl ester $^1$H NMR (measurement solvent: deuterated chloroform, reference material: tetramethylsilane): δ=6.15 (m, 1H), 5.59 (m, 1H), 5.58 (m, 1H), 5.13 (m, 1H), 1.93 (m, 3H), 1.57 (m, 2H), 0.96 (m, 3H).
$^{19}$F NMR (measurement solvent: deuterated chloroform, reference material: trichlorofluoromethane): δ=−76.0 (d, 6F), −114.21 (d, 1F), −120.46 (d, 1F).

Example 6

Production of methacrylic acid 1-pentafluorophenoxycarbonyl-1,1-difluoro-2-butyl ester

[Chem. 45]

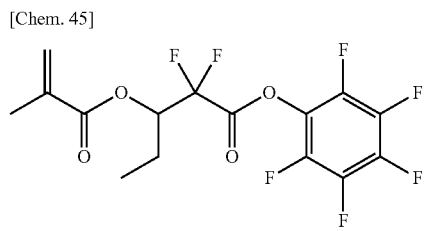 [SMILES: C=C(C)C(=O)OC(CC)C(F)(F)C(=O)Oc1c(F)c(F)c(F)c(F)c1F]

Into a 1 L glass flask with a dropping funnel, 12.0 g (65 mmol, 1.3 eq) of pentafluorophenol, 50 g of diisopropyl ether, 6.56 g (65 mmol, 1.3 eq) of triethylamine and 0.1 g of antioxidant "Nonflex MBP" (manufactured by Seiko Chemical Co., Ltd.) were added. The resulting solution was cooled to 0° C. and stirred, followed by dropping thereto 12 g (purity: 99%, 50 mmol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was washed successively with 3 wt % aqueous sodium hydrogencarbonate solution and saturated sodium chloride solution, and then, concentrated under a reduced pressure. The concentration residue was subjected to distillation under a reduced pressure. With this, 15.5 g of methacrylic acid 1-pentafluorophenoxycarbonyl-1,1-difluoro-2-butyl ester was obtained as a colorless transparent liquid (yield: 80%, purity: 99%).

Properties of methacrylic acid 1-pentafluorophenoxycarbonyl-1,1-difluoro-2-butyl ester $^1$H NMR (measurement solvent: deuterated chloroform, reference material: tetramethylsilane): δ=6.15 (m, 1H), 5.58 (m, 1H), 5.13 (m, 1H), 1.93 (m, 3H), 1.57 (m, 2H), 0.96 (m, 3H).
$^{19}$F NMR (measurement solvent: deuterated chloroform, reference material: trichlorofluoromethane): δ=−113.92 (d, 1F), −120.37 (d, 1F), −163.8 (d, 4F), −168.4 (m, 1F).

Example 7

Production of methacrylic acid 1-(1',1',2',2',3',3',3'a,7'a-octafluorooctahydro-4',7'-methano-1'H-5'-indeneoxycarbonyl)-1,1-difluoro-2-butyl ester

[Chem. 46]

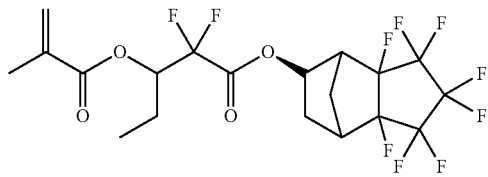

Into a 1 L glass flask with a dropping funnel, 19.2 g (64 mmol, 1.3 eq) of 1,1,2,2,3,3,3a,7a-octafluorooctahydro-4,7-methano-1H-indene-5-ol, 50 g of diisopropyl ether, 6.56 g (65 mmol, 1.3 eq) of triethylamine and 0.1 g of antioxidant "Nonflex MBP" (manufactured by Seiko Chemical Co., Ltd.) were added. The resulting solution was cooled to 0° C. and stirred, followed by dropping thereto 12 g (purity: 99%, 50 mmol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was washed successively with 3 wt% aqueous sodium hydrogencarbonate solution and saturated sodium chloride solution, and then, concentrated under a reduced pressure. The concentration residue was subjected to distillation under a reduced pressure. With this, 19.5 g of methacrylic acid 1-(1',1',2',2',3',3',3'a,7'a-octafluorooctahydro-4',7'-methano-1'H-5'-indeneoxycarbonyl)-1,1-difluoro-2-butyl ester was obtained as a pale yellow liquid (yield: 78%, purity: 99%).

Properties of methacrylic acid 1-(1',1',2',2',3',3',3'a,7'a-octafluorooctahydro-4',7'-methano-1'H-5'-indeneoxycarbonyl)-1,1-difluoro-2-butyl ester $^1$H NMR (measurement solvent: deuterated chloroform, reference material: tetramethylsilane): δ=6.15 (m, 1H), 5.58 (m, 1H), 5.13 (m, 1H), 3.90 (m, 1H), 2.29 (m, 1H), 1.93 (m, 3H), 1.76-1.30 (m, 7H), 0.96 (m, 3H).
$^{19}$F NMR (measurement solvent: deuterated chloroform, reference material: trichlorofluoromethane): δ=−113.25 (d, 1F), −120.31 (d, 1F), −121.20 (m, 1F), −121.42 (m, 1F), −121.88 (m, 4F), −134.77 (m, 2F).

Example 8

Production of methacrylic acid 1-(2'-hydroxy-1',1',1'-trifluoro-2'-trifluoromethyl-2'-pentoxycarbonyl)-1,1-difluoro-2-butyl ester

[Chem. 47]

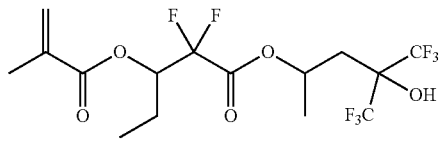

Into a 1 L glass flask with a dropping funnel, 147.0 g (0.650 mol, 1.3 eq) of 1,1,1-trifluoro-2-trifluoromethyl-2,4-pentanediol, 510 g of diisopropyl ether, 65.8 g (0.650 mol, 1.3 eq) of triethylamine and 1 g of antioxidant "Nonflex MBP" (manufactured by Seiko Chemical Co., Ltd.) were added. The resulting solution was cooled to 0° C. and stirred, followed by dropping thereto 120 g (purity: 99%, 0.499 mol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was washed successively with 3 wt% aqueous sodium hydrogencarbonate solution and saturated sodium chloride solution, and then, concentrated under a reduced pressure. The concentration residue was subjected to distillation under a reduced pressure. With this, 200 g of methacrylic acid 1-(2'-hydroxy-1',1',1'-trifluoro-2'-trifluoromethyl-2'-pentoxycarbonyl)-1,1-difluoro-2-butyl ester was obtained as a colorless transparent liquid (yield: 93%, purity: 98%).

Properties of methacrylic acid 1-(2'-hydroxy-1',1',1'-trifluoro-2'-trifluoromethyl-2'-pentoxycarbonyl)-1,1-difluoro-2-butyl ester $^1$H NMR (measurement solvent: deuterated chloroform, reference material: tetramethylsilane): δ=6.15 (m, 1H), 5.58 (m, 1H), 5.13 (m, 1H), 4.64 (m, 1H), 4.13 (m, 1H), 1.93 (m, 3H), 1.64 (m, 2H), 1.57 (m, 2H), 1.40 (m, 3H), 0.96 (m, 3H).
$^{19}$F NMR (measurement solvent: deuterated chloroform, reference material: trichlorofluoromethane): δ=−77.01 (q, 3F), −79.05 (q, 3F), −113.11 (d, 1F), −120.09 (d, 1F).

Example 9

Production of methacrylic acid 1-[(2'-trifluoromethanesulfonylamino)ethoxycarbonyl]-1,1-difluoro-2-butyl ester

[Chem. 48]

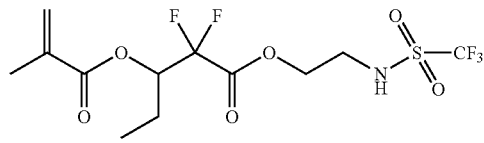

Into a 1 L glass flask with a dropping funnel, 125.5 g (0.650 mol, 1.3 eq) of (2-trifluoromethanesulfonylamino)ethanol, 512 g of diisopropyl ether, 65.8 g (0.650 mol, 1.3 eq) of triethylamine and 1 g of antioxidant "Nonflex MBP" (manufactured by Seiko Chemical Co., Ltd.) were added. The resulting solution was cooled to 0° C. and stirred, followed by dropping thereto 120 g (purity: 99%, 0.499 mol) of methacrylic acid 1-chlorocarbonyl-1,1-difluoro-2-butyl ester. The thus-obtained reaction solution was stirred for 1 hour at room temperature. The completion of the reaction was confirmed by $^{19}$F NMR. The reaction-completed solution was separated into an organic layer and an aqueous layer by the addition of 500 mL of water. The organic layer was washed successively with 3 wt% aqueous sodium hydrogencarbonate solution and saturated sodium chloride solution, and then, concentrated under a reduced pressure. The concentration residue was subjected to distillation under a reduced pressure. With this, 176 g of methacrylic acid 1-[(2'-trifluoromethanesulfonylamino)ethoxycarbonyl]-1,1-difluoro-2-butyl ester was obtained as a colorless transparent liquid (yield: 89%, purity: 97%).

Properties of methacrylic acid 1-[(2'-trifluoromethanesulfonylamino)ethoxycarbonyl]-1,1-difluoro-2-butyl ester $^1$NMR (measurement solvent: deuterated chloroform, reference material: tetramethylsilane): δ=6.99 (m, 1H), 6.15 (m, 1H), 5.58 (m, 1H), 5.13 (m, 1H), 4.34 (m, 2H), 2.93 (m, 2H), 1.93 (m, 3H), 1.57 (m, 2H), 0.96 (m, 3H).
$^{19}$F NMR (measurement solvent: deuterated chloroform, reference material: trichlorofluoromethane): δ=−78.9 (s, 3F), −113.01 (d, 1F), −120.13 (d, 1F).

[Synthesis of Polymers]

Example 10

Production of Fluorine-Containing Polymer (1)

[Chem. 49]

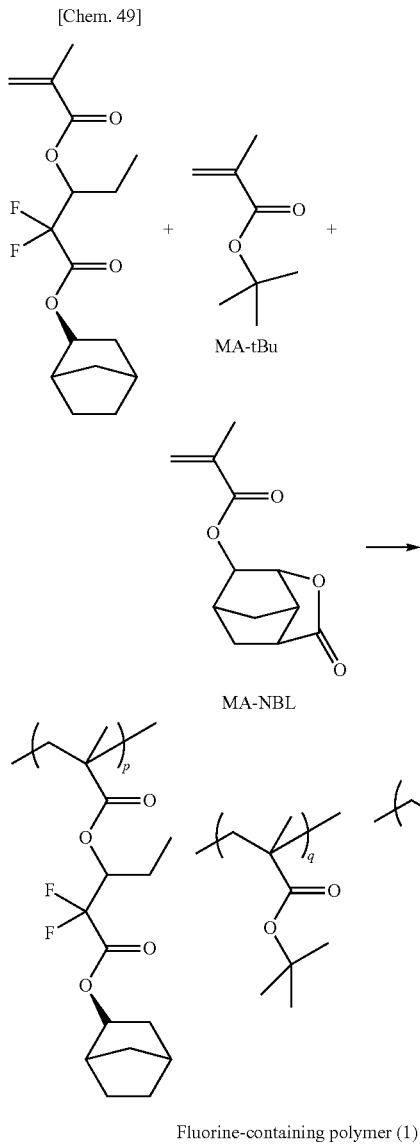

Fluorine-containing polymer (1)

Into a glass flask with a condenser, 3.17 g of 2,2-difluoro-3-methacryloyloxycarbonyl pentanoic acid 2-norbornyl ester, 1.66 g of MA-tBu (t-butyl methacrylate), 2.59 g of MA-NBL (manufactured by Daicel Corporation), 0.1 g of azobisbutyronitrile and 15 ml of methyl ethyl ketone were added. The flask was filled with nitrogen. The resulting solution was heated to 60° C. and stirred for 18 hours. After the completion of the reaction, the resultant solution was dropped into 60 ml of n-hexane to thereby form a precipitate by stirring. The precipitate was taken out and dried at 55° C. for 20 hours, thereby obtaining 5.6 g of a fluorine-containing polymer (1) as a white solid (yield: 75%). The repeating unit content ratio of the fluorine-containing polymer (1) was determined by NMR; and the molecular weight of the fluorine-containing polymer (1) was determined by gel permeation chromatography (GPC, standard material: polystyrene).

Example 11

Production of Fluorine-Containing Polymer (2)

[Chem. 50]

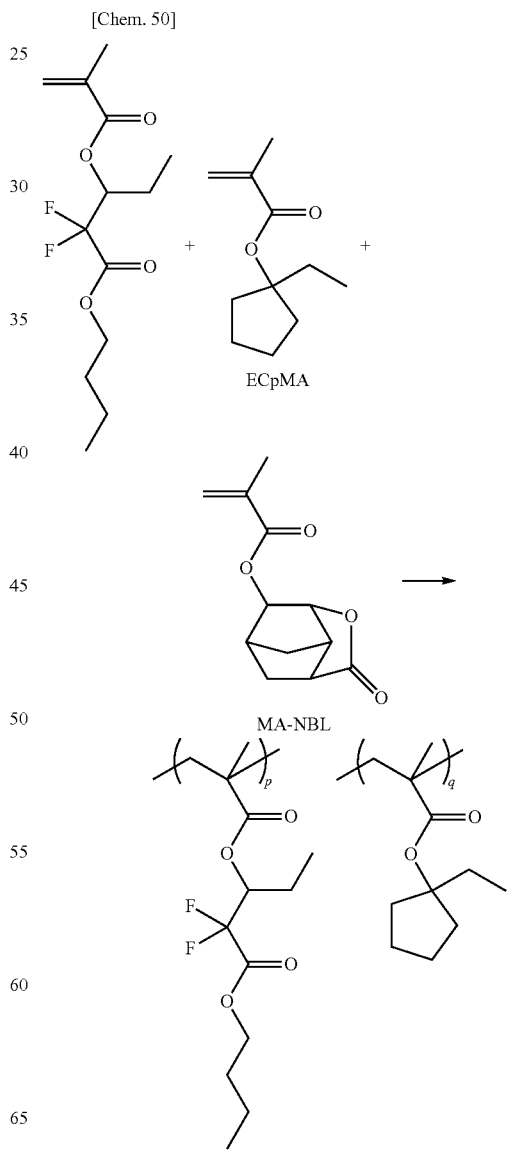

59

-continued

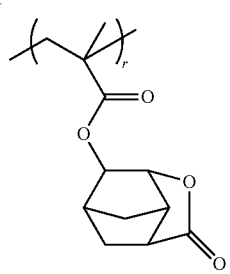

Fluorine-containing polymer (2)

A fluorine-containing polymer (2) was produced in the same manner as in Example 10, using methacrylic acid 1-(n-butoxycarbonyl)-1,1-difluoro-2-butyl ester, ECPMA (ethyl-cyclopentyl methacrylate, manufactured by Osaka Organic Chemical Industry Ltd.) and MA-NBL.

Example 12

Production of Fluorine-Containing Polymer (3)

[Chem. 51]

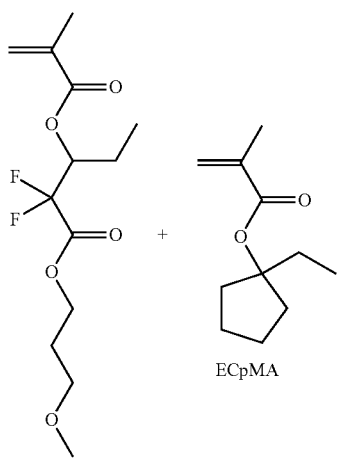

ECpMA

60

-continued

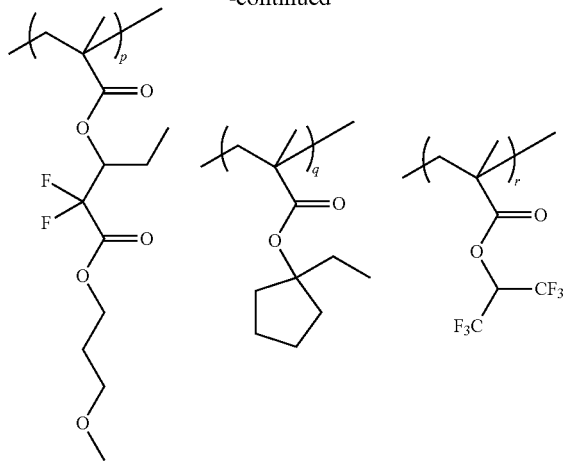

Fluorine-containing polymer (3)

A fluorine-containing polymer (3) was produced in the same manner as in Example 10, using methacrylic acid 1-(4'-methoxy-1'-butoxycarbonyl)-1,1-difluoro-2-butyl ester, ECPMA and HFIP-M (hexafluoroisopropyl methacrylate).

Example 13

Production of Fluorine-Containing Polymer (4)

[Chem. 52]

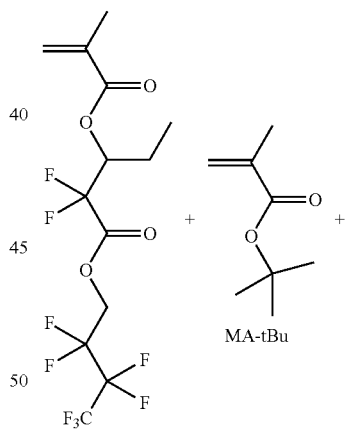

MA-tBu

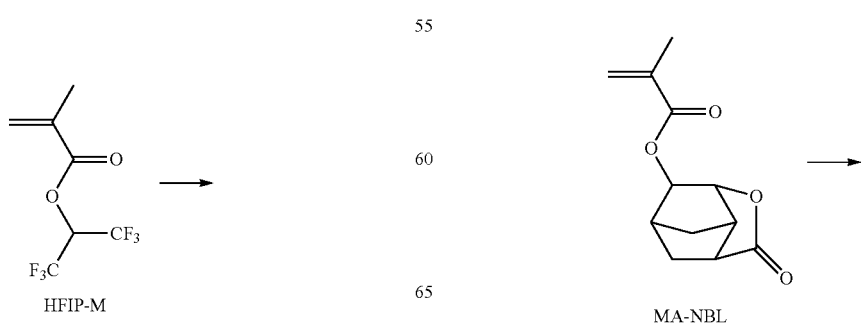

HFIP-M

MA-NBL

-continued

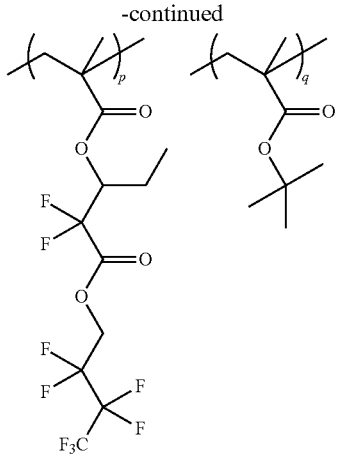

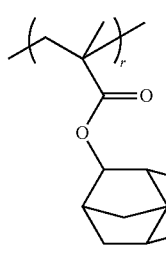

Fluorine-containing polymer (4)

A fluorine-containing polymer (4) was produced in the same manner as in Example 10, using methacrylic acid 1-(1'H,1'H-heptafluoro-1-butoxycarbonyl)-1,1-difluoro-2-butyl ester, MA-tBu and MA-NBL.

Example 14

Production of Fluorine-Containing Polymer (5)

[Chem. 53]

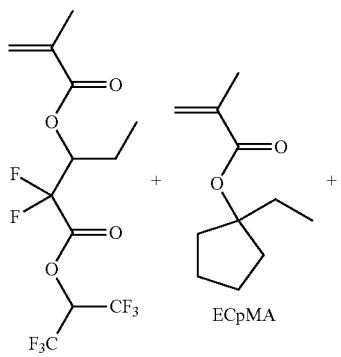

-continued

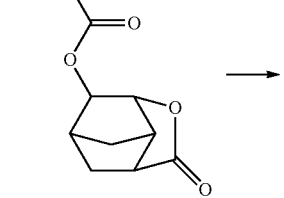

MA-NBL

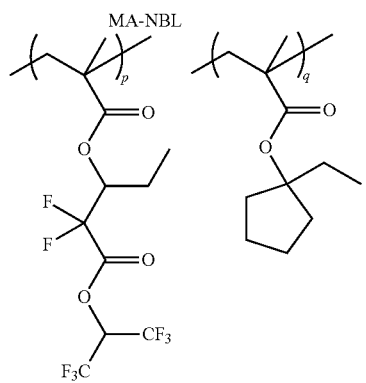

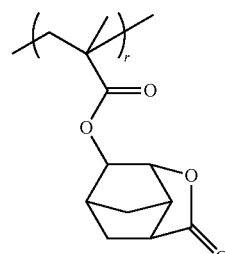

Fluorine-containing polymer (5)

A fluorine-containing polymer (5) was produced in the same manner as in Example 10, using methacrylic acid 1-hexafluoroisopropoxycarbonyl-1,1-difluoro-2-butyl ester, ECPMA and MA-NBL.

Example 15

Production of Fluorine-Containing Polymer (6)

[Chem. 54]

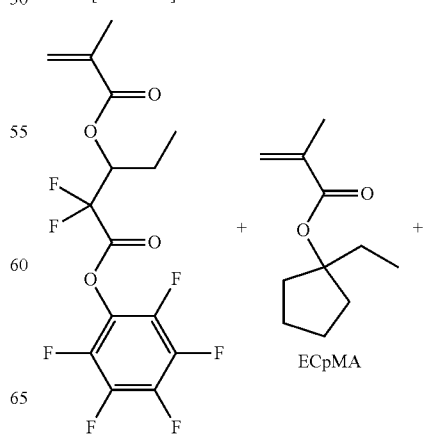

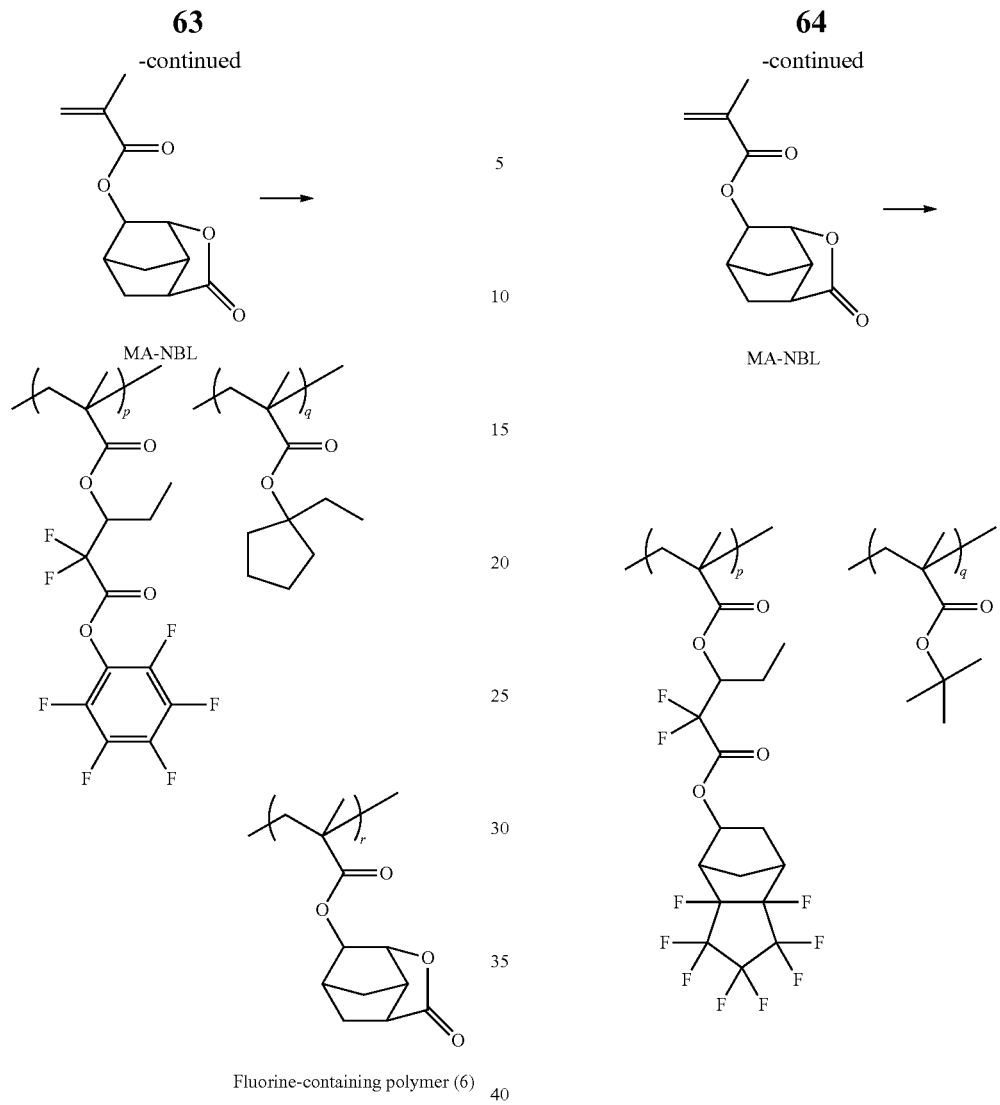

Fluorine-containing polymer (6)

A fluorine-containing polymer (6) was produced in the same manner as in Example 10, using methacrylic acid 1-pentafluorophenoxycarbonyl-1,1-difluoro-2-butyl ester, ECPMA and MA-NBL.

Example 16
Production of Fluorine-Containing Polymer (7)

[Chem. 55]

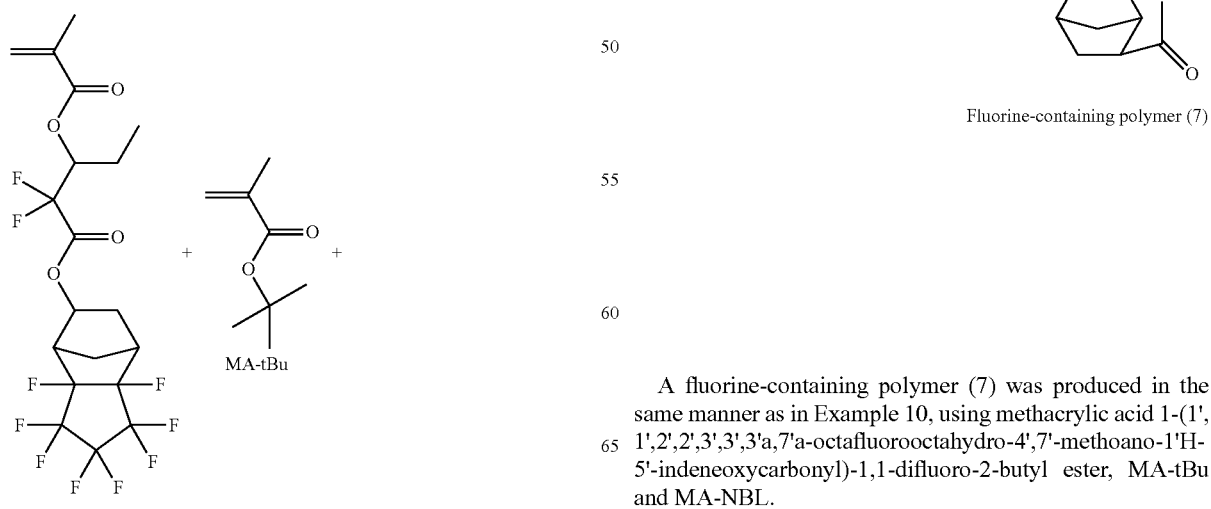

Fluorine-containing polymer (7)

A fluorine-containing polymer (7) was produced in the same manner as in Example 10, using methacrylic acid 1-(1', 1',2',2',3',3',3'a,7'a-octafluorooctahydro-4',7'-methoano-1'H-5'-indeneoxycarbonyl)-1,1-difluoro-2-butyl ester, MA-tBu and MA-NBL.

Example 17

Production of Fluorine-Containing Polymer (8)

[Chem. 56]

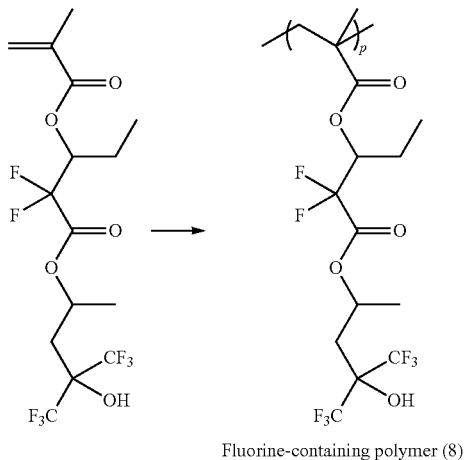

Fluorine-containing polymer (8)

A fluorine-containing polymer (8) was produced in the same manner as in Example 10, using methacrylic acid 1-(2'-hydroxy-1',1',1'-trifluoro-2'-trifluoromethyl-2'-pentoxycarbonyl)-1,1-difluoro-2-butyl ester.

Example 18

Production of Fluorine-Containing Polymer (9)

[Chem. 57]

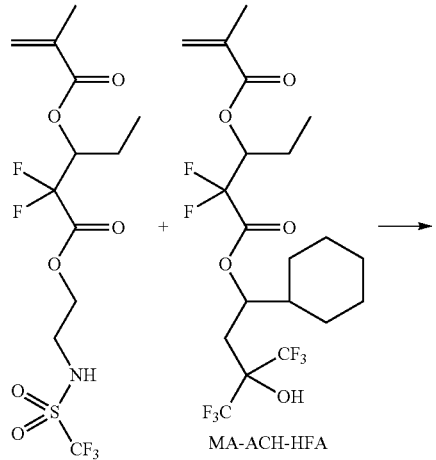

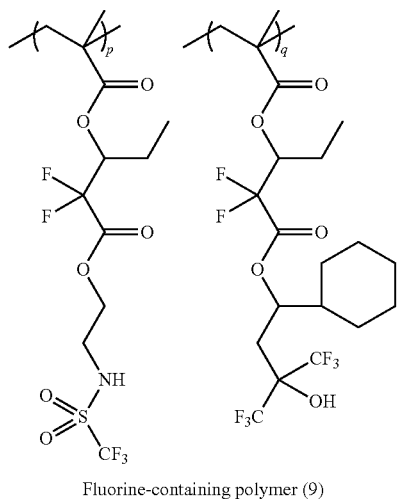

Fluorine-containing polymer (9)

A fluorine-containing polymer (9) was produced in the same manner as in Example 10, using methacrylic acid 1-[(2'-trifluoromethanesulfonylamino)ethoxycarbonyl]-1,1-difluoro-2-butyl ester and 1-cyclohexyl-4,4,4-trifluoro-3-(trifluoromethyebutane-1,3-diol (MA-ACH-HFA) obtained by a process disclosed in Japanese-Laid Open Patent Publication No. 2007-63255.

Example 19

Production of Fluorine-Containing Polymer (10)

[Chem. 58]

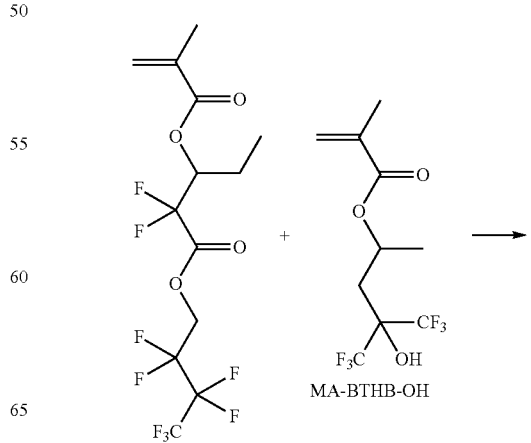

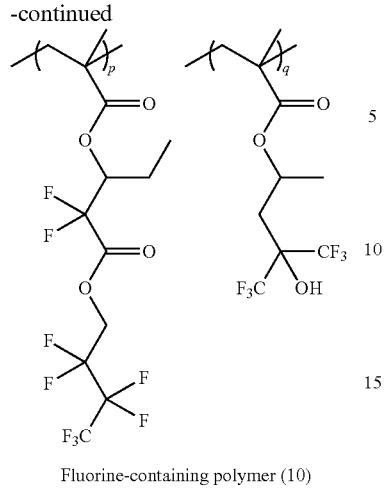

Fluorine-containing polymer (10)

A fluorine-containing polymer (10) was produced in the same manner as in Example 10, using methacrylic acid 1-(1'H,1'H-heptafluoro-1-butoxycarbonyl)-1,1-difluoro-2-butyl ester and 4,4,4-trifluoro-3-hydroxy-1-methyl-3-(trifluoromethyl)butyl 2-methacrylate (MA-BTHB-OH) obtained by a process disclosed in Japanese Laid-Open Patent Publication No. 2005-206587.

Example 20

Production of Fluorine-Containing Polymer (11)

[Chem. 59]

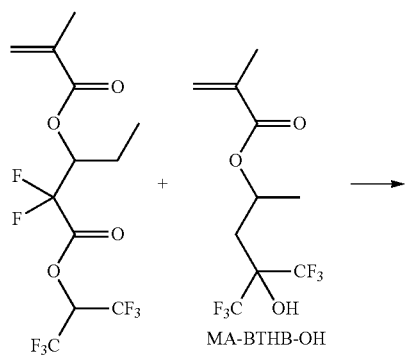

MA-BTHB-OH

Fluorine-containing polymer (11)

A fluorine-containing polymer (11) was produced in the same manner as in Example 10, using methacrylic acid 1-hexafluoroisopropoxycarbonyl-1,1-difluoro-2-butyl ester and MA-BTHB-OH.

Comparative Example 1

Production of Polymer (1)

[Chem. 60]

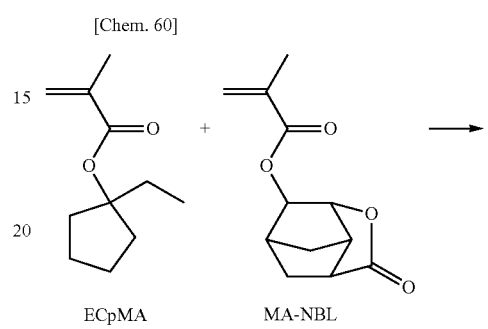

ECpMA                    MA-NBL

Polymer (1)

A polymer (1) was produced in the same manner as in Example 10, using ECpMA and MA-NBL.

Comparative Example 2

Production of Fluorine-Containing Polymer (12)

[Chem. 61]

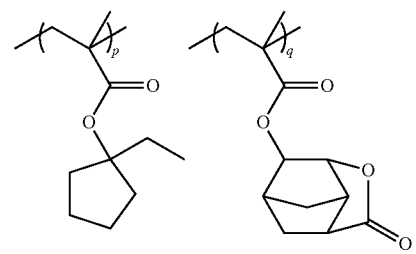

MA-BTHB-OH                Fluorine-containing polymer (12)

A fluorine-containing polymer (12) was produced in the same manner as in Example 10, using MA-BTHB-OH.

Comparative Example 3

Production of Fluorine-Containing Polymer (13)

[Chem. 62]

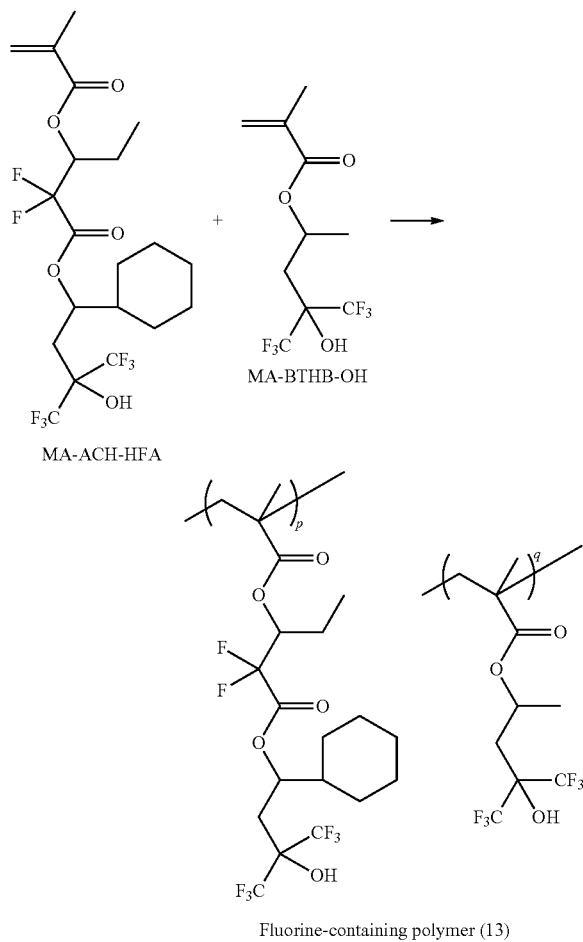

Fluorine-containing polymer (13)

A fluorine-containing polymer (13) was produced in the same manner as in Example 10, using MA-ACH-HFA and MA-BTHB-OH.

Reference Example 1

Production of Polymer (2) for Resist

[Chem. 63]

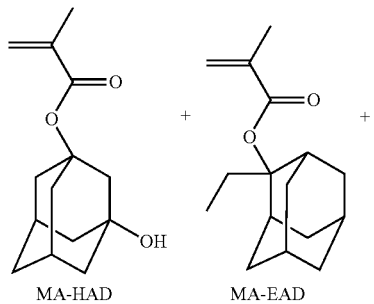

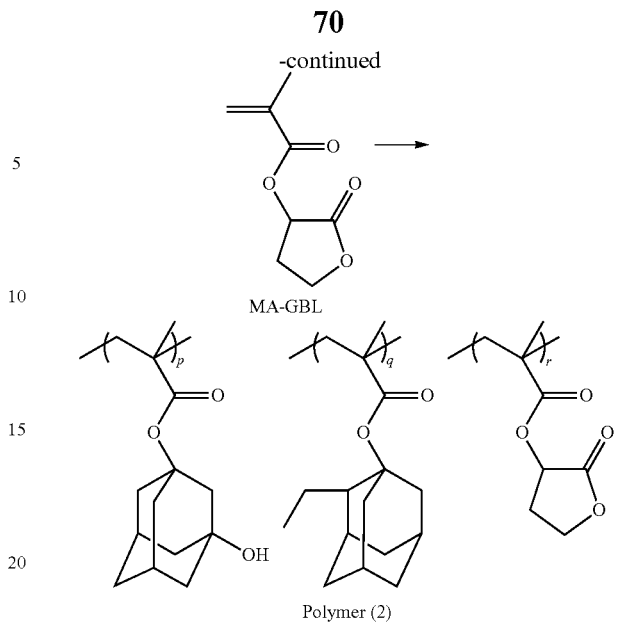

Polymer (2)

Within a glass flask, 12.0 g of MA-HAD (hydroxyadamantyl methacrylate), 10.8 g of MA-EAD (ethyladamantyl methacrylate) and 10.1 g of MA-GBL (γ-butyrolactone methacrylate) as monomers and 0.54 g of n-dodecylmercaptan (manufactured by Tokyo Chemical Industry Co., Ltd.) as a chain transfer agent were dissolved in 65.8 g of 2-butanone as a solvent. To the resulting solution, 1.35 g of AIBN (product name, 2,2'-azobis(isobutyronitrile), manufactured by Wako Pure Chemical Industries Ltd.) was added as a polymerization initiator. The solution was degassed under stirring and, after the introduction of nitrogen gas, was subjected to reaction at 75° C. for 16 hours. After the completion of the reaction, the resultant solution was dropped into 500.0 g of n-heptane to thereby form a white precipitate. The precipitate was filtered out and dried under a reduced pressure at 60° C. With this 29.6 g of a white solid (polymer (2)) was obtained (yield: 90%).

[Polymerization Results]

The polymers of Examples 10 to 20, Comparative Examples 1 to 3 and

Reference Example 1 were tested for the molecular weight. The molecular weight (mass-average molecular weight) of the polymer was measured by means of series connection of one column HLC-8320GPC and one column ALPHA-2500, each of which manufactured by Tosoh Corporation, with the use of tetrahydrofuran as a developing solvent. In the molecular weight measurement, a differential refractive index detector was used. Further, each of the polymers was also tested for the solubility by stirring 10 g of the polymer into 100 ml of propylene glycol monomethyl ether acetate (PGMEA) or 4-methyl-2-pentanol (MIBC). The solubility of the polymer was evaluated as "soluble" when it was possible to prepare a transparent polymer solution and form a uniform film from the polymer solution by spin coating and as "insoluble" when it was not possible to form a uniform film from the polymer solution.

The measurement test results of the composition, molecular weight and solubility of the polymers of Examples 10 to 20, Comparative Examples 1 to 3 and Reference Example 1 are indicated in TABLE 1.

TABLE 1

| Example/Comparative Example/Reference Example | Polymer | Composition (p/q/r) | Mw | Solubility PGMEA | Solubility MIBC |
|---|---|---|---|---|---|
| Example 10 | fluorine-containing polymer (1) | 30/35/35 | 12800 | soluble | soluble |
| Example 11 | fluorine-containing polymer (2) | 20/40/40 | 11500 | soluble | soluble |
| Example 12 | fluorine-containing polymer (3) | 30/40/30 | 13400 | soluble | soluble |
| Example 13 | fluorine-containing polymer (4) | 10/40/50 | 12500 | soluble | soluble |
| Example 14 | fluorine-containing polymer (5) | 20/50/30 | 9800 | soluble | soluble |
| Example 15 | fluorine-containing polymer (6) | 40/40/20 | 7900 | soluble | soluble |
| Example 16 | fluorine-containing polymer (7) | 5/60/35 | 8800 | soluble | insoluble |
| Example 17 | fluorine-containing polymer (8) | 100 | 7500 | soluble | soluble |
| Example 18 | fluorine-containing polymer (9) | 50/50 | 7600 | soluble | soluble |
| Example 19 | fluorine-containing polymer (10) | 30/70 | 8000 | soluble | soluble |
| Example 20 | fluorine-containing polymer (11) | 5/95 | 10200 | soluble | soluble |
| Comparative Example 1 | polymer (1) | 50/50 | 11100 | soluble | soluble |
| Comparative Example 2 | fluorine-containing polymer (12) | 100 | 9200 | soluble | soluble |
| Comparative Example 3 | fluorine-containing polymer (13) | 60/40 | 8900 | soluble | soluble |
| Reference Example 1 | polymer (2) | 30/35/35 | 11300 | soluble | insoluble |

[Preparation of Positive Resist Solutions and Formation of Resist Films]

A resist solution (FR-1) was prepared by dissolving the fluorine-containing polymer (1) into propylene glycol monomethyl ether acetate (PGMEA) in such a manner that the resulting solution had a solid content of 14%, followed by dissolving therein 5 parts by mass of triphenylsulfonium triflate (TPS 105) manufactured by Midori Kagaku Co., Ltd. as a photoacid generator and 0.15 parts by weight of trioctylamine as a basic compound per 100 parts by weight of the fluorine-containing polymer (1). Resist solutions (FR-2), (FR-3), (FR-4), (FR-5), (FR-6), (FR-7) and (R-1) were prepared in the same manner as above using the fluorine-containing polymers (2) to (7) and the polymer (1), respectively.

Similarly, a resist solution (FR-4') was prepared by dissolving the fluorine-containing polymer (4) into propylene glycol monomethyl ether acetate (PGMEA) in such a manner that the resulting solution had a solid content of 14%, followed by dissolving therein 5 parts by mass of nonafluorobutane triphenylsulfonium sulfonate as a photoacid generator and 0.15 parts by weight of isopropanol amine as a basic compound per 100 parts by weight of the fluorine-containing polymer (4).

The above-prepared resist solutions were filtered by membrane filters of pore size 0.2 spin coated on silicon wafers (diameter: 200 mm, the same applies throughout the examples) and dried at 100° C. for 90 seconds, thereby forming resin films (resist film) with a thickness of about 250 nm on the silicon wafers.

The resist films formed by applying the resist solutions (FR-1), (FR-2), (FR-3), (FR-4), (FR-4'), (FR-5), (FR-6), (FR-7) and (R-1) to the silicon wafers were subjected to the following alkali developer solubility test, advancing/receding contact angle test and exposure resolution test.

[Alkali Developer Solubility Test]

The rate of dissolution of the resin film (resist film) formed on the silicon wafer into an aqueous solution of 2.38 mass % tetramethylammonium hydroxide (alkali developer) was measured at 20° C. with the use of a resist development analyzer RDA-790 (manufactured by Litho Tech Japan Corporation). As shown in TABLE 2, none of the resist films formed from the above resist solutions was dissolved before the exposure.

[Advancing/Receding Contact Angle Test]

The advancing and receding contact angles of water drops relative to the resin film (resist film) formed on the silicon wafer was measured at 20° C. by extension/contraction method with the use of a contact angle meter CA-X manufactured by Kyowa Interface Science Co., Ltd. As shown in TABLE 2, each of the resist films formed from the resist solutions (FR-1), (FR-2), (FR-3), (FR-4), (FR-4'), (FR-5), (FR-6) and (FR-7) according to the present invention had a high receding contact angle. On the other hand, the resist film formed from the comparative resist solution (R-1) had a receding contact angle lower than that required for use as liquid immersion resist.

[Exposure Resolution Test]

The resin film (resist film) formed on the silicon wafer was exposed to 193 nm ultraviolet radiation through a photomask. The photomask had a pattern of 1:1 line-and-space ratio with a dimension of 130 nm (130 nm 1L/1S pattern). The exposed resist film was subjected post exposure baking at 120° C. and developed at 22° C. for 1 minute with an aqueous solution of 2.38 mass % tetramethylammonium hydroxide. Each of the resist films formed from the resist solutions (FR-1), (FR-2), (FR-3), (FR-4), (FR-4'), (FR-5), (FR-6), (FR-7) and (R-1)

was patterned into a high-resolution shape. There were not detected any defects such as poor substrate adhesion, poor film formation, poor development and poor etching resistance. Further, the section of the 130 nm 1L/1S pattern resolved by the optimal expose amount was observed with a scanning electron microscope. The degree of deformation of the resist pattern from the rectangular shape was evaluated based on the observation result. In each of the cases of using the resist solutions (FR-1), (FR-2), (FR-3), (FR-4), (FR-4'), (FR-5), (FR-6), (FR-7) and (R-1), the resist pattern was rectangular with no stretched head and no deformation due to residue.

The above test results are summarized in TABLE 2.

TABLE 2

| Invention/ Comparative Example | Resist solution | Polymer | Dissolution rate (nm/sec) | Contact angle advancing | Contact angle receding | Rectangular shape |
|---|---|---|---|---|---|---|
| Invention | FR-1 | fluorine-containing polymer (1) | 0 | 90 | 74 | rectangular |
| Invention | FR-2 | fluorine-containing polymer (2) | 0 | 88 | 72 | rectangular |
| Invention | FR-3 | fluorine-containing polymer (3) | 0 | 83 | 71 | rectangular |
| Invention | FR-4 | fluorine-containing polymer (4) | 0 | 90 | 75 | rectangular |
| Invention | FR-4' | fluorine-containing polymer (4) | 0 | 89 | 73 | rectangular |
| Invention | FR-5 | fluorine-containing polymer (5) | 0 | 93 | 80 | rectangular |
| Invention | FR-6 | fluorine-containing polymer (6) | 0 | 92 | 78 | rectangular |
| Invention | FR-7 | fluorine-containing polymer (7) | 0 | 99 | 83 | rectangular |
| Comparative Example | R-1 | polymer (1) | 0 | 86 | 54 | rectangular |

FR-4': Nonafluorobutane triphenylsulfonium sulfonate was used as a photoacid generator.

[Preparation of Top Coat Solutions and Formation of Top Coat Films]

A uniform and transparent solution was prepared (as a top coat solution (T-1)) by dissolving 100 parts by mass of the fluorine-containing polymer (8) of Example 17 into 900 parts by mass of 4-methyl-2-pentanol (MIBC) as a solvent. Similarly, uniform and transparent solutions were prepared from the fluorine-containing polymers of Examples 18 to 20 and Comparative Examples 2 and 3 and adopted as top coat solutions (T-2), (T-3), (T-4), (TR-1) and (TR-2) as shown in TABLE 3.

The above-prepared top coat solutions were filtered by membrane filters (pore size: 0.2 μm), spin coated on silicon wafers by a spinner at a rotation speed of 1500 rpm and dried on a hot plate at 80° C. for 90 seconds, thereby forming resin films (top coat film) with a thickness of about 50 nm on the silicon wafers.

[Reference Resist Film]

As a reference for top coat test, a silicon wafer with a reference resist film was produced by the following procedure. A resist solution (RR-1) was prepared by dissolving the resist polymer (polymer (2)) of Reference Example 1 into propylene glycol monomethyl ether acetate (PGMEA) in such a manner that the resulting solution had a solid content of 12%, and then, adding thereto 5 parts by mass of nonafluorobutane triphenylsulfonium sulfonate as a photoacid generator and 1 parts by weight of isopropanol amine as a basic compound per 100 parts by weight of the polymer.

The prepared resist solution (RR-1) was filtered by a membrane filter of pore size 0.2 μm, spin coated on the silicon wafer and dried at 100° C. for 90 seconds. As a result, the resist film (reference resist film) was formed with a thickness of about 250 nm on the silicon wafer.

The top coat films formed by applying the top coat solutions (T-1), (T-2), (T-3), (T-4), (TR-1) and (TR-2) to the silicon wafers were subjected to the following advancing/receding contact angle test and alkali developer solubility test.

[Advancing/Receding Contact Angle Test]

The advancing and receding contact angles of the top coat film were measured in the same manner as those of the resist film. As shown in TABLE 3, each of the top coat films formed from the top coat solutions (T-1), (T-2), (T-3) and (T-4) according to the present invention had a higher receding contact angle than those of not only the reference resist film (RR-1, receding contact angle: 47 degrees) but also the comparative top coat films (formed from the top coat solutions (TR-1) and (TR-2)).

[Alkali Developer Solubility Test]

The rate of dissolution of the top coat film formed on the silicon wafer into an aqueous solution of 2.38 mass % tetramethylammonium hydroxide (alkali developer) was measured at 20° C. with the use of a resist development analyzer RDA-790 (manufactured by Litho Tech Japan Corporation). As shown in TABLE 3, the dissolution rate of the top coat films of Comparative Examples was too low or too high. The top coat films, formed from the top coat solutions (T-1), (T-2), (T-3) and (T-4) each containing the fluorine-containing polymer of the present invention, had an adequate dissolution rate.

The above test results are summarized in TABLE 3.

TABLE 3

| Invention/<br>Comparative Example<br>Reference Example | Top coat/<br>resist<br>solution | Polymer | Contact angle | | Dissolution<br>rate<br>(nm/sec) |
|---|---|---|---|---|---|
| | | | advancing | receding | |
| Invention | T-1 | fluorine-containing polymer (8) | 89 | 74 | 670 |
| Invention | T-2 | fluorine-containing polymer (9) | 87 | 70 | 350 |
| Invention | T-3 | fluorine-containing polymer (10) | 94 | 76 | 290 |
| Invention | T-4 | fluorine-containing polymer (11) | 102 | 86 | 905 |
| Comparative Example | TR-1 | fluorine-containing polymer (12) | 88 | 65 | — |
| Comparative Example | TR-2 | fluorine-containing polymer (13) | 98 | 67 | 1200 |
| Reference Example | RR-1 | polymer (2) | 76 | 47 | 25 |

RR-1: Resist solution prepared from the polymer (2) (Reference Example 1).

[Formation of Two-Layer Resist/Top Coat Resin Films]

The resist solution (RR-1) was spin coated on a silicon wafer by a spinner and dried on a hot plate at 100° C. for 90 seconds, thereby forming a reference resist film with a thickness of about 150 nm. The top coat solution (T-1) was filtered by a membrane filter (pore size: 0.2 µm), spin coated on the resist film by a spinner and dried on a hot plate at 80° C. for 90 seconds, thereby forming a top coat film on the resist film to obtain a two-layer resin film with a total thickness of about 200 nm (a two-layer film of the resist film and the top coat film).

Similarly, two-layer resin films each having a total thickness of about 200 nm were obtained by applying reference resist films to silicon wafers and then foaming thereon top coat films from the top coat solutions (T-2), (T-3) and (T-4) and the comparative top coat solutions (TR-1) and (TR-2).

The two-layer resin films formed on the silicon wafers were subjected to the following pure-water immersion treatment test and exposure resolution test.

[Pure-Water Immersion Treatment Test]

Each of the two-layer resin films (the two-layer resist/top coat films) formed on the silicon wafers, 20 samples for each type, was immersed in 20 ml of pure water at 20° C. for 10 minutes. The resulting eluate solution was extracted and analyzed by ion chromatography to examine the presence or absence of any eluted substance in the solution. Except for the case of using no top coat film, there were not detected any peaks attributed to the photoacid generator and decomposition products thereof. The elution of the resist components into water was thus prevented by the formation of the top coat film.

[Exposure Resolution (Pattern Formation) Test]

Each of the two-layer resin films (the two-layer resist/top coat films) formed on the silicon wafers by pre-baking at 80° C. for 90 seconds was exposed to 193 nm wavelength radiation through a photomask. After the exposure, pure water was dropped onto the resist film while rotating the silicon wafer. The resin film was then subjected to post exposure baking at 120° C. for 60 seconds and developed with an alkali developer. As the alkali developer, an aqueous solution of 2.38 mass % tetramethylammonium hydroxide was used. The thus-obtained resist pattern was observed with a scanning electron microscope. The degree of deformation of the resist pattern from the rectangular shape was evaluated based on the observation result. In each of the cases of using the top coat solutions (T-1), (T-2), (T-3) and (T-4), the resist pattern was rectangular with no stretched head and no deformation due to residue.

The above test results are indicated in TABLE 4.

TABLE 4

| Invention/<br>Comparative<br>Example | Top coat<br>solution | Resist<br>solution | Pure-water<br>immersion test<br>result | Resist<br>resolution |
|---|---|---|---|---|
| Invention | T-1 | RR-1 | ○ | rectangular |
| Invention | T-2 | RR-1 | ○ | rectangular |
| Invention | T-3 | RR-1 | ○ | rectangular |
| Invention | T-4 | RR-1 | ○ | rectangular |
| Comparative Example | none | RR-1 | X | poor pattern formation with large stretched head |
| Comparative Example | TR-1 | RR-1 | ○ | rectangular |
| Comparative Example | TR-2 | RR-1 | ○ | rectangular |

Pure-water immersion test result: "○" when PAG elution was not detected, "X" when PAG elution was detected.

As described above, the fluorine-containing polymer of the present invention is useful as a constituent component for liquid immersion lithography resist composition and top coat compositions.

The invention claimed is:

1. A fluorine-containing polymer comprising a repeating unit (a) of the following general formula (2) and having a mass-average molecular weight of 1,000 to 1,000,000,

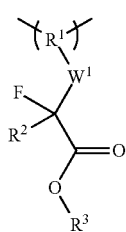

(2)

where $R^1$ represents one of the following formulas:

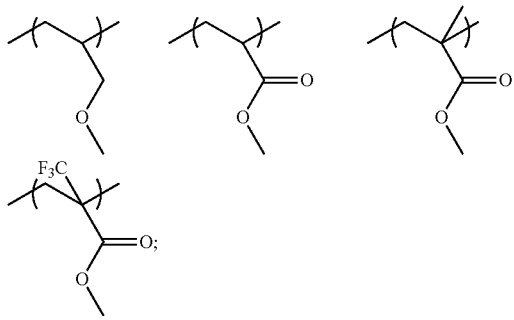

$R^2$ represents a fluorine atom or a trifluoromethyl group;
$R^8$ represents a substituted or unsubstituted alkyl group of the general formula (4) or an aryl group:

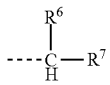

(4)

where $R^6$ and $R^7$ each independently represent a hydrogen atom, a substituted or unsubstituted alkyl or aryl group; and $R^6$, $R^7$ and a carbon atom in the general formula (4) may be bonded together to form an alicyclic hydrocarbon group;
any number of hydrogen atoms in $R^8$ may be substituted with a halogen atom, a hydroxyl group, an alkyl group, a fluorine-containing alkyl group or an aryl group;
any methylene group in $R^8$ except for that containing the carbon atom represented by C in the general formula (4) may be replaced by a carbonyl group (C=O), an ether group (O), an imide group (NH), a thioether group (S), a sulfinyl group (SO) or a sulfonyl group ($SO_2$);
$W^1$ represents a divalent linking group having a main skeleton formed by one atomic group, or two or more atomic groups in combination, selected from the group consisting of a single bond, substituted or unsubstituted methylene groups, divalent cyclic alkyl groups, divalent aryl groups, substituted or unsubstituted condensed polycyclic aromatic groups, divalent heterocyclic groups, a carbonyl group, an ether group, an ester bond, an oxycarbonyl bond, a thioether group, an amide bond, a sulfonamide bond, an urethane bond and an urea bond;
the linking group may have a plurality of atomic groups of the same kind;
any number of hydrogen atoms bonded to any carbon atom in the linking group may be substituted with a fluorine atom; and
any atoms in the linking group may be bonded together to form a ring structure.

2. The fluorine-containing polymer according to claim 1, wherein $R^2$ is a fluorine atom.

3. The fluorine-containing polymer according to claim 1, further comprising a repeating unit (c) formed by cleavage of a polymerizable double bond of a copolymerizable monomer selected from the group consisting of maleic anhydride, acrylic acid esters, fluorine-containing acrylic acid esters, methacrylic acid esters, fluorine-containing methacrylic acid esters, styrenic compounds, fluorine-containing styrenic compounds, vinyl ethers, fluorine-containing vinyl ethers, allyl ethers, fluorine-containing allyl ethers, olefins, fluorine-containing olefins, norbornene compounds, fluorine-containing norbornene compounds, sulfur dioxide, vinyl silanes, vinyl sulfonic acids and vinyl sulfonic acid esters and each having none of an acid-labile group and an alcoholic hydroxyl group.

4. The fluorine-containing polymer according to claim 1, further comprising a repeating unit of the general formula (5):

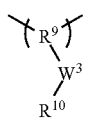

(5)

where $R^9$ represents one of the following formulas:

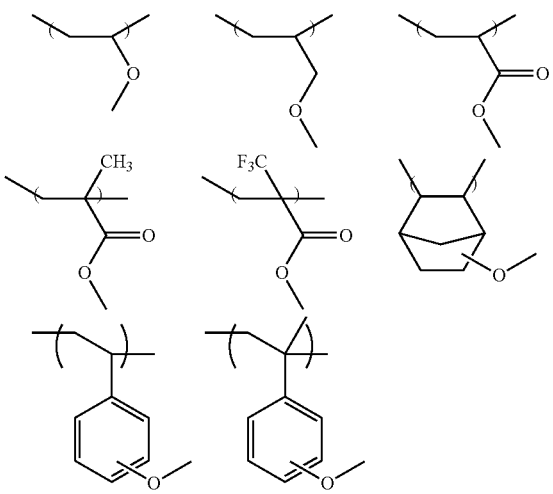

$R^{10}$ represents an acid-labile protecting group; and
$W^3$ represents a divalent linking group having a main skeleton formed by one atomic group, or two or more atomic groups in combination, selected from the group consisting of a single bond, substituted or unsubstituted methylene groups, divalent cyclic alkyl groups, divalent aryl group, substituted or unsubstituted condensed polycyclic aromatic groups, divalent heterocyclic groups, a carbonyl group, an ether group, a ester bond, an oxycarbonyl bond, a thioether group, an amide bond, a sulfonamide bond, an urethane bond and an urea bond;
the linking group may have a plurality of atomic groups of the same kind;
any number of hydrogen atoms bonded to any carbon atom in the linking group may be substituted with a fluorine atom; and
any atoms in the linking group may be bonded together to form a ring structure.

5. A positive resist composition solution comprising at least the fluorine-containing polymer according to claim 4, a photoacid generator and a solvent.

6. A pattern formation method, comprising at least: applying the resist composition solution according to claim 5 to a substrate; heat treating the substrate, thereby forming a resist film from the resist composition solution; exposing the resist film to high energy ray radiation of 300 nm or less wavelength or electron beam radiation through a photomask; heat treating the exposed resist film; and developing the exposed and heat treated resist film.

7. A top coat composition comprising at least the fluorine-containing polymer according to claim 1.

8. A top coat composition solution comprising at least the fluorine-containing polymer according to claim 1 and a solvent.

9. The top coat composition solution according to claim 8, wherein the solvent is one kind of solvent, or a mixed solvent of two or more kinds of solvents, selected from the group consisting of $C_5$-$C_{20}$ cyclic or chain hydrocarbons, $C_1$-$C_{20}$ hydrocarbon alcohols, partially fluorinated $C_5$-$C_{20}$ cyclic or chain hydrocarbons, and partially fluorinated $C_1$-$C_{20}$ hydrocarbon alcohols.

10. The top coat composition solution according to claim 9, wherein the solvent is a mixed solvent of 50 to 99.9 mass % of a $C_5$-$C_{20}$ hydrocarbon and 0.1 to 50 mass % of a $C_1$-$C_{20}$ hydrocarbon alcohol.

11. The top coat composition solution according to claim 8, wherein the solvent or the mixed solvent has a boiling point of 70 to 170° C.

12. The top coat composition solution according to claim 8, wherein the top coat composition solution is used for liquid immersion lithography.

13. A pattern formation method, comprising at least:
applying a positive resist composition solution to a substrate;
heat treating the substrate, thereby forming a resist film;
forming a top coat film on a surface of the resist film to provide a multilayer film in which the resist film and the top coat film are laminated on the substrate;
exposing the multilayer film to high energy ray radiation of 300 nm or less wavelength or electron beam radiation;
heat treating the exposed multilayer film; and
developing the exposed and heat treated multilayer film,
wherein the top coat film is of the top coat composition according to claim 7.

14. The pattern formation method according to claim 13, wherein the developing includes removing the top coat film substantially simultaneously with developing the resist film with an alkali developer.

15. A fluorine-containing unsaturated carboxylic acid ester of the following general formula (1):

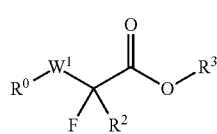

where $R^0$ represents one of the following formulas:

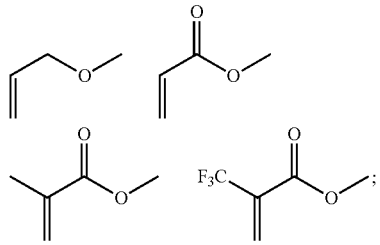

$R^2$ represents a fluorine atom or a trifluoromethyl group;

$R^3$ represents a substituted or unsubstituted alkyl group of the general formula (4) or an aryl group:

where $R^6$ and $R^7$ each independently represent a hydrogen atom, a substituted or unsubstituted alkyl or aryl group; and $R^6$, $R^7$ and a carbon atom in the general formula (4) may be bonded together to form an alicyclic hydrocarbon group;

any number of hydrogen atoms in $R^3$ may be substituted with a halogen atom, a hydroxyl group, an alkyl group, a fluorine-containing alkyl group or an aryl group;

any methylene group in $R^3$ except for that containing the carbon atom represented by C in the general formula (4) may be replaced by a carbonyl group (C=O), an ether group (O), an imide group (NH), a thioether group (S), a sulfinyl group (SO) or a sulfonyl group ($SO_2$);

$W^1$ represents a divalent linking group having a main skeleton formed by one atomic group, or two or more atomic groups in combination, selected from the group consisting of a single bond, substituted or unsubstituted methylene groups, divalent cyclic alkyl groups, divalent aryl groups, substituted or unsubstituted condensed polycyclic aromatic groups, divalent heterocyclic groups, a carbonyl group, an ether group, an ester bond, an oxycarbonyl bond, a thioether group, an amide bond, a sulfonamide bond, an urethane bond and an urea bond;

the linking group may have a plurality of atomic groups of the same kind;

any number of hydrogen atoms bonded to any carbon atom in the linking group may be substituted with a fluorine atom; and any atoms in the linking group may be bonded together to form a ring structure.

16. The fluorine-containing unsaturated carboxylic acid ester according to claim 15, wherein $R^2$ is a fluorine atom.

17. The pattern formation method according to claim 13, wherein the positive resist composition solution contains propylene propylene glycol monomethyl ether acetate as a solvent.

18. The fluorine-containing polymer according to claim 1, wherein $W^1$ represents one of the following formulas

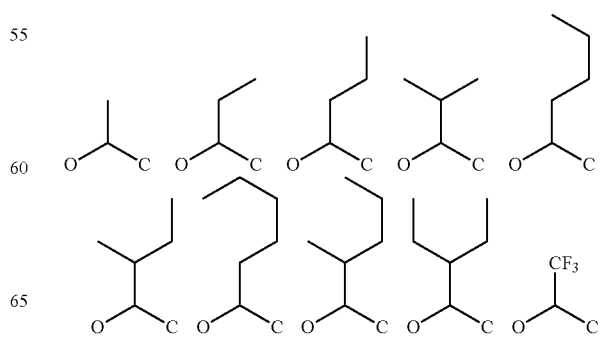

-continued
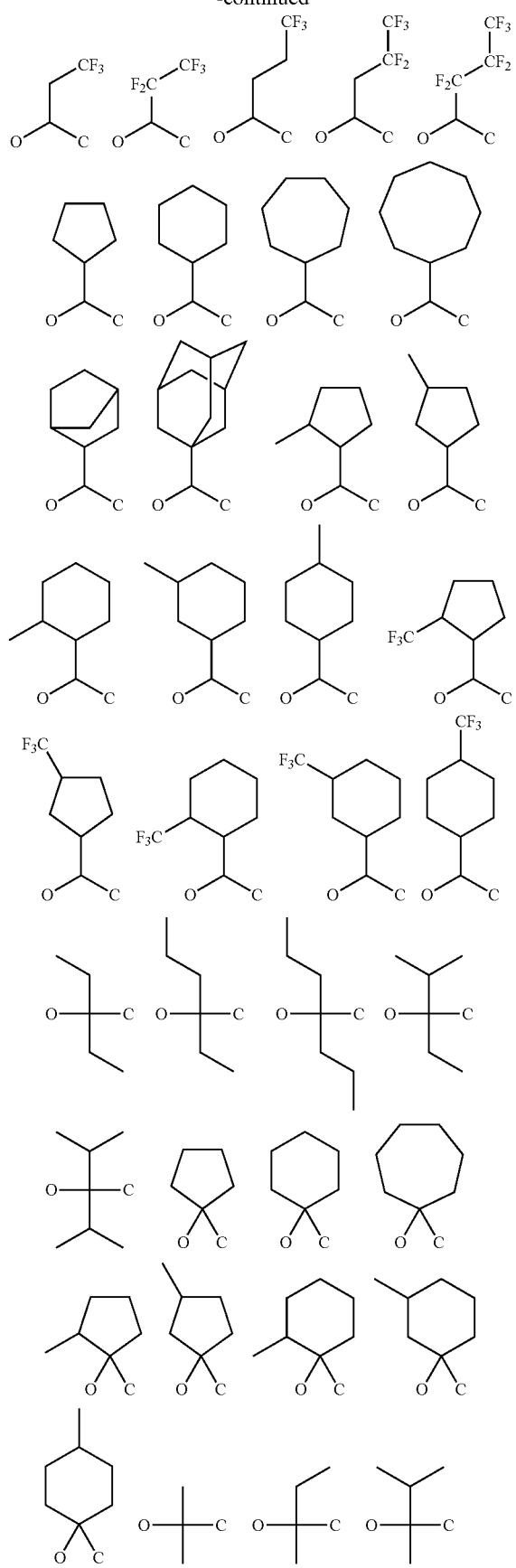
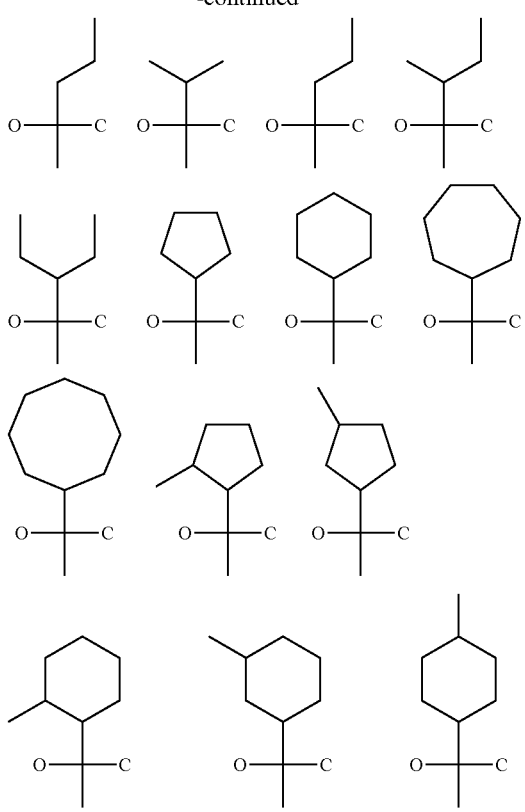
where O and C indicate an oxygen atom and a carbon atom located adjacent to the substituted methylene group.
19. The fluorine-containing unsaturated carboxylic acid ester according to claim 15, wherein $W^1$ represents one of the following formulas
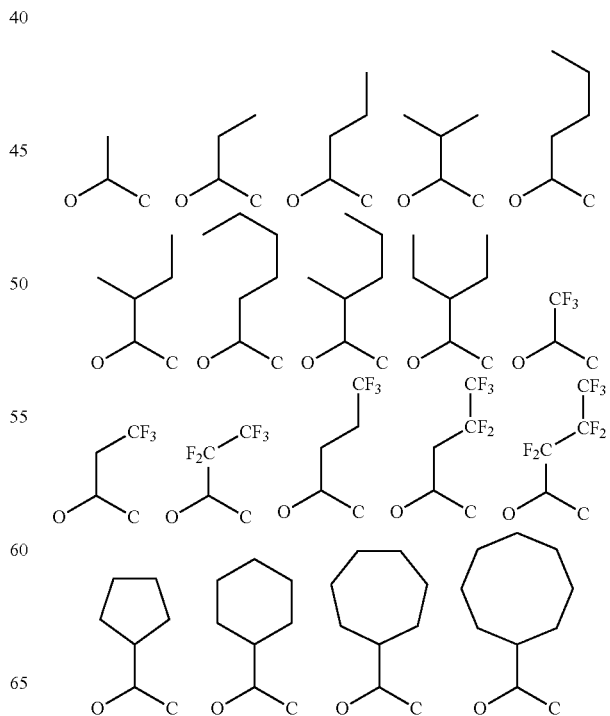

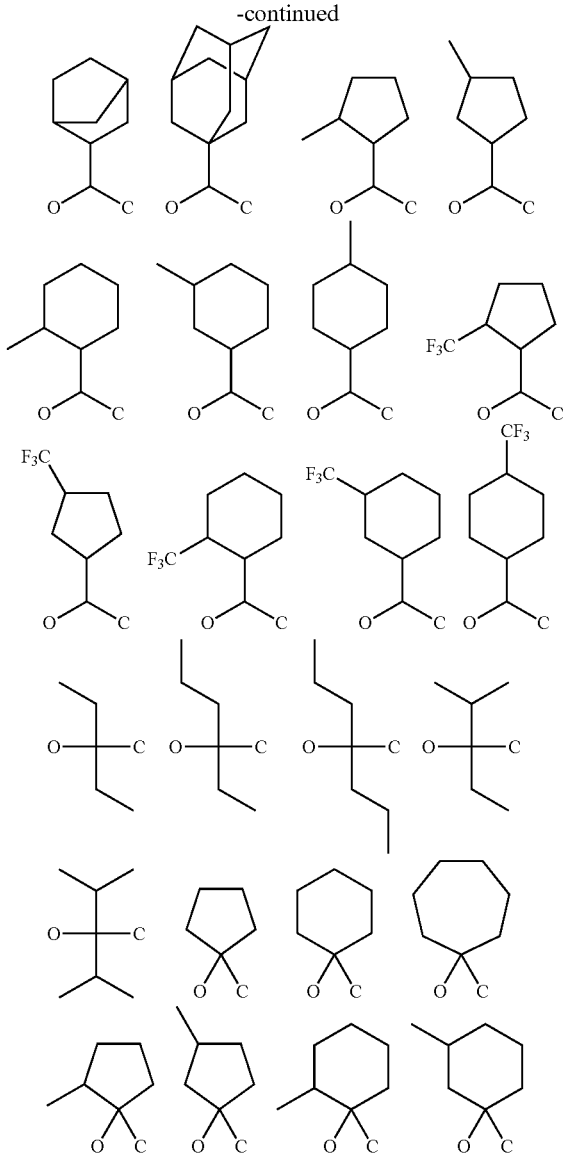
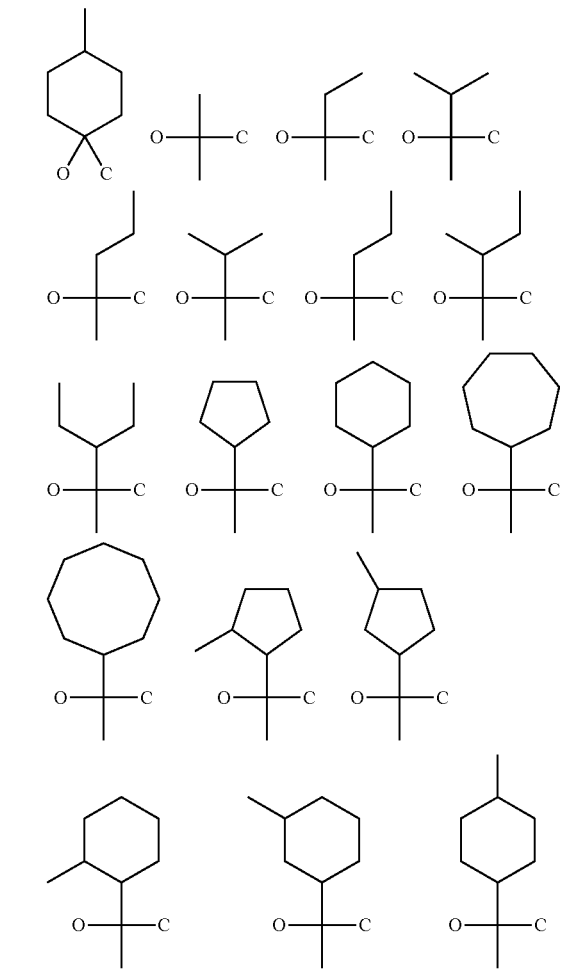
where O and C indicate an oxygen atom and a carbon atom located adjacent to the substituted methylene group.
* * * * *

UNITED STATES PATENT AND TRADEMARK OFFICE
CERTIFICATE OF CORRECTION

PATENT NO.       : 8,686,098 B2
APPLICATION NO.  : 13/375026
DATED            : April 1, 2014
INVENTOR(S)      : Kazunori Mori et al.

Page 1 of 1

It is certified that error appears in the above-identified patent and that said Letters Patent is hereby corrected as shown below:

In the Claims

Col. 76, line 57-65

Replace the formula (2) in claim 1 with the following:

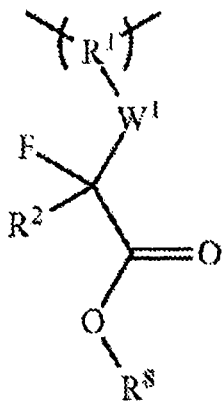

Signed and Sealed this
Twenty-sixth Day of August, 2014

Michelle K. Lee
*Deputy Director of the United States Patent and Trademark Office*